United States Patent
Phelps et al.

(10) Patent No.: US 8,610,018 B2
(45) Date of Patent: Dec. 17, 2013

(54) METHODS AND APPARATUS FOR SELECTIVELY PROCESSING EGGS HAVING IDENTIFIED CHARACTERISTICS

(71) Applicant: Embrex, Inc., Durham, NC (US)

(72) Inventors: Patricia V. Phelps, Carrboro, NC (US); B. Alan Chalker, II, Durham, NC (US); William Hayes Ferrell, III, Cary, NC (US); John H. Hebrank, Durham, NC (US); Benjamin Charles McDow, Seneca, SC (US); Edward Atkinson Pomeroy, III, Easley, SC (US); Jonathan Robertson, Greenville, SC (US); Johnny Mark Townsend, Lauren, SC (US)

(73) Assignee: Embrex, Inc., Durham, NC (US)

( * ) Notice: Subject to any disclaimer, the term of this patent is extended or adjusted under 35 U.S.C. 154(b) by 0 days.

(21) Appl. No.: 13/626,356

(22) Filed: Sep. 25, 2012

(65) Prior Publication Data

US 2013/0023040 A1    Jan. 24, 2013

Related U.S. Application Data

(60) Continuation of application No. 12/535,643, filed on Aug. 4, 2009, now Pat. No. 8,399,247, which is a continuation of application No. 10/937,640, filed on Sep. 9, 2004, now abandoned, which is a division of application No. 10/076,490, filed on Feb. 15, 2002, now Pat. No. 7,041,439.

(60) Provisional application No. 60/284,267, filed on Apr. 17, 2001.

(51) Int. Cl.
*A01K 43/00*    (2006.01)

(52) U.S. Cl.
USPC .............. 209/511; 209/10; 209/588; 119/6.8; 422/65

(58) Field of Classification Search
USPC ............. 209/10, 510, 511, 576, 588; 119/6.8; 422/65
See application file for complete search history.

(56) References Cited

U.S. PATENT DOCUMENTS

| 3,321,087 A | 5/1967 | Fuge .............................. 210/459 |
| 3,545,279 A | 12/1970 | Jentzsch et al. ................. 73/422 |

(Continued)

FOREIGN PATENT DOCUMENTS

| JP | 09-127096 A | 5/1997 |
| WO | WO 9814781 | 4/1998 |

(Continued)

OTHER PUBLICATIONS

"Sorting Eggs is Big Business at Embrex", Special Report: Triangle Tech News, The Business Journal, Apr. 20, 2001.

(Continued)

*Primary Examiner* — Joseph C Rodriguez
(74) *Attorney, Agent, or Firm* — Barbara L. Renda; Scott C. Mayhew

(57) ABSTRACT

Methods and apparatus for processing eggs based upon a characteristic such as gender are provided. Material is extracted from each of a plurality of live eggs, the extracted material is assayed to identify eggs having the characteristic, and then eggs identified as having the characteristic are processed accordingly.

16 Claims, 48 Drawing Sheets

(56) References Cited

U.S. PATENT DOCUMENTS

| | | | |
|---|---|---|---|
| 3,592,327 A | 7/1971 | Koch et al. ............... | 198/33 |
| 3,759,667 A | 9/1973 | Bannister et al. .............. | 23/259 |
| 4,199,988 A | 4/1980 | Riegger ............ | 73/422 |
| 4,458,630 A | 7/1984 | Sharma et al. | |
| 4,558,603 A | 12/1985 | Chlosta et al. ............ | 73/864.21 |
| 4,671,652 A | 6/1987 | van Asselt et al. | |
| 4,914,672 A | 4/1990 | Hebrank | |
| 4,955,728 A | 9/1990 | Hebrank | |
| 5,028,421 A | 7/1991 | Fredericksen et al. | |
| 5,055,263 A | 10/1991 | Meltzer ............ | 422/65 |
| 5,056,464 A | 10/1991 | Lewis ............ | 119/6.8 |
| 5,108,703 A * | 4/1992 | Pfost et al. ............ | 422/65 |
| 5,158,038 A | 10/1992 | Sheeks et al. ............ | 119/6.8 |
| 5,226,462 A | 7/1993 | Carl ............ | 141/1 |
| 5,306,510 A | 4/1994 | Meltzer ............ | 422/65 |
| 5,377,618 A | 1/1995 | Crews et al. ............ | 514/182 |
| 5,517,867 A | 5/1996 | Ely et al. ............ | 73/863.85 |
| 5,575,237 A | 11/1996 | Ferguson ............ | 119/6.8 |
| 5,648,468 A | 7/1997 | Spaulding ............ | 530/359 |
| 5,699,751 A | 12/1997 | Phelps et al. | |
| 5,784,992 A | 7/1998 | Petitte et al. ............ | 119/6.8 |
| RE35,973 E | 12/1998 | Paul et al. ............ | 119/6.8 |
| 5,898,488 A | 4/1999 | Kuhl ............ | 356/53 |
| 5,900,929 A | 5/1999 | Hebrank et al. ............ | 356/52 |
| 6,006,800 A | 12/1999 | Nakano ............ | 141/130 |
| 6,029,080 A | 2/2000 | Reynnells et al. ............ | 600/407 |
| 6,176,199 B1 | 1/2001 | Gore et al. ............ | 119/6.8 |
| 6,224,316 B1 * | 5/2001 | Hebrank et al. ............ | 414/404 |
| 6,234,320 B1 | 5/2001 | Hebrank | |
| 6,240,877 B1 | 6/2001 | Bounds ............ | 119/6.8 |
| 6,244,214 B1 | 6/2001 | Hebrank ............ | 119/6.8 |
| 6,286,455 B1 | 9/2001 | Williams ............ | 119/6.8 |
| 6,365,339 B1 | 4/2002 | Daum et al. ............ | 435/4 |
| 6,395,961 B1 | 5/2002 | Petitte et al. | |
| 6,506,570 B1 | 1/2003 | Phelps ............ | 435/7.21 |
| 6,852,283 B2 * | 2/2005 | Acosta et al. ............ | 422/65 |
| 6,919,044 B1 * | 7/2005 | Shibata et al. ............ | 422/63 |
| 7,041,439 B2 | 5/2006 | Phelps et al. ............ | 435/4 |
| 7,101,715 B2 * | 9/2006 | Devlin et al. ............ | 436/43 |
| 8,235,003 B2 * | 8/2012 | Hebrank et al. ............ | 119/6.8 |
| 8,339,587 B2 * | 12/2012 | Hebrank ............ | 356/53 |
| 8,399,247 B2 * | 3/2013 | Phelps et al. ............ | 435/325 |
| 2002/0014443 A1 * | 2/2002 | Hansen et al. ............ | 209/213 |
| 2003/0096319 A1 | 5/2003 | Phelps ............ | 435/7.2 |
| 2003/0129095 A1 * | 7/2003 | Farina et al. ............ | 422/102 |
| 2013/0017535 A1 * | 1/2013 | Frey et al. ............ | 435/5 |
| 2013/0065797 A1 * | 3/2013 | Silbert et al. ............ | 506/39 |

FOREIGN PATENT DOCUMENTS

| | | |
|---|---|---|
| WO | WO 0022921 | 4/2000 |
| WO | WO 0040079 | 7/2000 |
| WO | WO 02083848 | 10/2002 |

OTHER PUBLICATIONS

Bacon et al., *Poultry Sci.*, vol. 67, pp. 191-197, (1988).
Basrur, et al., *Revista Brasileira de Reproducao Animal*, vol. 22, pp. 133-139, (1998).
Breithofer, et al., *J. Steroid Biochem. Molec. Biol.*, vol. 67, pp. 421-429, (1998).
Burdge, et al., *Analyst*, vol. 123, pp. 2585-2588, (1998).
Butt et al., *Manual of Industrial Microbioloby and Biotechnology*, $2^{nd}$ Edition, Section V, pp. 527-538, (1999).
Butt, et al., *J. Cell Biology*, vol. 107, pp. 304A, Abstract #1712, (1998).
Clinton, et al., *Animal Genetics*, vol. 25, pp. 361-362, (1994).
Coldham, et al., *Environmental Health Perspectives*, vol. 105, pp. 734-742, (1997).
Crittenden, et al., *J. Virol.*, vol. 612, pp. 722-725, (1987).
Ecker et al., *J. Biol. Chem.*, vol. 264, pp. 7715-7719, (1989).
Emmerson, D. A., *Poultry Science*, vol. 76, pp. 1121-1125, (1997).
Gill, et al., *Gen. Comp. Endo.*, vol. 49, pp. 176-186, (1983).
Glahn, et al., *Poultry Science*, vol. 66, pp. 1398-1401, (1987).
Graumann, et al., *J. Steroid Biochem. Molec. Biol.*, vol. 57, pp. 293-300, (1996).
Guichard, et al., *Gen. Comp. Endo.*, vol. 32, pp. 255-267, (1977).
Jull, M. A., *Poultry Science*, vol. XIII, No. 4, pp. 250-254, (1934).
Klein, et al., *J. Clin. Invest.*, vol. 94, 22475-22480, (1994).
Laughlin, et al., *British Poultry Science*, vol. 17, pp. 293-301, (1976).
Lyttle, et al., *J. Steroid Biochem. Molec. Bio.*, vol. 42, pp. 667-685, (1992).
Masui, "Sexing Baby Chicks", Journal Printing Company, (1934).
Monia et al., *J. Cell. Biology*, vol. 107, pp. 613A, Abstract #3475, (1988).
Murata, et al., *Analytical Sciences*. vol. 17, pp. 387-390, (March 200).
Petit, et al., *Aquaculture*, vol. 177, pp. 353-365, (1999).
Pettite, et al., *Proceedings of the XIX World's Poultry Congress*, pp. 531, (1992).
Romanoff, A., "Biochemistry of the Avian Embryo", (1967)).
Routledge, et al., *Environmental Toxicology and Chemistry*, vol. 15, pp. 241-248, (1996).
Schroeder, C. H., *Everybody's Poultry Journal*, vol. 289, pp. 293-297, (1933).
Tanabe, et al., *Gen. Comp. Endo.* vol. 39, pp. 26-33, (1979).
Taylor, L. W., "Sexing Day Old Chicks", pp. 14, (1933).
Tsay, et al., *Clinical Chemistry*, vol. 37, No. 9, pp. 1502-1501, (1991).
Uryu, et al., *Poultry Science*, vol. 68, pp. 850-853, (1989).
Vinggaard, et al., *Chem. Res. Toxicol.*, vol. 13, pp. 1214-1222, (2000).
Warren, D. C., *Poultry Tribune*, pp. 30-34, (1976).
Zhou & Lamont, *Animal Genetics*, vol. 30, pp. 256-264, (1999).
Petitte, James N. and Kegelmeyer, A. Elizabeth, Rapid sex determination of chick embryos using the polymerase chain reaction, Animal Biotechnology, 1995, vol. 6, No. 2, pp. 119-130.
PCT International Search Report, International Application No. PCT/US02/11347, Date of Mailing May 5, 2003.
PCT International Preliminary Examination Report, International Application No. PCT/US02/11347, Date of completion of this report Jun. 2, 2003.

* cited by examiner

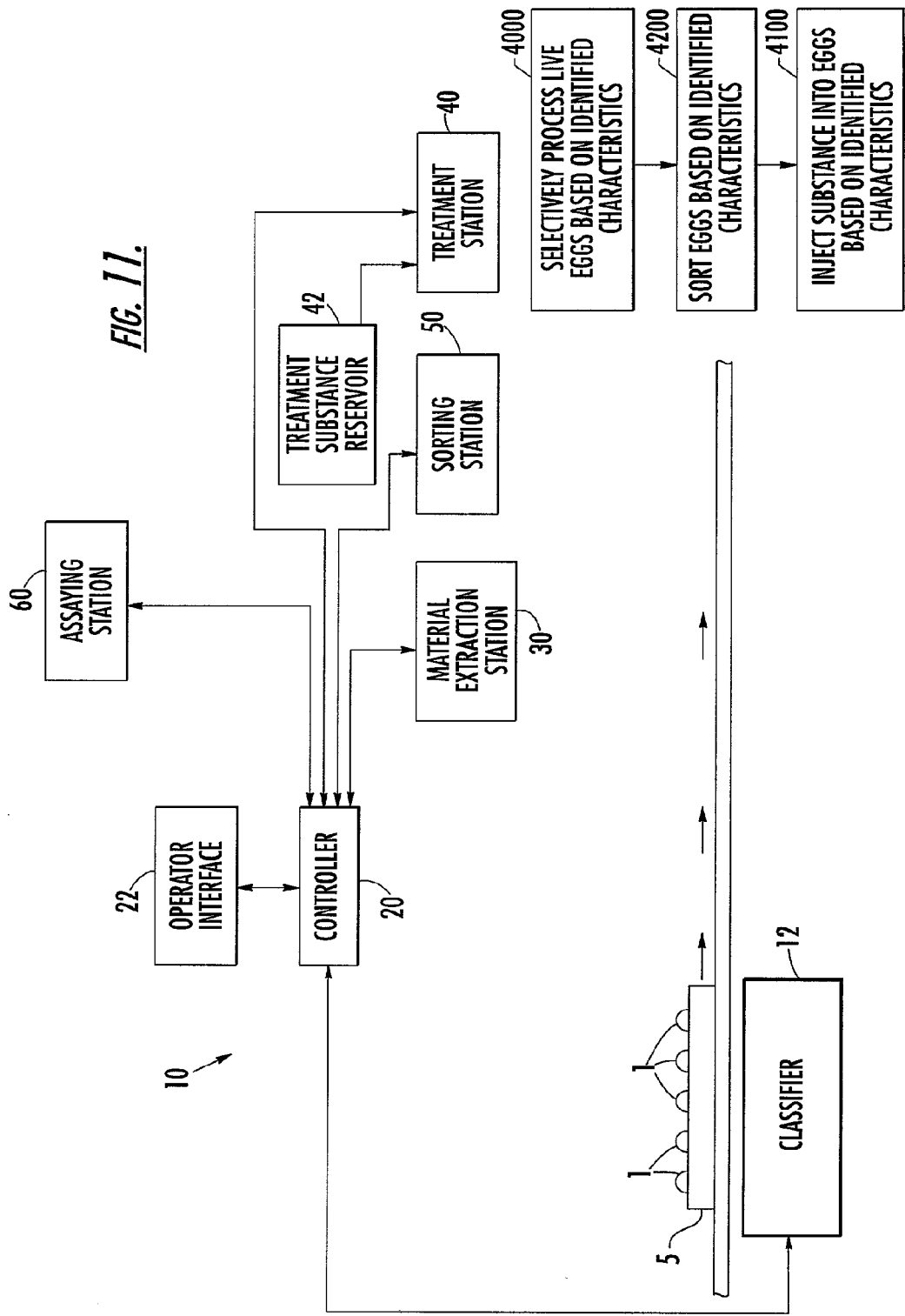

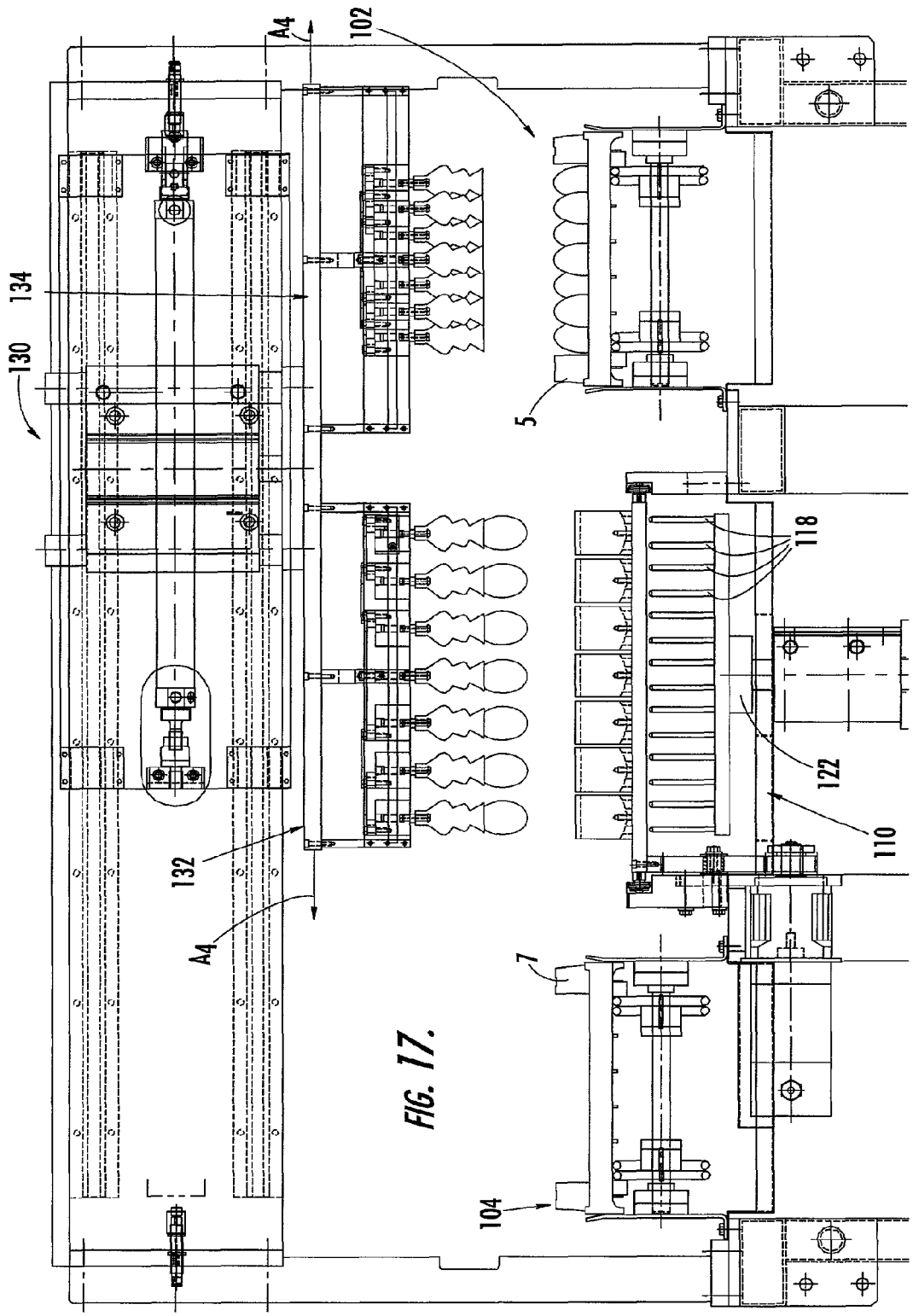

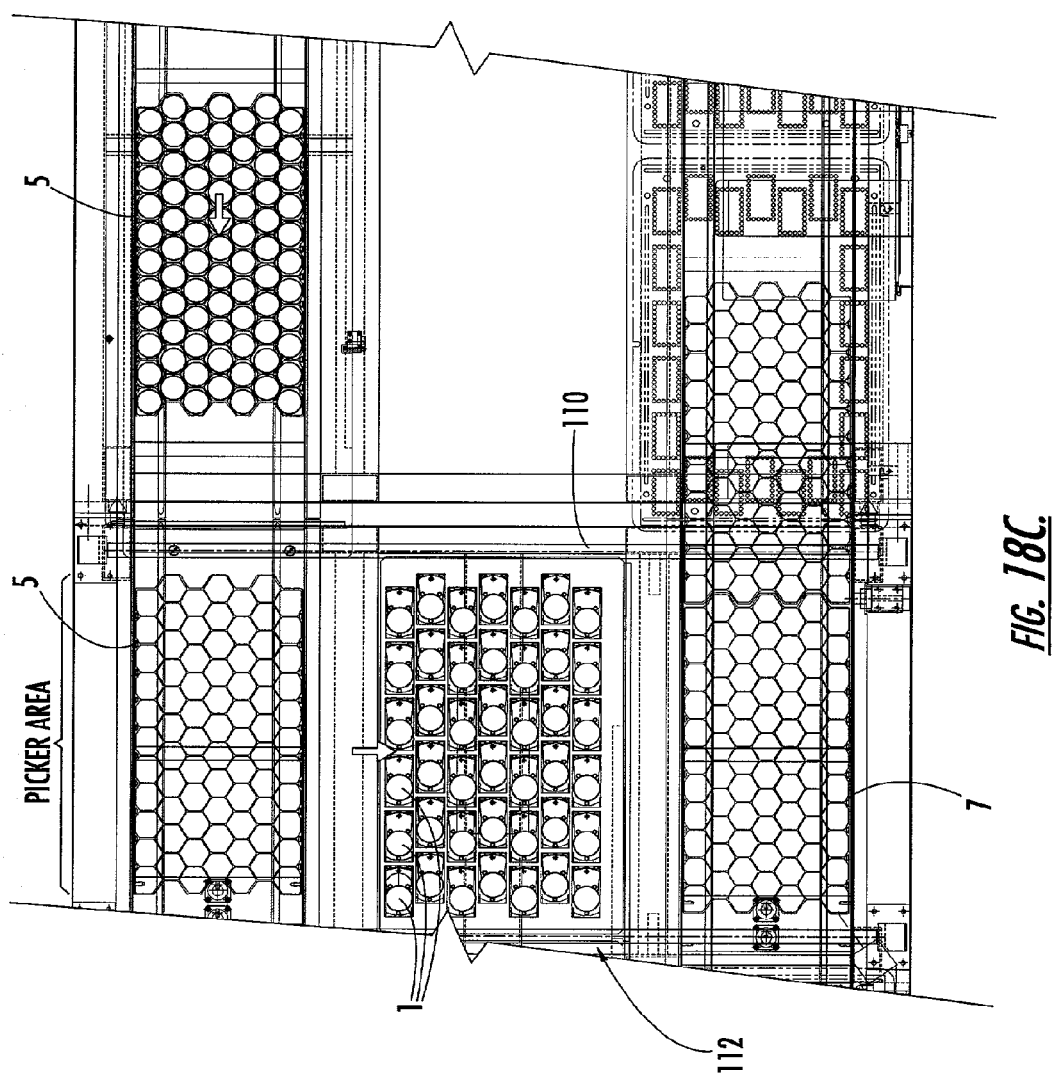

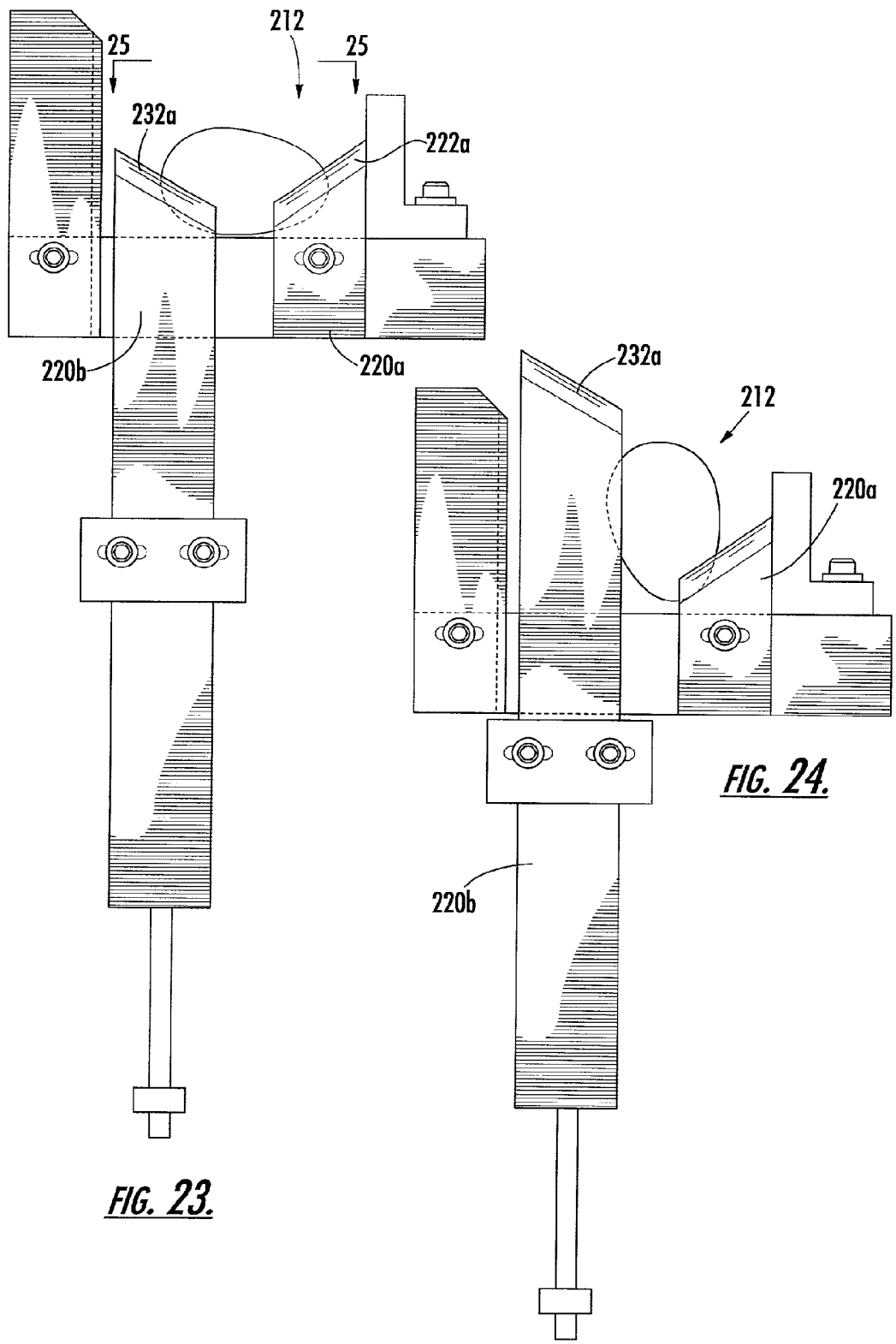

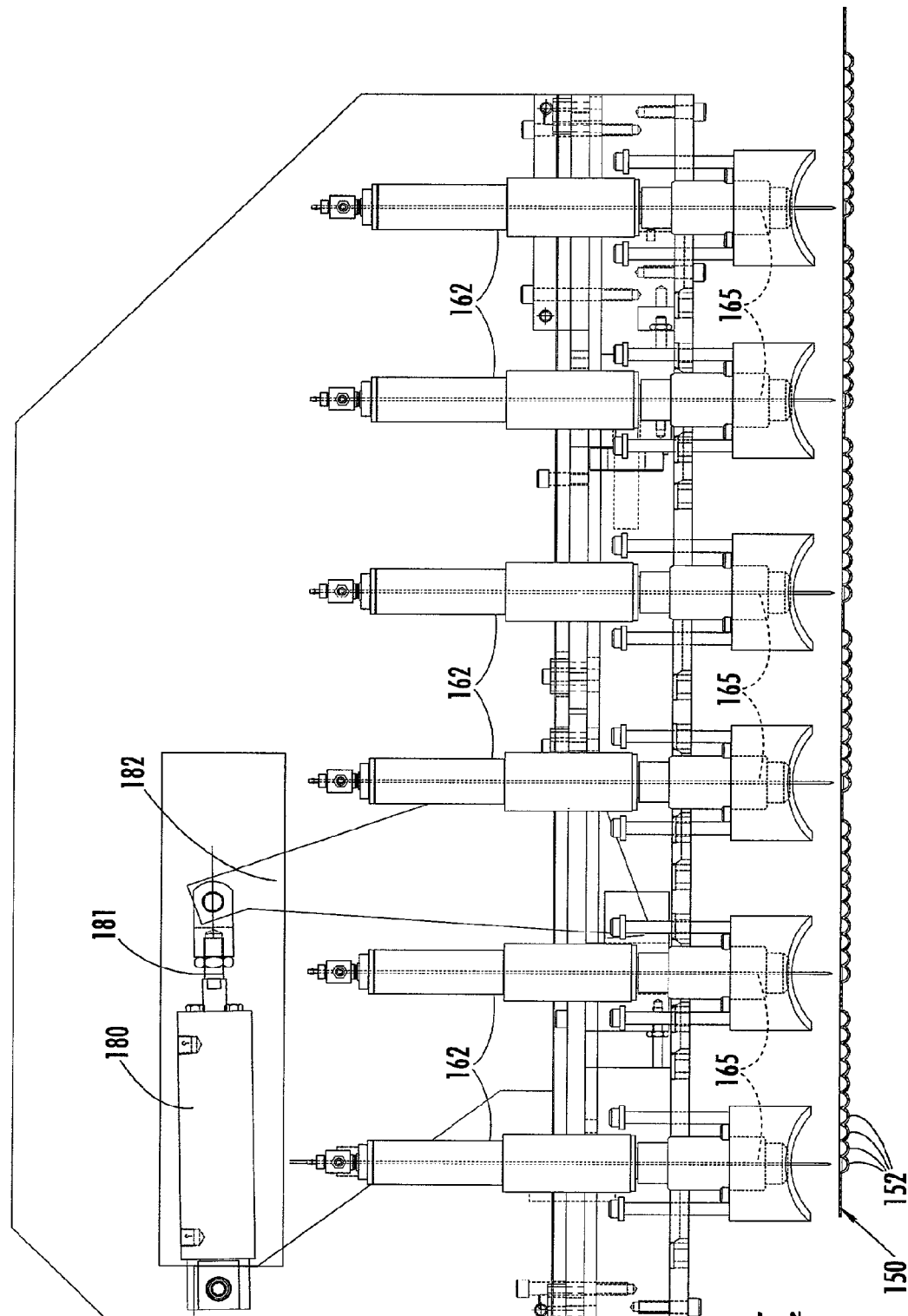

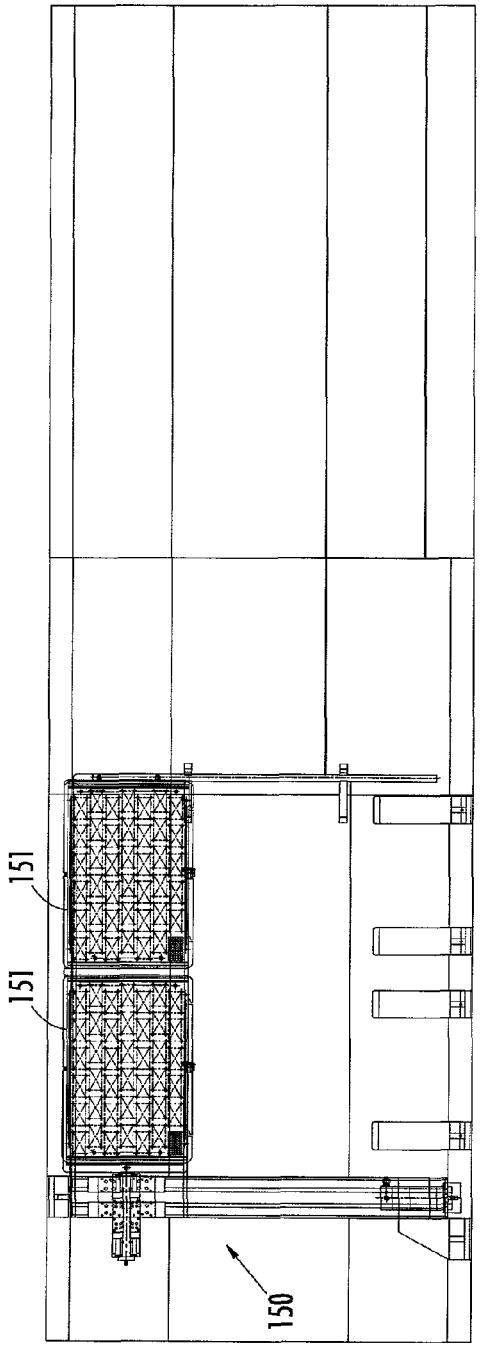
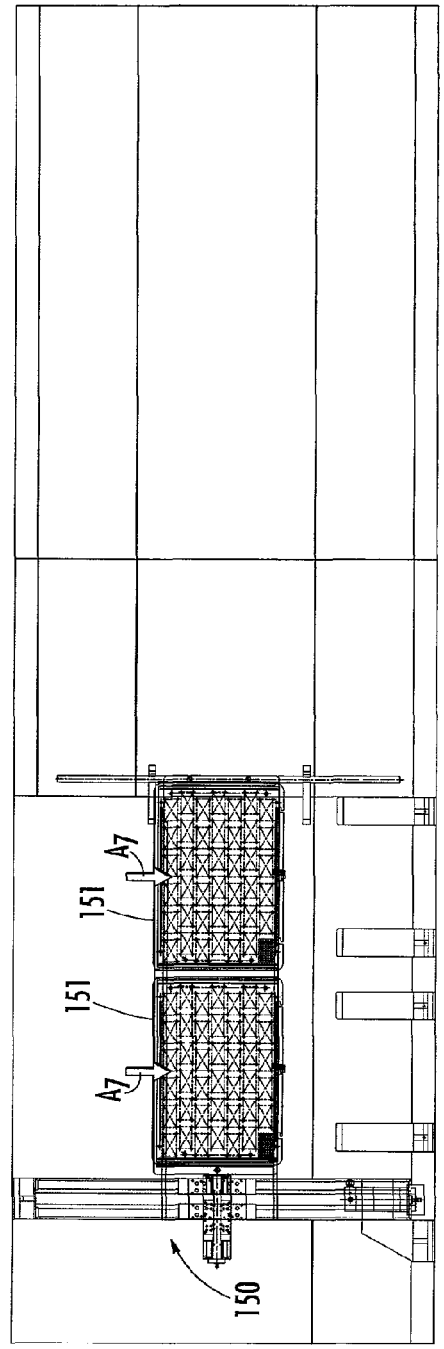
FIG. 42A.
FIG. 42B.

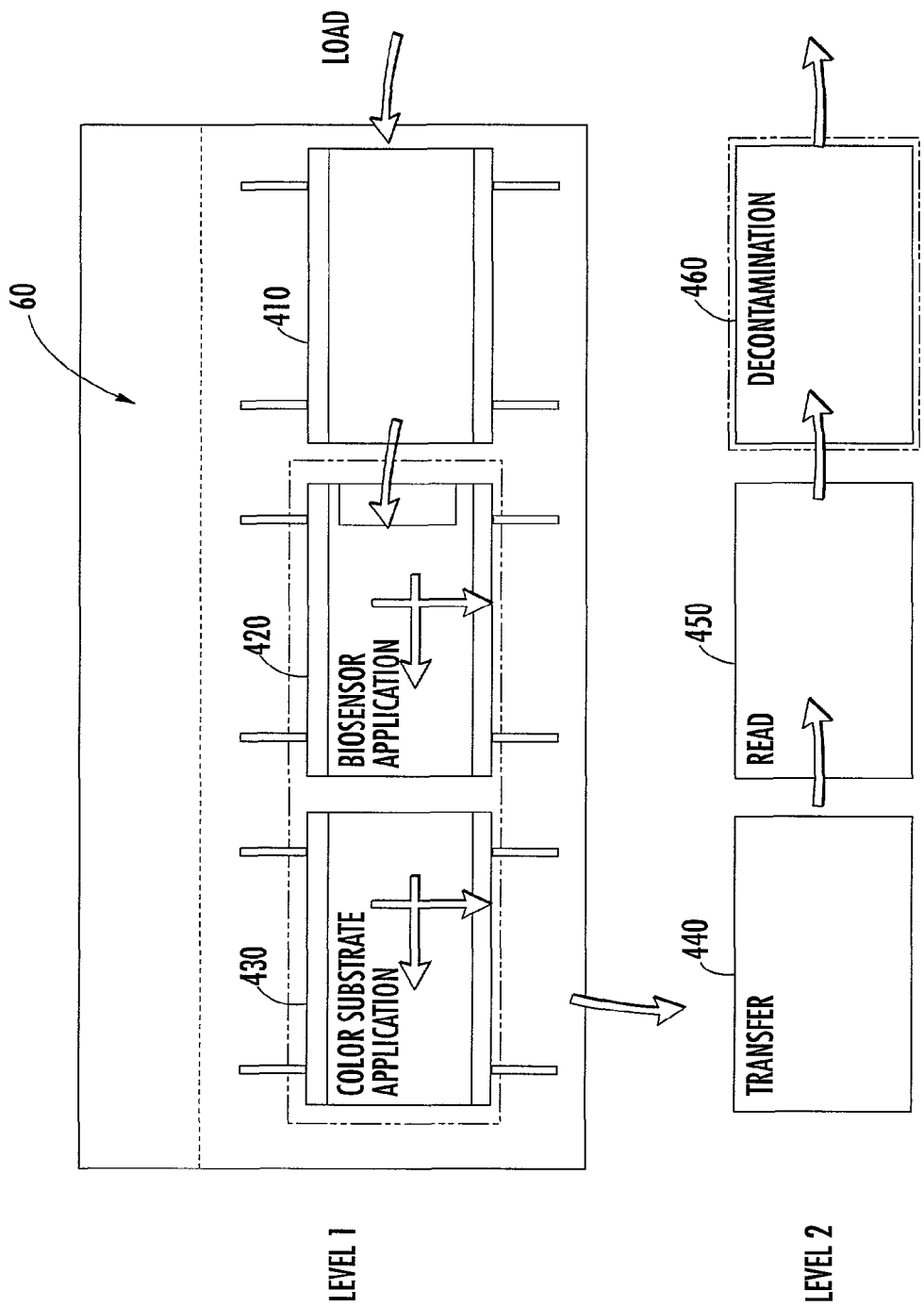

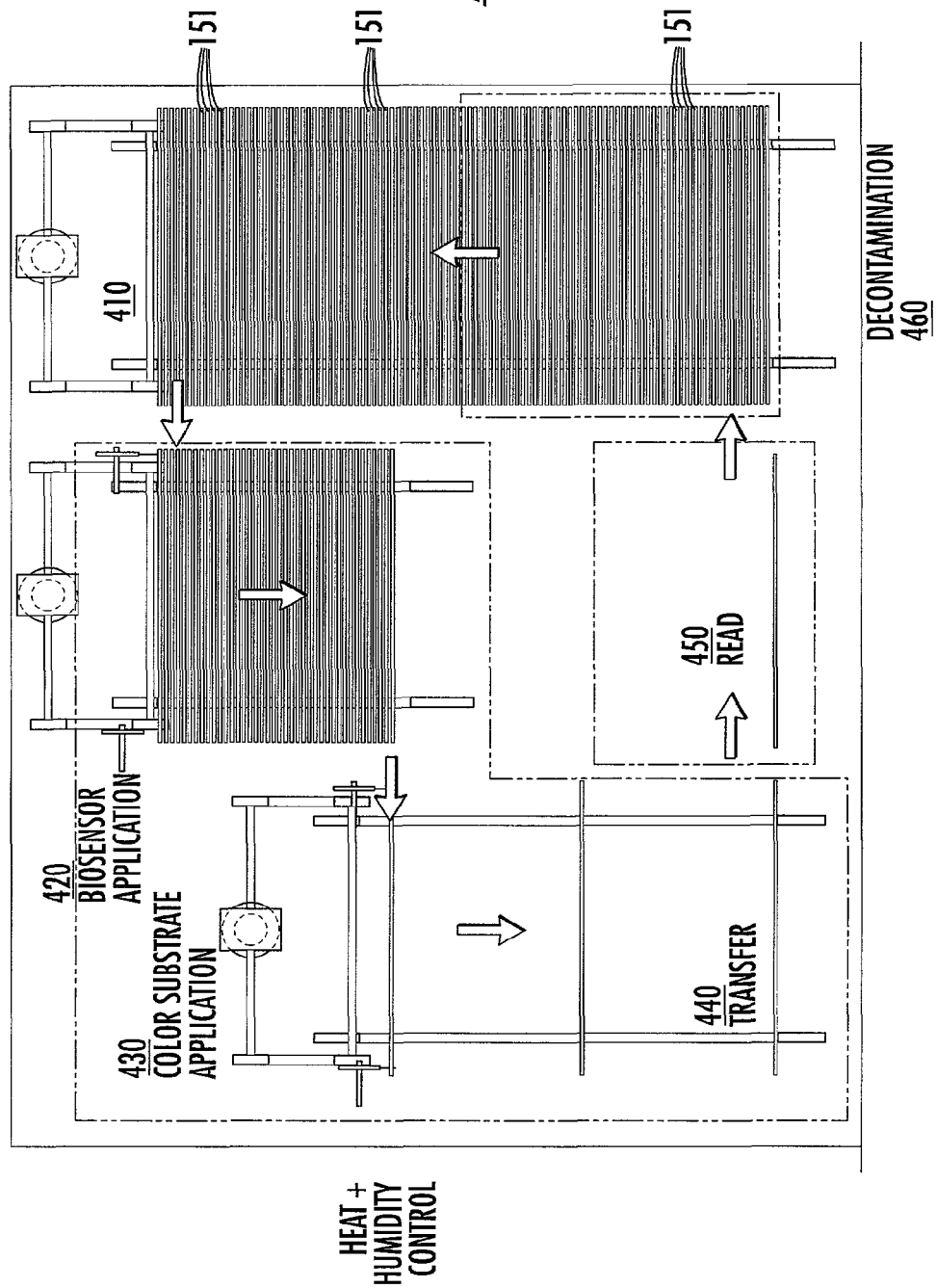

METHODS AND APPARATUS FOR SELECTIVELY PROCESSING EGGS HAVING IDENTIFIED CHARACTERISTICS

CROSS-REFERENCE TO RELATED APPLICATIONS

This application is a continuation of U.S. application Ser. No. 12/535,643, filed Aug. 4, 2009, which is a continuation of U.S. application Ser. No. 10/937,640, filed Sep. 9, 2004, which is a divisional of U.S. application Ser. No. 10/076,490, filed Feb. 15, 2002, now U.S. Pat. No. 7,041,439, which claims the benefit of U.S. Provisional Application No. 60/284,267, filed Apr. 17, 2001, all of which are expressly incorporated herein by reference in their entirety.

FIELD OF THE INVENTION

The present invention relates generally to eggs and, more particularly, to methods and apparatus for processing eggs.

BACKGROUND OF THE INVENTION

Discrimination between poultry eggs (hereinafter "eggs") on the basis of some observable quality is a well-known and long-used practice in the poultry industry. "Candling" is a common name for one such technique, a term which has its roots in the original practice of inspecting an egg using the light from a candle. Although egg shells appear opaque under most lighting conditions, eggs are actually somewhat translucent. Accordingly, when placed in front of a light, the contents of an egg can be observed.

In poultry hatcheries, one purpose of candling eggs is to identify and then segregate live eggs (i.e., eggs which are to be hatched to live poultry) from non-live eggs (e.g., clear eggs, dead eggs, rotted eggs, empty eggs, etc.). U.S. Pat. Nos. 4,955,728 and 4,914,672, both to Hebrank, describe a candling apparatus that uses infrared detectors and the infrared radiation emitted from an egg to identify live eggs. U.S. Pat. No. 4,671,652 to van Asselt et al. describes a candling apparatus in which a plurality of light sources and corresponding light detectors are mounted in an array, and wherein eggs are passed between the light sources and the light detectors to identify live eggs.

Once identified, live avian eggs may be treated with medications, nutrients, hormones and/or other beneficial substances while the embryos are still in the egg (i.e., in ovo). In ovo injections of various substances into avian eggs have been employed to decrease post-hatch morbidity and mortality rates, increase the potential growth rates or eventual size of the resulting bird, and even to influence the gender determination of the embryo. Injection of vaccines into live eggs have been effectively employed to immunize birds in ovo. It is further desirable in the poultry industry to manipulate an embryo in ovo to introduce foreign nucleic acid molecules (i.e., to create a transgenic bird) or to introduce foreign cells (i.e., to create a chimeric bird) into the developing embryo.

In ovo injection of a virus may be utilized to propagate the particular virus for use in preparation of vaccines. Examples of substances that have been used for, or proposed for, in ovo injection include vaccines, antibiotics and vitamins. Examples of in ovo treatment substances and methods of in ovo injection are described in U.S. Pat. No. 4,458,630 to Sharma et al. and U.S. Pat. No. 5,028,421 to Fredericksen et al.

Improved methods of injecting eggs containing an embryo may be used to remove samples from eggs, including embryonic and extra-embryonic materials; Further, for other applications it may be desirable to insert a sensing device inside an egg containing an embryo to collect information therefrom, for example, as described in U.S. Pat. No. 6,244,214 to Hebrank, which is incorporated herein by reference in its entirety.

In commercial hatcheries, eggs typically are held in setting flats during incubation. At a selected time, typically on the eighteenth day of incubation, the eggs are removed from an incubator. Unfit eggs (namely, dead eggs, rotted eggs, empties, and clear eggs) are identified and removed, live eggs are treated (e.g., inoculated) and then transferred to hatching baskets.

In hatchery management, it may be desirable to separate birds based upon various characteristics, such as gender, diseases, genetic traits, etc. For example, it may be desirable to inoculate male birds with a particular vaccine and inoculate female birds with a different vaccine. Sex separation of birds at hatch may be important for other reasons as well. For example, turkeys are conventionally segregated by sex because of the difference in growth rate and nutritional requirements of male and female turkeys. In the layer or table egg industry, it is desirable to keep only females. In the broiler industry, it is desirable to segregate birds based on sex to gain feed efficiencies, improve processing uniformity, and reduce production costs.

Unfortunately, conventional methods of sexing birds may be expensive, labor intensive, time consuming, and typically require trained persons with specialized skills. Conventional methods of sexing birds include feather sexing, vent sexing, and DNA or blood sexing. About three-thousand (3,000) chicks can be feather-sexed per hour at a cost of about 0.7 to 2.5 cents per chick. About fifteen hundred (1,500) chicks can be vent-sexed per hour at a cost of about 3.6 to 4.8 cents per chick. DNA or blood sexing is performed by analyzing a small sample of blood collected from a bird.

It would be desirable to identify the sex of birds, as well as other characteristics of birds, prior to hatching. Pre-hatch sex identification could reduce costs significantly for various members of the poultry industry. Although conventional candling techniques can discriminate somewhat effectively between live and non-live eggs, these conventional candling techniques may not be able to reliably determine gender and other characteristics of unhatched birds.

SUMMARY OF THE INVENTION

In view of the above discussion, embodiments of the present invention provide methods of processing eggs having an identified characteristic (e.g., gender) wherein material (e.g., allantoic fluid, amnion, yolk, shell, albumen, tissue, membrane and/or blood, etc.) is extracted from each of a plurality of live eggs, the extracted material is assayed to identify eggs having a characteristic, and then eggs identified as having the characteristic are processed accordingly. For example, a method of processing eggs based upon gender, according to embodiments of the present invention, includes identifying live eggs among a plurality of eggs, extracting allantoic fluid from the eggs identified as live eggs, detecting a presence of an estrogenic compound in the allantoic fluid extracted from each live egg to identify a gender of each live egg, detecting a color change of the allantoic fluid to identify the gender of each egg, and then selectively injecting a vaccine into the live eggs according to gender.

According to embodiments of the present invention, extracting allantoic fluid from the eggs includes positioning each of the live eggs in a generally horizontal orientation whereby an allantois of each egg is caused to pool and enlarge an allantoic sac under an upper portion of each egg shell, inserting a probe (e.g., a needle) into each egg through the shell of the egg and directly into the enlarged allantoic sac, and withdrawing a sample of allantoic fluid from the allantois of each egg via each probe. According to embodiments of the present invention, detecting a presence of an estrogenic compound in the allantoic fluid includes dispensing allantoic fluid extracted from the live eggs into respective receptacles, and dispensing a biosensor into the receptacles, wherein the biosensor is configured to chemically react with an estrogenic compound in the allantoic fluid and change a color of the allantoic fluid.

According to embodiments of the present invention, selectively injecting a vaccine into the live eggs according to gender includes injecting a first vaccine into live eggs identified as male, and injecting a second vaccine into live eggs identified as female. Alternatively, selectively injecting a vaccine into the live eggs according to gender includes injecting a vaccine into live eggs identified as having the same gender.

According to other embodiments of the present invention, material extracted from eggs may be assayed to identify one or more pathogens within each egg. Eggs identified as having one or more pathogens are subsequently removed from the remaining live eggs.

According to other embodiments of the present invention, genetic analyses may be performed on material extracted from eggs.

According to embodiments of the present invention, an automated gender sorting system is provided and includes three independent modules linked via a network. The first module is an allantoic fluid sampling module. Flats of eggs are removed from a setting incubator, typically on Day 15, 16, or 17 of a 21-Day incubation cycle, and fed onto a conveyor belt. An optical-based sensor automatically identifies live eggs and the eggs (either only live eggs or all eggs) are transferred into an array of egg cradles. Each egg cradle is configured to reposition a respective egg onto its side and to center the egg. A needle is then inserted into each egg to a depth of about five to six millimeters (5-6 mm) into about the midpoint of an egg, and allantoic fluid (e.g., about 20 .mu.1) is withdrawn. The fluid sample from each egg is deposited into a respective well in a bar-coded assay template. The wells in the template may be arranged in the same array as the array of the egg flat, according to embodiments of the present invention. Each sampling needle is sanitized before being used to sample material from another egg.

The eggs are repositioned via the cradles to upright positions and then returned to a bar-coded egg flat. The flats are then typically returned to a setting incubator. The assay templates containing the sampled material (e.g., allantoic fluid) from the eggs are stacked for processing, and a data processor on the network matches the barcodes of each egg flat and assay template. The second module is an automated assaying module. An operator loads a plurality of assay templates containing sampled material (e.g., allantoic fluid) from eggs into the assaying module. Within the assaying module, each assay template is moved via a conveyor system beneath a dispensing head which dispenses a predetermined amount (e.g., about 75 μl) of reagent (e.g., a LiveSensors™ brand cell-based biosensor, LifeSensors, Inc., Malvern, Pa.) into each respective well. Each assay template then progresses through an environmentally-controlled chamber for a predetermined period of time (e.g., about 3.5 hours). Each assay template is moved via a conveyor system beneath another dispensing head which dispenses a predetermined amount of a color substrate (e.g., ONPG-based substrate), into each well. Each assay template then progresses through an environmentally-controlled chamber for a predetermined period of time (e.g., about 45 minutes) to allow color development within each well.

A CCD (charge-coupled device) camera then scans each well to determine the gender of a respective egg whose sample material is in the well. This information is stored via a data processor on the network. According to embodiments of the present invention, the reagent (e.g., a LiveSensors™ brand cell-based biosensor) within each well is then destroyed (e.g., via heat and/or via chemical treatment) prior to disposal of each assay template.

The third module is an egg treatment and sorting module. According to embodiments of the present invention, the bar-coded egg flats are removed from the setting incubator towards the end of the 21-Day incubation cycle (e.g., Day 18 or 19, etc.) and placed on a conveyor system. According to embodiments of the present invention, a data processor on the network identifies which eggs are male and which eggs are female based on information previously stored. The male eggs are then vaccinated with a male-specific vaccination and the female eggs are vaccinated with a female-specific vaccination. According to embodiments of the present invention, separate vaccination devices may be utilized for male and female eggs. Once vaccinated, the eggs are sorted by gender and transferred to gender-specific hatching baskets. The hatching baskets are then transferred to hatching incubators. According to embodiments of the present invention, eggs of one gender can be discarded and not vaccinated or transferred into hatching baskets.

According to embodiments of the present invention, eggs are separated by gender (or other characteristic) first and then processed. For example, eggs may be sorted by gender and then the male and female eggs are processed separately.

According to embodiments of the present invention, estrogenic compounds present in the allantoic fluid of female embryos, but not male embryos, are detected. Avian embryos can be gender sorted on the basis of the presence of estrogenic compounds in the allantoic fluid of female embryos between days thirteen and eighteen (13-18) of incubation, in broiler, broiler breeder, turkey, and layer embryos, and regardless of flock age or strain.

Embodiments of the present invention can facilitate increased production efficiencies by contributing to savings in incubation space (e.g., not hatching chicks identified as males pre-hatch), by contributing to savings in vaccinations, by allowing reduction in manual labor, and by increasing hatchery processing speeds. For example, throughput rates of between about twenty thousand and thirty thousand (20,000-30,000) eggs per hour can be gender sorted and vaccinated via embodiments of the present invention, and with an accuracy rate exceeding ninety-eight percent (98%). Because the gender of eggs are known prior to vaccination, savings in vaccination costs can be realized particularly when it is desirable to vaccinate only a specific gender. In addition, embodiments of the present invention can be easy to operate, even by unskilled workers.

BRIEF DESCRIPTION OF THE DRAWINGS

FIG. 6 is a flowchart of operations for light and thermal candling of eggs, according to embodiments of the present invention.

FIGS. 10A-10B are flowcharts of operations for selectively processing eggs based on identified characteristics, according to embodiments of the present invention.

FIG. 11 is a block diagram of systems and methods for processing eggs, according to embodiments of the present invention.

FIG. 17 is a side elevation view of the material extraction apparatus of FIG. 14 illustrating lateral movement of the egg transfer apparatus between the two egg flat conveyor systems and the egg cradles.

FIG. 18A also illustrates an incoming egg flat positioned within the candling area of the material extraction apparatus of FIG. 14.

FIG. 18C illustrates a plurality of eggs seated within the plurality of egg cradles after being transferred from an incoming egg flat by the egg transfer apparatus.

FIG. 23 is a side view of an egg positioning apparatus, according to alternative embodiments of the present invention, and wherein an egg is in a generally horizontal position therein.

FIG. 24 illustrates the egg positioning apparatus of FIG. 23, wherein the egg is being urged to a generally vertical orientation by an orientation member.

FIG. 35 illustrates the sample heads of FIG. 33 wherein the sample needles are in a second extended position for dispensing material extracted from respective eggs into respective sample receptacles in an assay template.

FIGS. 42A-42B are top plan views of the sample tray handling system according to embodiments of the present invention and illustrating sample trays being moved relative to the sampling apparatus of FIG. 14.

FIGS. 43-44 are block diagrams of systems and methods for assaying material extracted from a plurality of eggs in order to identify eggs having one or more characteristics, according to embodiments of the present invention.

DETAILED DESCRIPTION OF THE INVENTION

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used in the description of the invention and the appended claims, the singular forms "a", "an" and "the" are intended to include the plural forms as well, unless the context clearly indicates otherwise.

All publications, patent applications, patents, and other references mentioned herein are incorporated by reference in their entirety.

The terms "bird" and "avian" as used herein, include males or females of any avian species, but are primarily intended to encompass poultry which are commercially raised for eggs or meat. Accordingly, the terms "bird" and "avian" are particularly intended to encompass chickens, turkeys, ducks, geese, quail and pheasant. The term "in ovo," as used herein, refers to birds contained within an egg prior to hatch. The present invention may be practiced with any type of bird egg, including, but not limited to, chicken, turkey, duck, goose, quail, and pheasant eggs.

As used herein, the terms "injection" and "injecting" encompass methods of inserting a device (typically an elongate device) into an egg or embryo, including methods of delivering or discharging a substance into an egg or embryo, methods of removing a substance (i.e., a sample) from an egg or embryo, and/or methods of inserting a detector device into an egg or embryo.

As used herein, the term "allantoic fluid" encompasses allantoic fluid with or without the presence of other egg materials. For example, the term allantoic fluid may include a mixture of blood and allantoic fluid.

As used herein, the term "predetermined location" indicates a fixed position or depth within an egg. For example, a device may be injected into an egg to a fixed depth and/or fixed position in the egg. In alternative embodiments, the injection may be carried out based on information obtained from the egg, e.g., regarding the position of the embryo or the subgerminal cavity within the egg.

Figure 1:
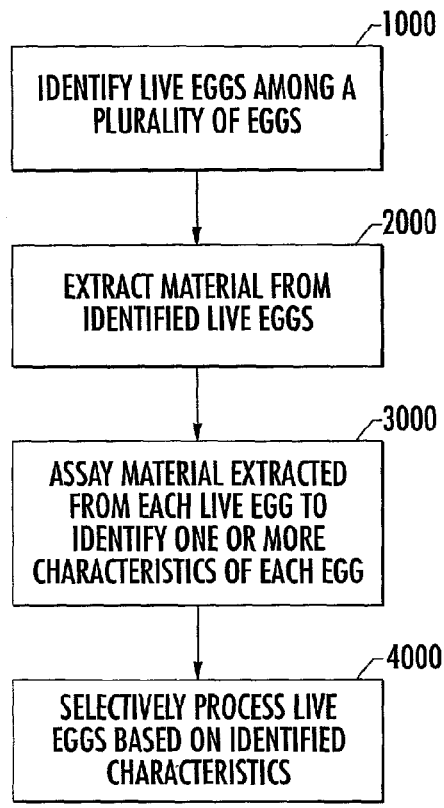
FIG. 1 is a flowchart of operations for processing eggs, according to embodiments of the present invention.

Methods and apparatus according to embodiments of the present invention may be utilized for identifying one or more characteristics of an egg at any time during the embryonic development period (also referred to as the incubation period) thereof. Embodiments of the present invention are not limited to a particular day during the embryonic development period. Referring now to FIG. 1, methods of processing live eggs based upon identified characteristics, according to embodiments of the present invention, are illustrated. Initially, live eggs are identified among a plurality of eggs undergoing incubation (Block 1000). For example, the eggs are candled to identify which eggs are live eggs. Material is extracted from each live egg (Block 2000) and the extracted material is assayed to identify one or more characteristics (e.g., gender, pathogen content, genetic markers related to bird health or performance, nutritional, endocrine or immune indicators or factors, etc.) of the respective egg (Block 3000). The live eggs are then selectively processed based upon the identified one or more characteristics (Block 4000). Each of these operations are described in detail below.

Figure 2:
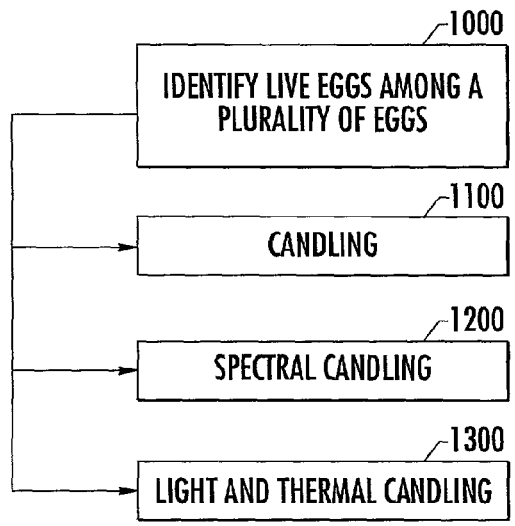
FIG. 2 is a flowchart of operations for identifying live eggs from among a plurality of eggs, according to embodiments of the present invention.

Referring to FIG. 2, identifying live eggs among a plurality of eggs (Block 1000) may involve various techniques including, but not limited to, conventional candling (Block 1100), spectral candling (Block 1200), and the combination of light and thermal candling (Block 1300). Embodiments of the present invention may utilize any method of determining whether an egg contains a live embryo, and are not limited to only the methods described herein.

Figure 3:
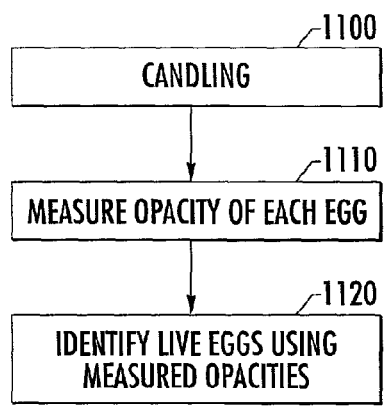
FIG. 3 is a flowchart of operations for candling eggs, according to embodiments of the present invention.

Referring to FIG. 3, conventional candling techniques include measuring the opacity of an egg to visible light, infrared light, and/or other electromagnetic radiation (Block 1110), and then identifying live eggs using measured opacity values (Block 1120). Exemplary candling methods and apparatus are described in U.S. Pat. Nos. 4,955,728 and 4,914,672, both to Hebrank, and U.S. Pat. No. 4,671,652 to van Asselt et al., which are incorporated herein by reference in their entireties. Conventional egg candling techniques are well understood by those of skill in the art and need not be described further herein.

Figure 4:
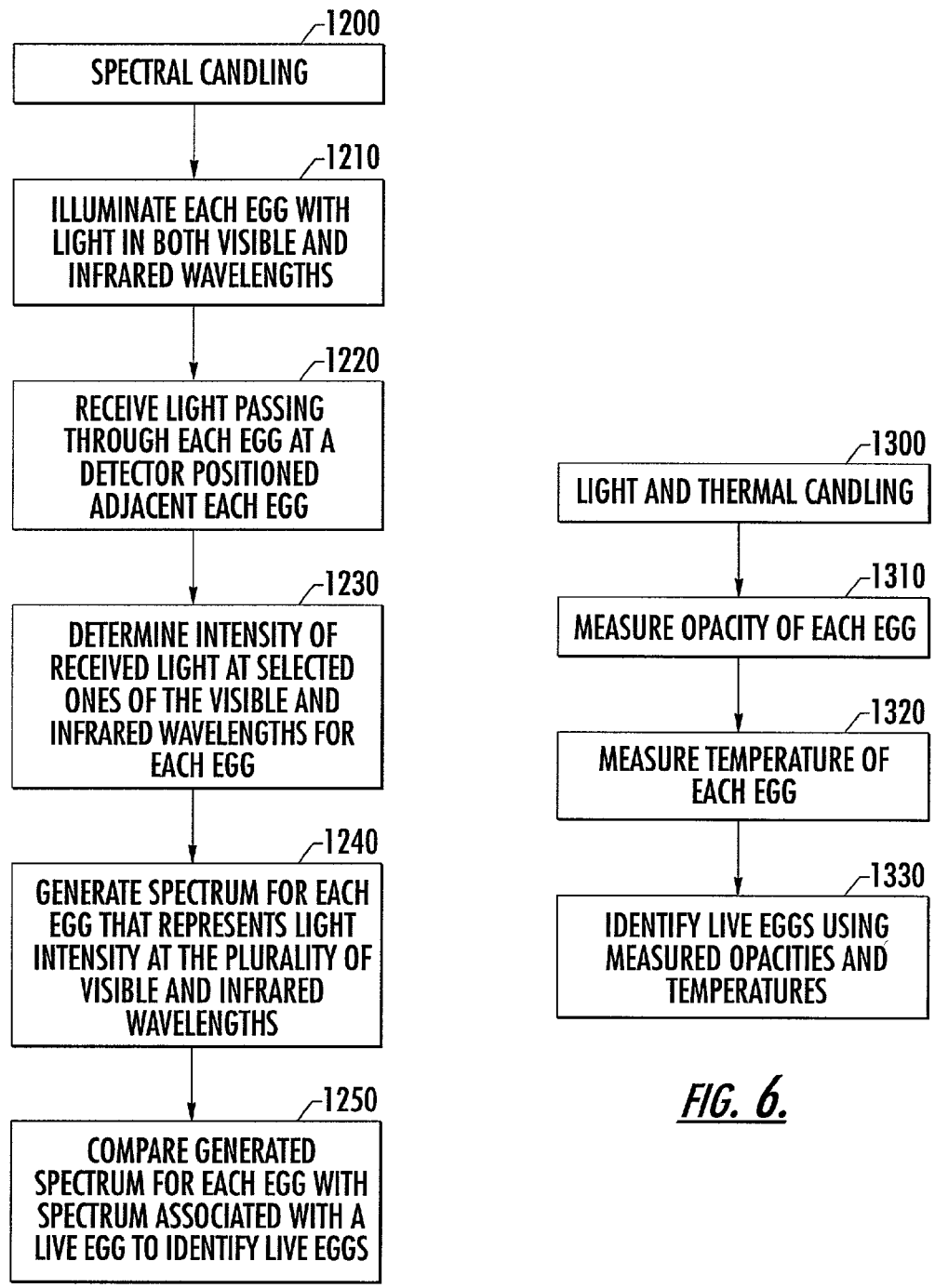
FIG. 4 is a flowchart of operations for spectral candling of eggs, according to embodiments of the present invention.

Referring to FIG. 4, spectral candling (Block 1200) includes illuminating an egg with light in both visible and infrared wavelengths (Block 1210) and then receiving light passing through the egg at a detector positioned adjacent the egg (Block 1220). For example, an egg may be illuminated with light at wavelengths of between about three hundred nanometers and about eleven hundred nanometers (300 nm-1,100 nm). Intensity of the received light is determined at selected visible and infrared wavelengths for the egg (Block 1230) and a spectrum is generated that represents light intensity at the visible and infrared wavelengths (Block 1240). The spectrum generated for the egg is then compared with a spectrum associated with a live egg to identify whether the egg is a live egg (Block 1250).

Figure 5:
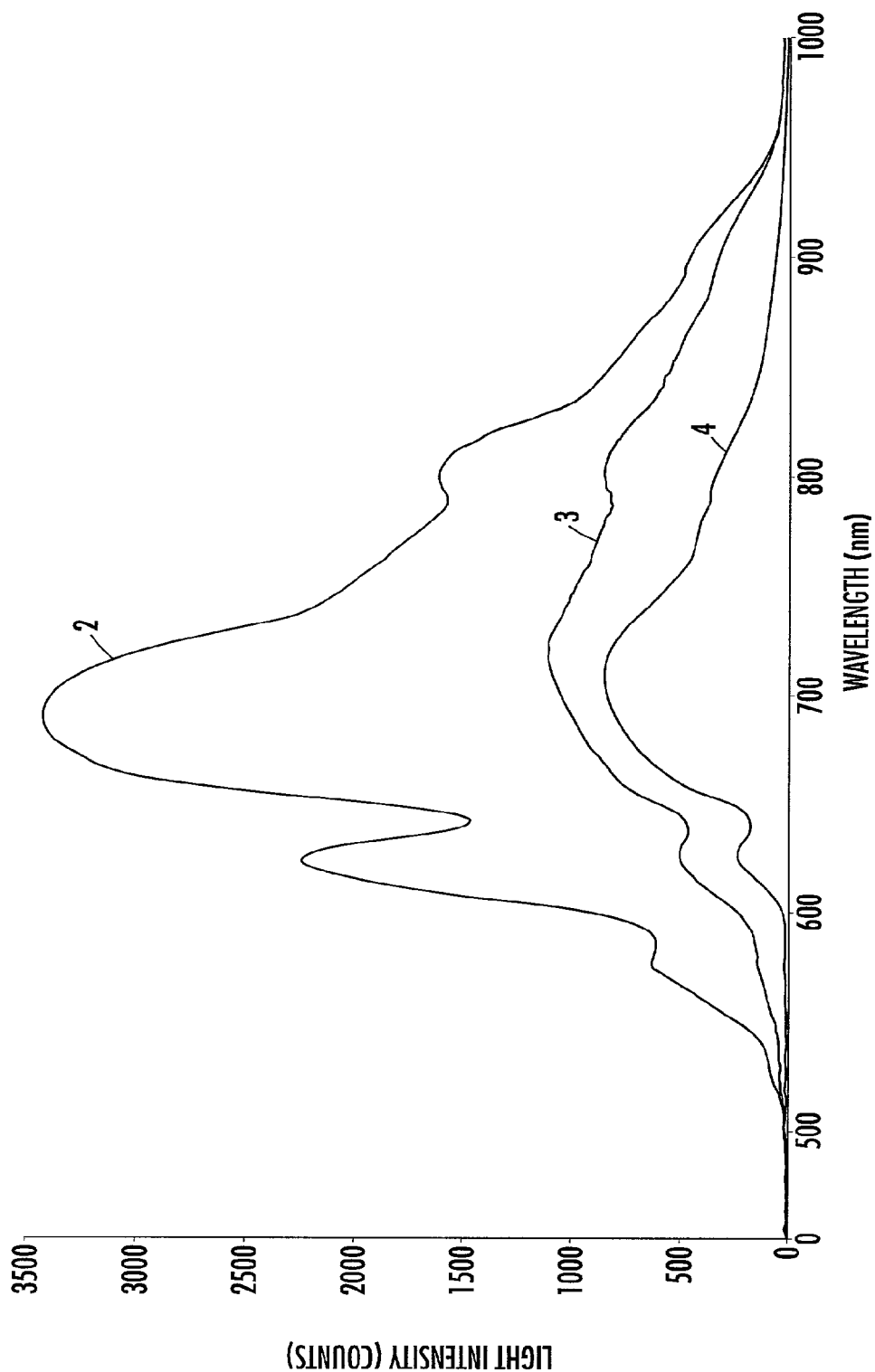
FIG. 5 illustrates exemplary spectra for three eggs subjected to the spectral candling operations of FIG. 4.

FIG. 5 illustrates three spectra for three respective eggs candied via spectral candling techniques. Wavelength in nanometers (nm) is plotted along the X axis, and light intensity counts are plotted along the Y axis. Spectrum 2 is associated with a clear egg. Spectrum 3 is associated with an early dead egg. Spectrum 4 is associated with a live egg. Spectral candling is described in co-assigned U.S. patent application Ser. No. 09/742,167, filed on Dec. 20, 2000, which is incorporated herein by reference in its entirety.

Referring to FIG. 6, light and thermal candling (Block 1300) includes measuring the opacity of an egg (Block 1310), measuring the temperature of the egg (Block 1320), and using the measured opacity and temperature values to identify whether the egg is a live egg (Block 1330). Light and thermal candling is described in co-assigned U.S. patent application Ser. No. 09/563,218, filed May 2, 2000, which is incorporated herein by reference in its entirety.

Figure 7:
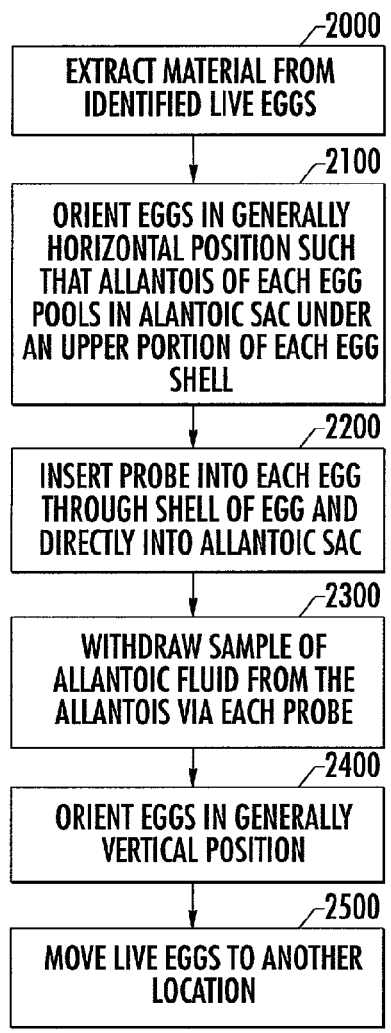
FIG. 7 is a flowchart of operations for extracting material from eggs, according to embodiments of the present invention.
Figure 8:
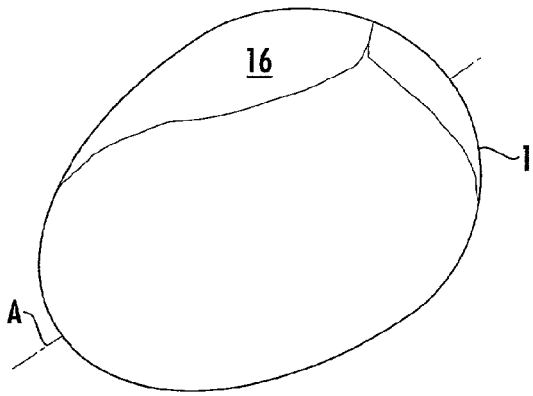
FIG. 8 is a schematic illustration of an egg in a tilted orientation and illustrating the pooling of the allantois under the upper shell of the egg.

Referring to FIG. 7, operations for extracting material from live eggs (Block 2000), according to embodiments of the present invention, will now be described. A plurality of live eggs are positioned in a generally horizontal orientation such that the allantois of each egg is caused to pool within an allantoic sac under an upper portion of each egg shell (Block 2100). The term "generally horizontal orientation" as used herein means that an egg is positioned such that a long axis thereof is oriented at an angle between about ten degrees (10°) and about one-hundred eighty degrees (180°) from vertical, wherein zero degrees (0°) vertical is defined by a large end of the egg in a vertically upward position. A probe (e.g., a needle, etc.) is inserted into each egg through the shell of the egg and directly into the allantoic sac under the upper portion of the egg shell (Block 2200). FIG. 8 illustrates the pooling of the allantois 16 in an egg 1 under the upper side of the egg as a consequence of non-vertical orientation of the egg (e.g., the long axis A is oriented between about 10° and about 180°).

As is known to those of skill in the art, during the final stages of incubation, the allantois normally exists as a relatively thin layer under the inner shell membrane of an egg, and essentially surrounds the embryo therein. In later stage (third and fourth quarter) embryonated eggs, the allantois can be a difficult target to insert a needle or probe into with accuracy. According to embodiments of the present invention, eggs are oriented generally horizontally such that the allantois can be reliably targeted in ovo. By repositioning eggs to a generally horizontal orientation, accessibility of the allantois is enhanced. See for example, U.S. Pat. No. 6,176,199 to Gore et al., and U.S. Pat. No. 5,699,751 to Phelps et al., which are incorporated herein by reference in their entireties.

As is understood by those of skill in the art, the size of the allantois is related to the stage of embryonic development of the egg to be injected; thus the depth of insertion needed to reach the allantois may vary depending on the developmental stage of the egg as well as the species and strain of avian egg used. The depth of insertion should be deep enough to place the sampling device within the allantois, but not so deep as to pierce the amnion or embryo. According to embodiments of the present invention, use of a blunt-tip needle may help minimize piercing of the amnion or embryo.

The precise location and angle of insertion of a sampling device within an egg is a matter of choice and could be in any area of an egg. Orientation of a sampling device will depend on the orientation of the egg, the equipment available to carry out the material extraction, as well as the purpose of the material extraction.

Embodiments of the present invention are not limited to extracting material from the allantois or from areas near the upper surface of an egg. Removal of material from the allantois as described herein is provided as merely one example of possible embodiments of the present invention. Embodiments of the present invention are not limited only to the extraction of allantoic fluid. Various materials (e.g., amnion, yolk, shell, albumen, tissue, membrane and/or blood, etc.) may be extracted from an egg and assayed to identify one or more characteristics, as described below. Moreover, it is not required that eggs be reoriented into a generally horizontal position prior to extracting material therefrom. Material may be extracted from eggs having virtually any orientation.

Referring back to FIG. 7, a sample of allantoic fluid is withdrawn from the allantois of each egg (Block 2300). The eggs are then reoriented to a generally vertical position for easier handling (Block 2400) and are moved to another location for subsequent processing (Block 2500).

Figure 9:
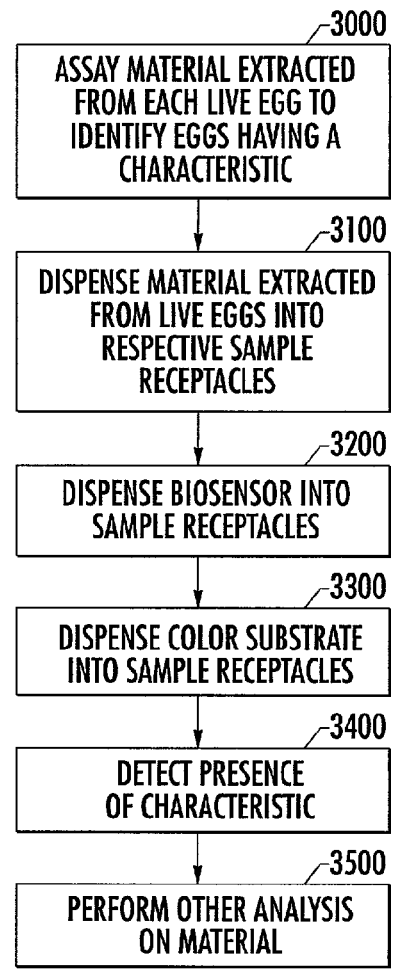
FIG. 9 is a flowchart of operations for assaying extracted egg material to identify a characteristic of eggs, according to embodiments of the present invention.

Referring to FIG. 9, operations for assaying material extracted from each live egg to determine one or more characteristics of the egg, such as gender (Block 3000), according to embodiments of the present invention, will now be described. Material, such as allantoic fluid, is extracted from each egg is dispensed into respective sample receptacles in a template (Block 3100). A biosensor, which is configured to chemically react with egg material and produce detectable signals (e.g., electromagnetic signals, luminescence signals, fluorescence signals, conductivity signals, colormetric signals, pH signals, etc.), is dispensed into the respective sample receptacles (Block 3200). A color substrate (e.g., ONPG-based substrate) that is configured to change a color of the material in response to a chemical reaction between the egg material and the biosensor may be added to each respective receptacle (Block 3300).

The presence of a characteristic of an egg is then detected (Block 3400). For example, a change in color may indicate that estrogenic compounds are present in allantoic fluid within a respective sample receptacle, thereby indicating the gender of a respective egg from which the allantoic fluid was sampled from. Operations represented by Block 3400 are intended to include detection of electromagnetic signals produced within the sample receptacles which provide an indication of the presence of a characteristic of an egg. According to other embodiments of the present invention, operations represented by Block 3400 are intended to include detection of pathogens in egg material.

One or more additional analyses may be performed on the egg material in the sample receptacles (Block 3500). For example, genetic analysis may be performed on the material.

Figure 10A:
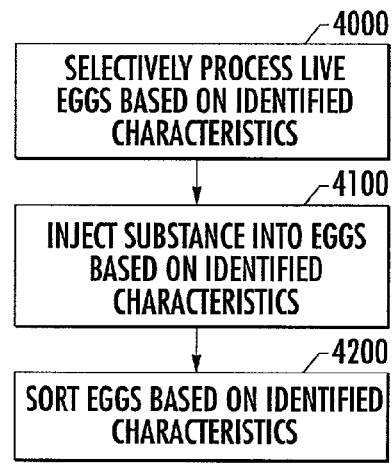

Referring to FIGS. 10A-10B, operations for selectively processing live eggs based upon identified characteristics (Block 4000), according to embodiments of the present invention, will now be described. One or more substances may be injected in ovo based upon identified characteristics of each egg (Block 4100). For example, a vaccine may be injected into eggs according to gender of the eggs. Moreover, a first vaccine may be injected into eggs identified as male, and a second vaccine may be injected into eggs identified as female. In addition, the live eggs may be sorted according to identified characteristics (Block 4200). For example, if the identified characteristic is gender, male eggs may be segregated from female eggs.

Sorting may occur before, after, or in lieu of in ovo injection or other treatment or processing. As illustrated in FIG. 10B, the operations of Block 4100 and 4200 of FIG. 10A can be reversed. For example, eggs may be sorted by gender first and then injected with one or more substances based on gender (e.g., males can be inoculated with a substance and females can be inoculated with a different substance and/or at different times).

Referring now to FIG. 11, an egg processing system 10 for processing eggs, according to embodiments of the present invention, is illustrated. The illustrated system includes a classifier 12 that is configured to identify live eggs from among a plurality of eggs 1 in an incoming egg flat 5. The classifier 12 is operatively connected to a controller 20 which controls the classifier 12 and stores information about each egg 1 (e.g., whether an egg is live, clear, dead, rotted, etc.). As described above, the classifier 12 may include a conventional candling system, a spectral candling system, a candling system that utilizes the combination of light and thermal candling, or any other apparatus/technique for identifying live eggs (and/or dead eggs, clear eggs, rotted eggs, etc.). An operator interface (e.g., a display) 22 is preferably provided to allow an operator to interact with the controller 20.

A material extraction station (also referred to as a sampling module) 30, egg treatment station 40, and egg sorting station 50 are provided downstream of the classifier 12 and are each operatively connected to the controller 20. An assaying station 60 is also operatively connected to the controller 20. The material extraction station 30 is configured to extract material, such as allantoic fluid, from selected eggs. Material extracted from each egg is analyzed via the assaying station 60 to identify one or more characteristics of each egg or for diagnostic or other purposes. For example, the gender of each egg may be identified by analyzing material extracted from an egg. Alternatively, the presence of pathogens may be detected, and/or various genetic analyses may be performed on the extracted material.

The treatment station 40 is configured to treat selected eggs for example, by inoculation with a treatment substance (e.g., vaccines, nutrients, etc.). The treatment station 40 may include at least one reservoir 42 for holding a treatment substance to be injected into selected eggs. The controller 20 generates a selective treatment signal for an egg (or a group of eggs) based upon characteristics of an egg (or a group of eggs) identified via the assaying station 60. For example, eggs identified as female may be injected with a particular vaccine via the treatment station 40 upon receiving a treatment signal from the controller 20.

The sorting station 50 is configured to sort eggs based upon identified characteristics. The controller 20 generates a selective sorting signal for an egg (or a group of eggs) based upon characteristics of an egg (or a group of eggs) identified via the assaying station 60. For example, eggs identified as male may be placed in a first hatching bin, and eggs identified as female may be placed in a second hatching bin.

The assaying station 60 is configured to perform various tests on material extracted from eggs in order to identify one or more characteristics (e.g., gender) of each egg. Various tests may be performed via the assaying station 60. The present invention is not limited only to identifying the gender of eggs.

The controller 20 preferably includes a processor or other suitable programmable or non-programmable circuitry including suitable software. The controller 20 may also include such other devices as appropriate to control the material extraction station 30, egg treatment station 40, egg sorting station 50, and assaying station 60. Suitable devices, circuitry and software for implementing a controller 20 will be readily apparent to those skilled in the art upon reading the foregoing and following descriptions and the disclosures of U.S. Pat. No. 5,745,228 to Hebrank et al. and U.S. Pat. No. 4,955,728 to Hebrank.

The operator interface 22 may be any suitable user interface device and preferably includes a touch screen and/or keyboard. The operator interface 22 may allow a user to retrieve various information from the controller 20, to set various parameters and/or to program/reprogram the controller 20. The operator interface 22 may include other peripheral devices, for example, a printer and a connection to a computer network.

According to alternative embodiments of the present invention, one or more of the stations described with respect to FIG. 11 may be controlled by individual programmable logic controllers (PLCs). Data may be transferred back and forth from a PLC to a central computer database controller for storage. For example, a central database may be provided to store information such as gender (as well as other identified characteristics) of eggs being processed. The central computer database controller is configured to respond to individual PLCs when they request data or send data. The central computer database need not directly control the various stations under the control of respective PLCs.

Figure 12:
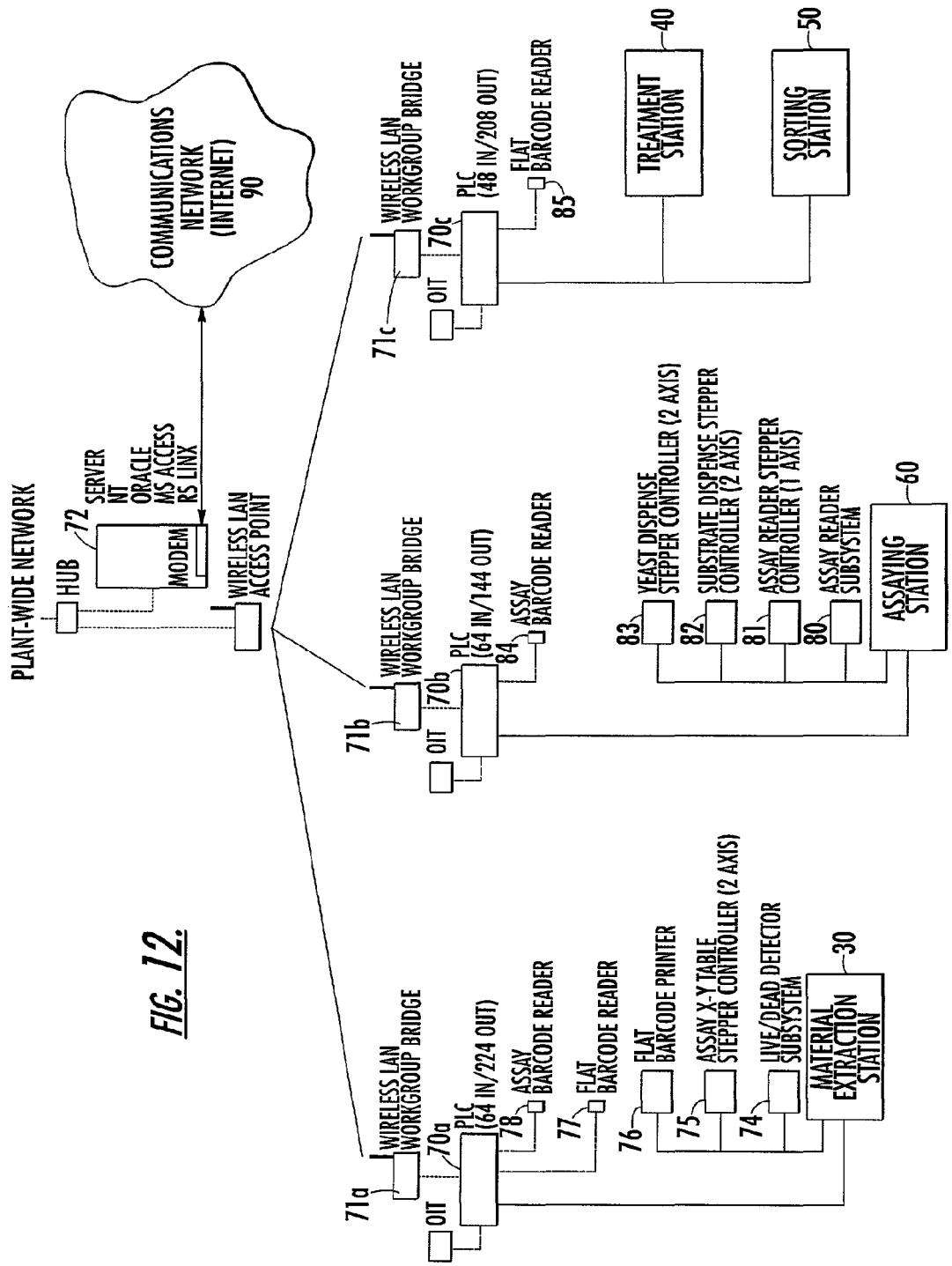
FIG. 12 is a schematic illustration of top-level controls architecture for an egg processing system according to embodiments of the present invention within a hatchery wherein individual PLCs are utilized to control a material extraction station, an assaying station, and treatment, and sorting stations, respectively.

FIG. 12 is a top-level controls architecture illustration of an embodiment of the present invention within a hatchery wherein individual PLCs are utilized to control various hatchery stations, according to embodiments of the present invention. In the illustrated embodiment, a plurality of PLCs 70a, 70b, 70c control a material extraction station 30, an assaying station 60, and treatment and sorting stations 40, 50, respectively. Each PLC 70a, 70b, 70c is connected to a server 72 via a local area network (LAN). The server 72 is in communication with a database (which can be local, remote, or a combination thereof) and stores/retrieves data to/from the database in response to requests from the individual PLCs 70a, 70b, 70c. The server 72 is capable of communicating with remote devices via a communications network, such as the Internet 90.

In the illustrated embodiment, the LAN is a wireless LAN and the PLCs 70a, 70b, 70c communicate with the server 72 via wireless LAN workgroup bridges 71a, 71b, 71c. However, it is understood that any type of LAN may be utilized, including wired LAN's. For example, FIGS. 13A-13D illustrate a wired LAN embodiment. In the illustrated embodiment, PLC 70a is configured to control a material extraction station 30 for extracting material from a plurality of eggs as described above. PLC 70a is also configured to control a live/dead detector subsystem 74 (e.g., a classifier 12, FIG. 11), an X-Y table stepper controller 75 that controls the location of a sample tray for receiving material extracted from eggs, an egg flat barcode reader 77, and an assay sample tray barcode reader 78. According to embodiments of the present invention, barcodes are utilized to track eggs within a hatchery. As such, barcodes are placed on egg flats and are read during various times during processing within a hatchery. Other embodiments include RFID (radio frequency identification) tags in lieu of barcodes and on-the-fly printed/applied identifiers either on the egg flats or on the eggs themselves.

PLC 70b is configured to control an assaying station 60 for identifying one or more characteristics of each egg as described above. PLC 70b is also configured to control an assay reader subsystem 80 (e.g., a CCD camera system that scans each sample receptacle in an assay template to determine the gender of a respective egg whose sample material is in the receptacle), an assay reader stepper controller 81, a substrate dispenser stepper controller 82, a yeast dispenser stepper controller 83, and an assay barcode reader 84. Moreover, PLC 70b may be configured to control an assaying station 60 that is directly connected to the material extraction station 30 or that is a stand-alone apparatus.

PLC 70c is configured to control a treatment station 40 and a sorting station 50 as described above. In addition, PLC 70c controls an egg flat barcode reader 85 that identifies egg flats passing through the treatment and sorting stations 40, 50.

Figure 13A:
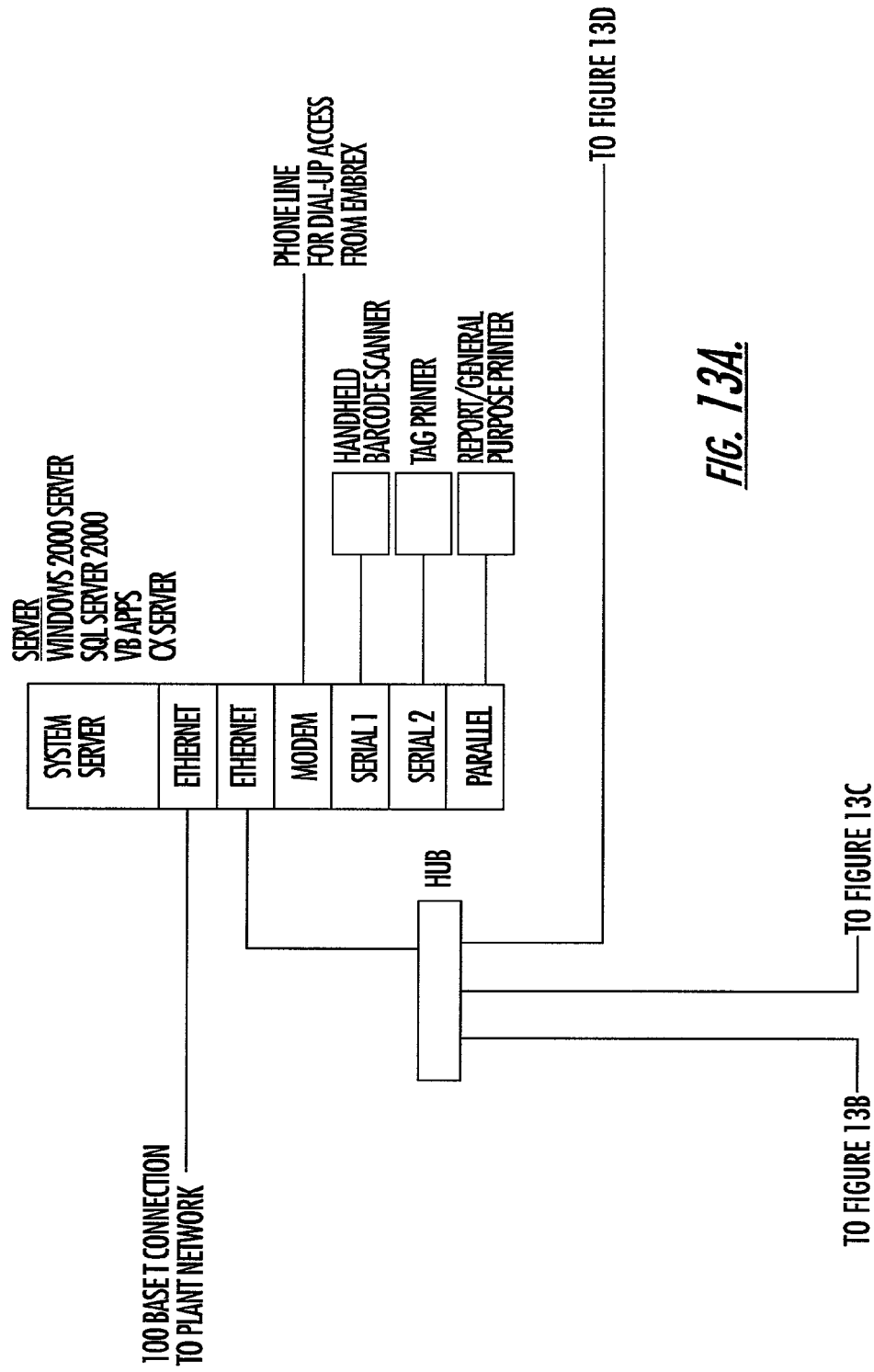
FIGS. 13A-13D are more detailed illustrations of a top-level controls architecture for an egg processing system according to embodiments of the present invention within a hatchery wherein individual PLCs are utilized to control a material extraction station (sampling module), an assaying module, and transfer module, respectively.
Figure 13B:
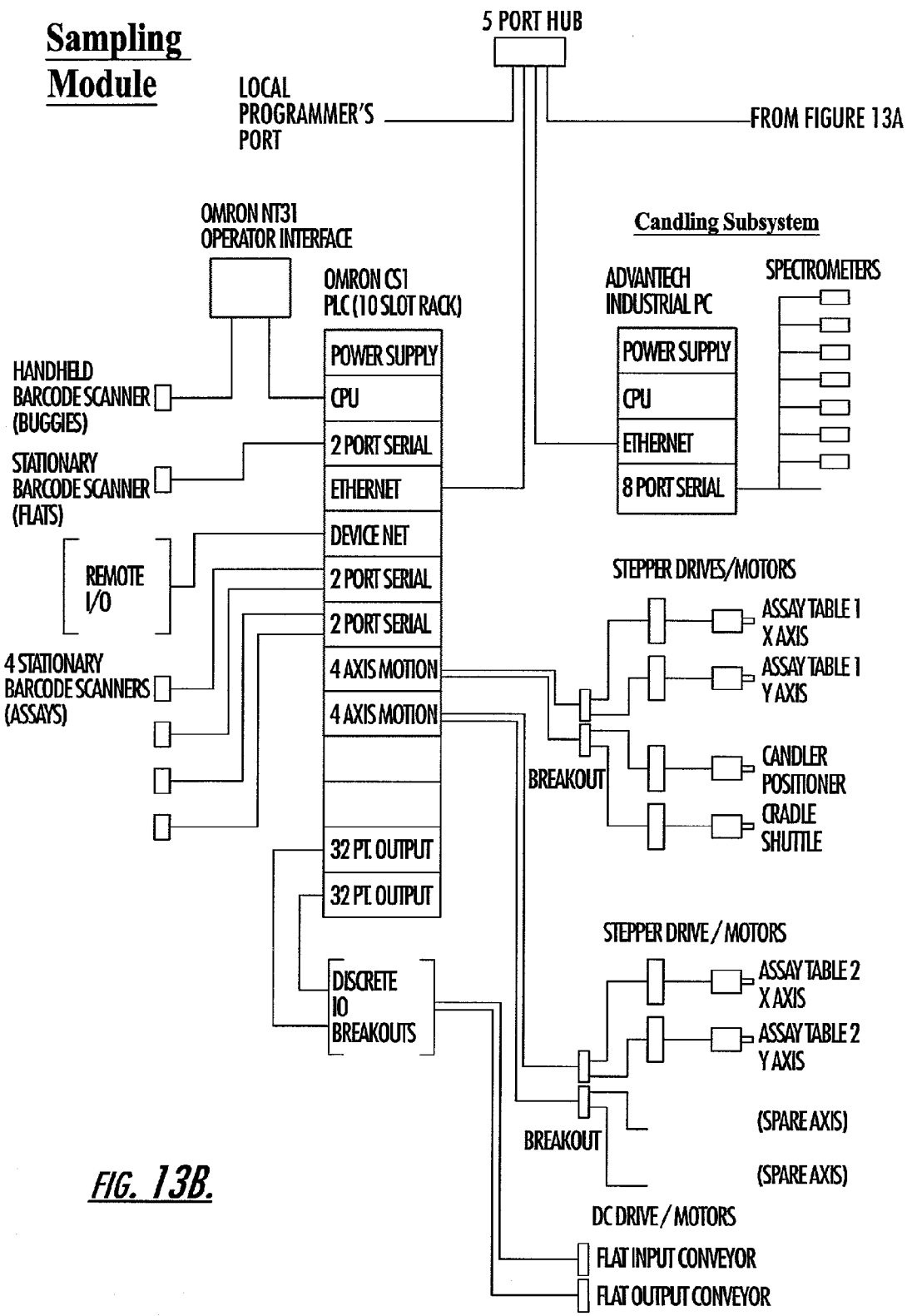
Figure 13C:
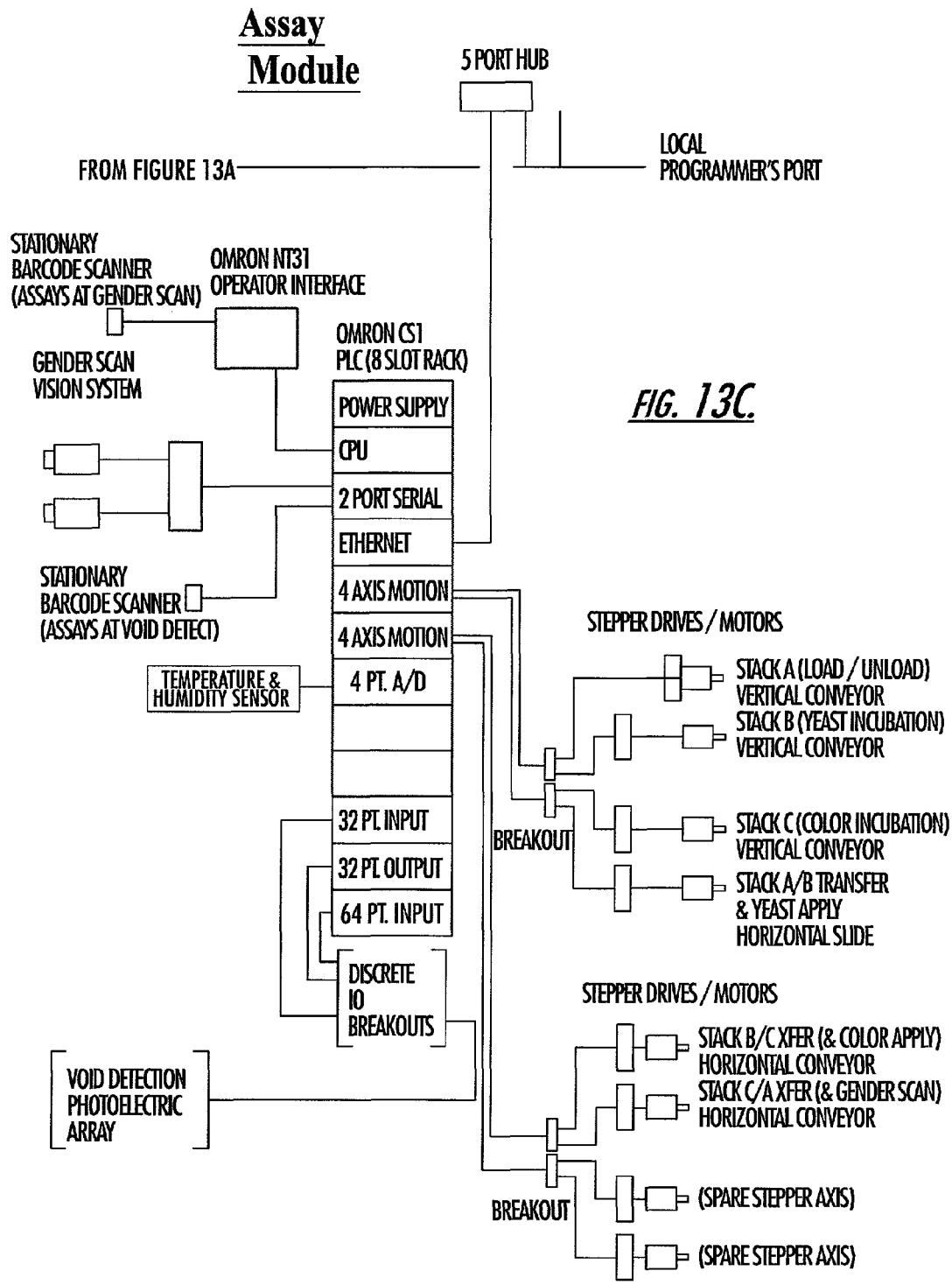
Figure 13D:
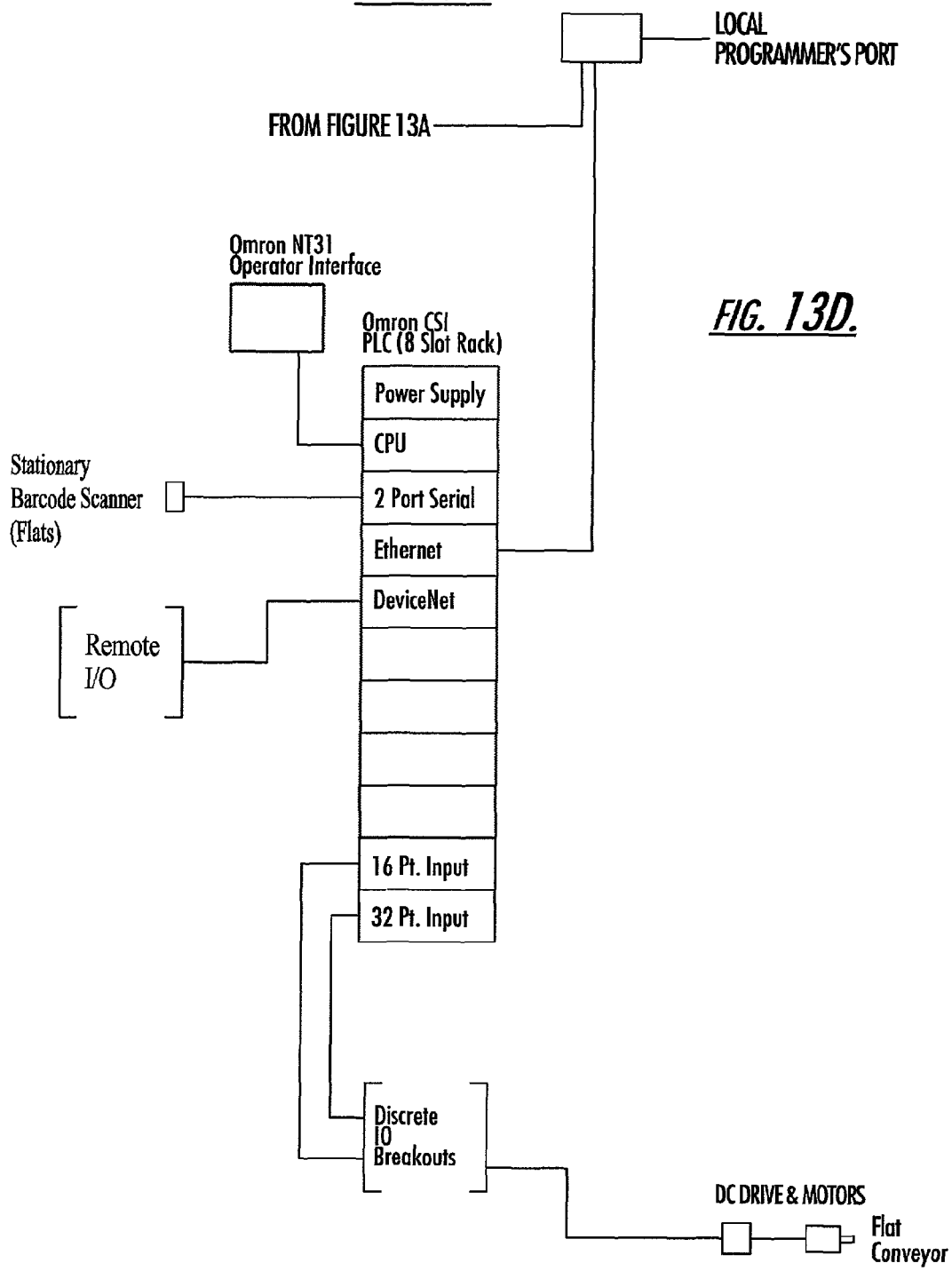

FIGS. 13A-13D are more detailed illustrations of a top-level controls architecture for an egg processing system according to embodiments of the present invention within a hatchery wherein individual PLCs are utilized to control a material extraction station (sampling module), an assaying module, and transfer module, respectively. The illustrated embodiment of FIGS. 13A-13D utilizes a wired LAN embodiment wherein a system server (FIG. 13A) communicates with (and controls) a sampling module (FIG. 13B), an assay module (FIG. 13C), and a transfer module (FIG. 13D).

Material Extraction Station

Figure 14:
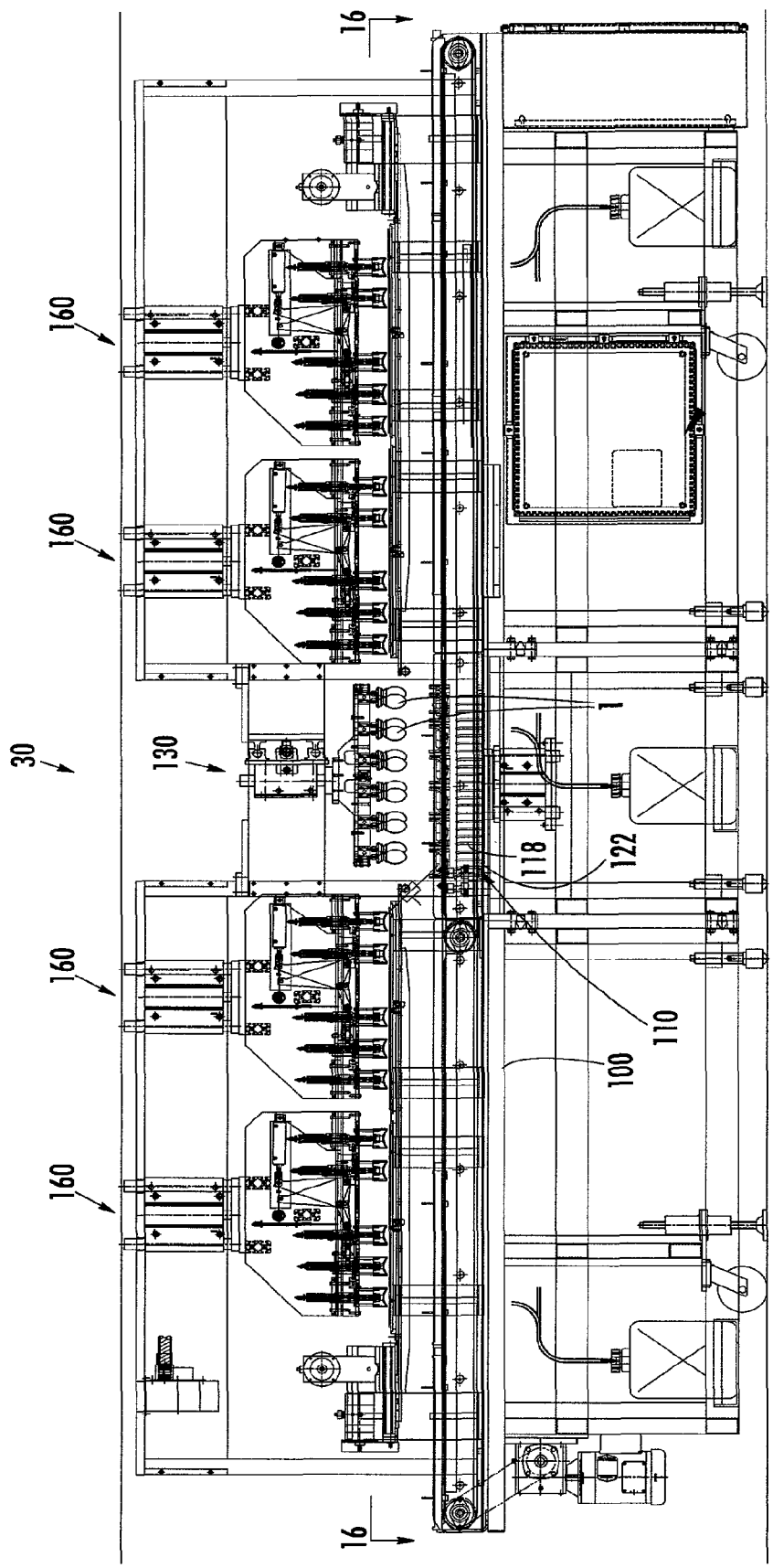
FIG. 14 is a side elevation view of an apparatus for extracting material (also referred to as a sampling module) from a plurality of eggs, according to embodiments of the present invention.
Figure 15:
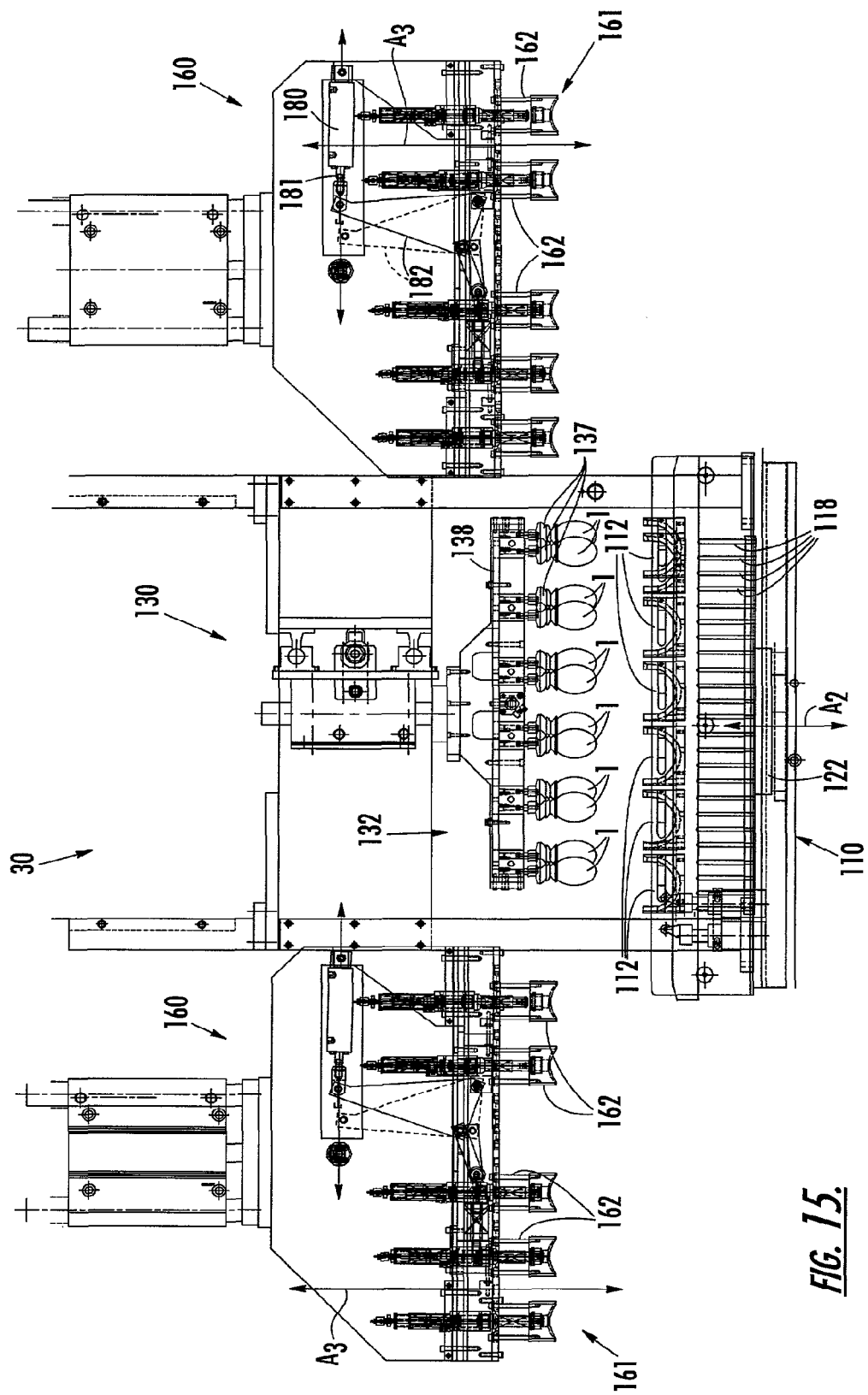
FIG. 15 is an enlarged view of the apparatus for extracting material of FIG. 14 illustrating the transfer apparatus and two sampling apparatus on opposite sides of the transfer apparatus.
Figure 16:
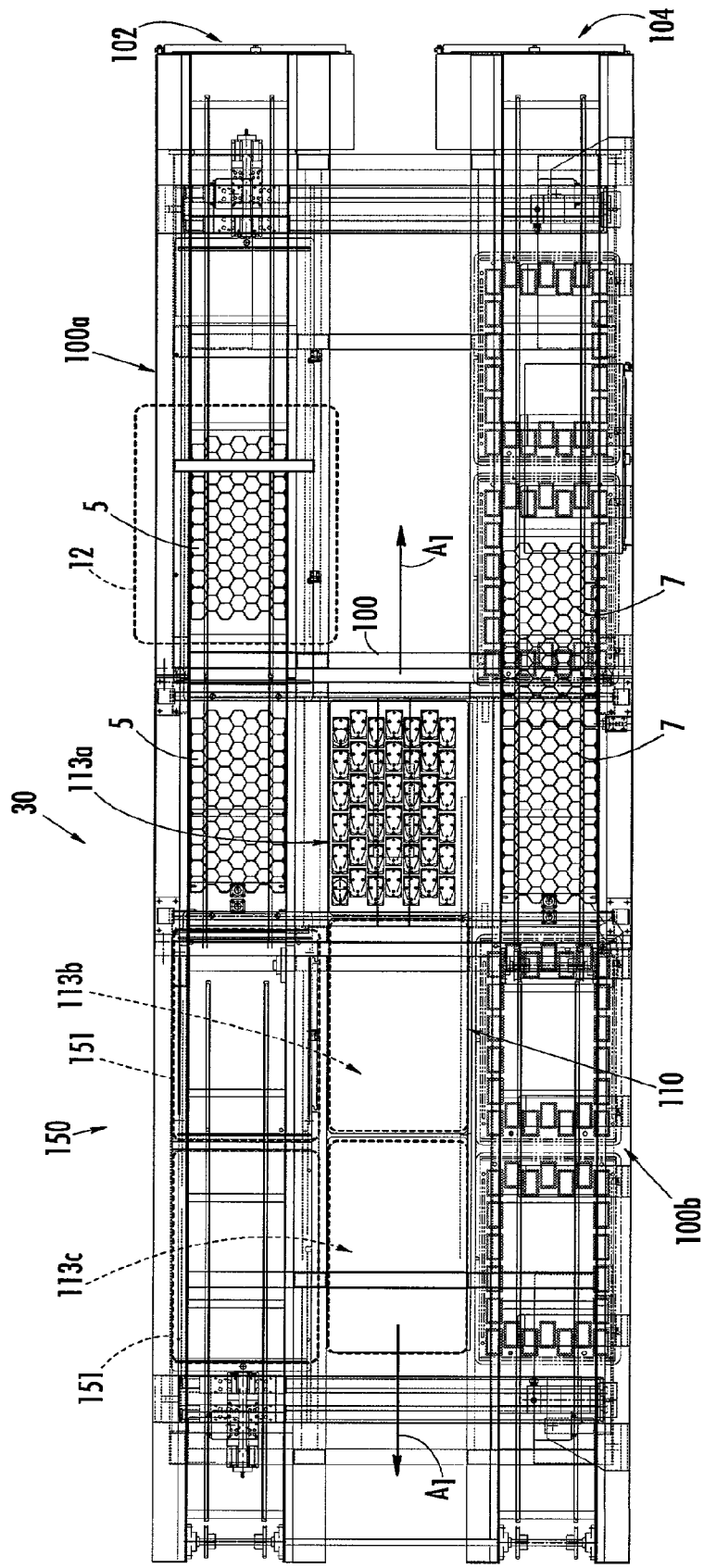
FIG. 16 is a plan view of the egg flat conveyor systems and egg cradles of the material extraction apparatus of FIG. 14 taken along lines 16-16.

Turning now to FIGS. 14-17, a material extraction station 30 for extracting material from a plurality of eggs, according to embodiments of the present invention, is illustrated. The material extraction station 30 includes a frame 100 with an incoming egg flat conveyor system 102 and an outgoing egg flat conveyor system 104 extending along respective, opposite sides 100a, 100b of the frame 100, as illustrated in FIG. 16. The material extraction station 30 also includes a classifier 12 (FIG. 16) that is configured to identify live eggs from among a plurality of eggs, an egg cradle table 110 movably mounted to the frame 100, an egg transfer apparatus 130, a sample tray handling system 150, four sets of sampling apparatus 160, and a sanitizer system (not shown), for sanitizing sampling portions of the apparatus. The incoming egg flat conveyor system 102 is configured to transport incoming flats 5 of eggs 1 through the classifier 12 and to the egg transfer apparatus 130. As will be described below, according to an embodiment of the present invention, live eggs are removed from the incoming egg flats 5. Non-live eggs remain within the incoming egg flats 5 and are carried away by the incoming egg flat conveyor system 102 for disposal or other processing. The outgoing egg flat conveyor system 104, according to an embodiment of the present invention, is configured to transport flats 7 of eggs that have had material extracted therefrom to an incubator for incubation, and/or to subsequent treatment and/or sorting stations.

Embodiments of the present invention are not limited to the removal of live eggs only from an incoming egg flat 5. For example, all eggs may be removed from an incoming egg flat 5 and placed within an array of egg cradles. Live eggs may be segregated from non-live eggs via the sorting station 50 (FIG. 11). For example, only live eggs may be transferred to hatching baskets via the sorting station 50.

The incoming egg conveyor system 102 may utilize belts and/or other conveyor system components that allow light to pass through a portion thereof to facilitate candling at the classifier 12. Egg flat conveyor systems are well known to those skilled in the art and need not be described further herein. Moreover, embodiments of the present invention are not limited to the illustrated orientation, configuration, and/or travel directions of the incoming and outgoing conveyor systems 102, 104. Incoming and outgoing egg flats may travel in various directions relative to various apparatus of the present invention, and may have various configurations and orientations.

Although eggs conventionally are carried in egg flats, any means of conveying a plurality of eggs to the classifier 12 for identifying live eggs can be used. Eggs may pass one at a time through the classifier 12 or the classifier 12 may be configured so that a number of eggs (i.e., within a flat) can pass through the classifier 12 simultaneously. Incoming and outgoing egg flats 5, 7 of virtually any type may be used in accordance with embodiments of the present invention. Flats may contain any number of rows, such as seven rows of eggs, with rows of six and seven being most common. Moreover, eggs in adjacent rows may be parallel to one another, as in a "rectangular" flat, or may be in a staggered relationship, as in an "offset" flat. Examples of suitable commercial flats include, but are not limited to, the "CHICKMASTER 54" flat, the "JAMESWAY 42" flat and the "JAMESWAY 84" flat (in each case, the number indicates the number of eggs carried by the flat). Egg flats are well known to those skilled in the art and need not be described further herein.

In addition, the egg array configuration of incoming egg flats 5 may be different from that of outgoing egg flats 7. The egg transfer apparatus 130 is configured to adjust to different egg array configurations of different egg flats, as described below.

The illustrated egg cradle table 110 includes first, second and third sets of cradles 112 arranged in adjacent respective first, second, and third arrays 113a, 113b, and 113c. The illustrated egg cradle table 110 is slidably mounted to the frame 100 between the incoming and outgoing conveyor systems 102, 104 and is movable relative to the egg transfer apparatus 130 and each of the four illustrated sampling apparatus 160 along the direction indicated by arrows $A_1$. The egg cradle table 110 is configured to move such that when one cradle array (e.g., 113a or 113b or 113c) is positioned beneath the egg transfer apparatus 130, another cradle array (e.g., 113a or 113b or 113c) is positioned beneath one of the sampling apparatus 160, as will be described in detail below.

Although illustrated with three cradle arrays 113a, 113b, 113c and four sampling apparatus 160, an apparatus for extracting material from eggs according to embodiments of the present invention may have one or more arrays of cradles 112 and one or more sampling apparatus 160. For example, an apparatus for extracting material from eggs according to embodiments of the present invention may have a single array of cradles 112 and a single sampling apparatus 160.

Referring now to FIG. 15, lifting head 132 of the illustrated transfer apparatus 130 and two of the sampling apparatus 160 of FIG. 14 on opposite sides of the transfer apparatus 130 are illustrated in enlarged detail. The illustrated lifting head 132 includes an expandable and collapsible array of manifold blocks and vacuum cups 137 that are supported by a generally rectangular frame 138. The lifting head 132 is configured to lift a plurality of eggs from an array of cradles 112 and place the eggs within outgoing egg flats 7.

The illustrated egg cradle table 110 includes a plurality of elongated rods 118 that are simultaneously controlled by an actuator device 122 which moves the elongated rods 118 between retracted and extended positions (indicated by arrow $A_2$) within respective cradles 112 to reposition eggs from horizontal to vertical positions, as will be described below. Each sampling apparatus 160 includes an array of sampling heads 162 that are configured to extract material from a respective egg positioned within an egg cradle 112. Each sampling head is configured for generally vertical movement (indicated by arrows $A_3$) relative to the egg cradle table 110, as will be described below.

Figure 18A:
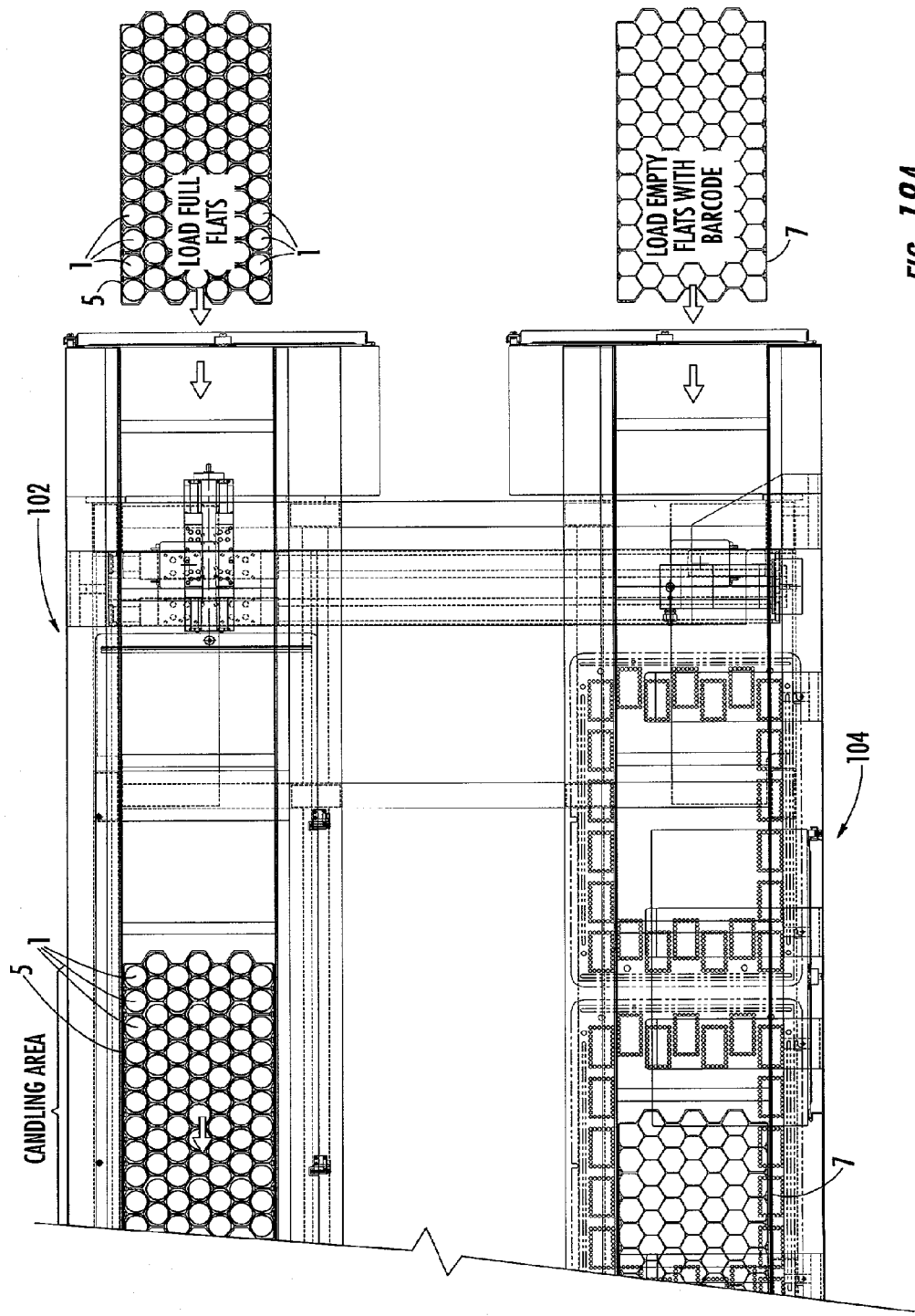
FIG. 18A illustrates the loading of incoming egg flats onto the incoming egg flat conveyor system and the loading of empty egg flats onto the outgoing egg flat conveyor system.

FIG. 17 is a side elevation view of the material extraction apparatus of FIG. 14 illustrating the two lifting heads 132, 134 of the egg transfer apparatus 130. As illustrated, the lifting heads 132, 134 are configured for lateral movement (indicated by arrows $A_4$) between the incoming and outgoing egg flat conveyor systems 102, 104 and the egg cradle table 110. FIGS. 18A-18D illustrate the progression of eggs through the material extraction station 30. FIG. 18A illustrates the loading of incoming egg flats 5 which contain a plurality of eggs 1 onto the incoming egg flat conveyor system 102, and the loading of empty egg flats 7 onto the outgoing egg flat conveyor system 104. FIG. 18A also illustrates an incoming egg flat 5 containing a plurality of eggs 1 positioned within the candling area (i.e., beneath the classifier 12 illustrated in FIG. 16) of the material extraction apparatus 30.

Figure 18B:
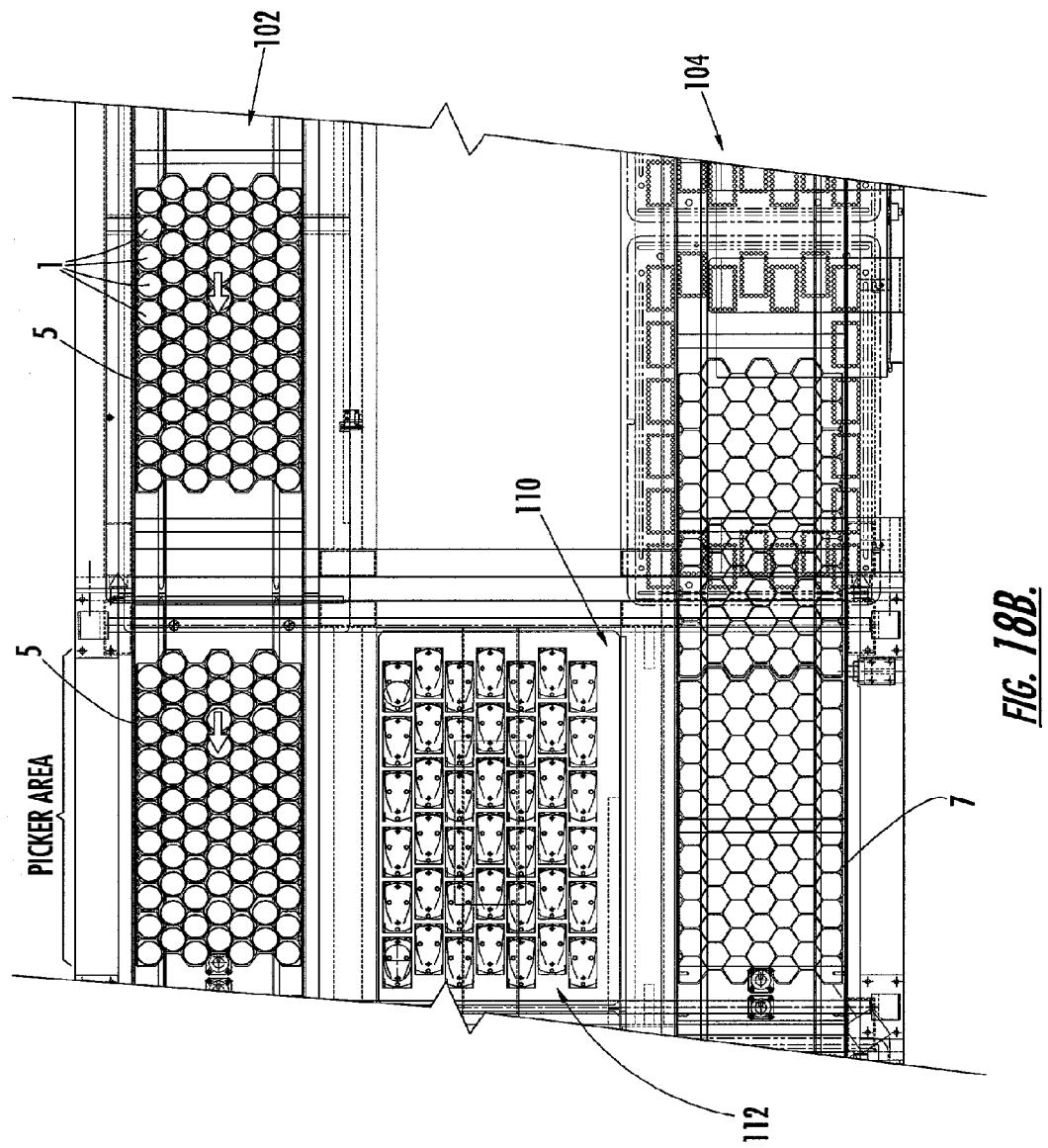
FIG. 18B illustrates movement of incoming egg flats along the incoming egg flat conveyor system to the picker area where the egg transfer apparatus transfers eggs from incoming egg flats to the egg cradles.

FIG. 18B illustrates movement of an incoming egg flat 5 along the incoming egg flat conveyor system from the candling area to the picker area. In the picker area, egg transfer head 134 is configured to pick up a plurality of the eggs 1 from an egg flat 5 and place the eggs 1 within an array of cradles 112 on the slidable egg cradle table 110. An empty outgoing egg flat 7 is positioned adjacent the array of cradles 112.

FIG. 18C illustrates a plurality of eggs 1 seated within the plurality of egg cradles 112 after being transferred from an incoming egg flat 5. For ease of illustration, the eggs 1 are illustrated in a generally vertical orientation within the egg cradles 112. However, as will be described below, the eggs 1 are repositioned to a generally horizontal orientation by the egg cradles 112 prior to removing material from the eggs 1. The egg cradles 112 are also configured to reposition the eggs after material has been removed therefrom to a generally vertical orientation prior to being transferred to an outgoing egg flat 7.

The eggs 1' from which material has been extracted are transferred to an outgoing egg flat 7. An outgoing flat 7 into which eggs just sampled may thereupon be placed in an incubator for incubation according to conventional procedures while awaiting results from the assaying station 60 (FIG. 11). When assaying results are completed, and characteristics of each egg identified (e.g., gender) the eggs may be moved from the incubator to one or more treatments stations 40 (FIG. 11) and/or to a sorting station 50 (FIG. 11). According to embodiments of the present invention described below, an assaying station 60 may be connected to the material extraction station 30 and may be configured to assay material extracted from eggs quickly. As such, flats of eggs from which material has been extracted may be held in one or more accumulation modules instead of being returned to incubators prior to being transported to a treatment/sorting station(s).

Figure 18D:
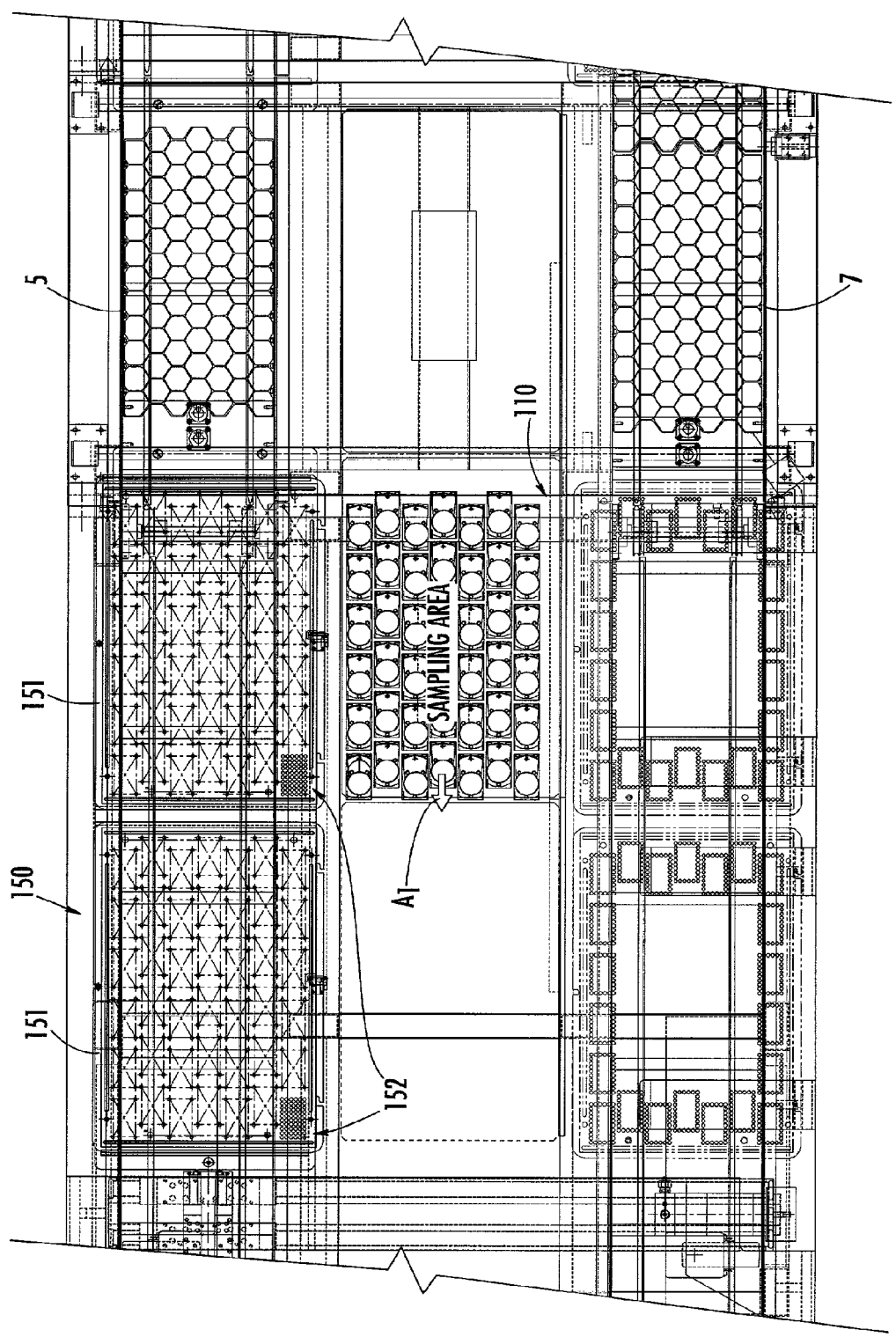
FIG. 18D illustrates movement of the egg cradles to a location where a sampling apparatus is configured to extract material from the eggs positioned within the egg cradles.

FIG. 18D illustrates movement of the egg cradle table 110 in the direction indicated by arrow $A_1$ to a location where the array of egg cradles 112 containing eggs 1 is positioned beneath one of the sampling apparatus 160 (FIG. 14).

Figure 19:
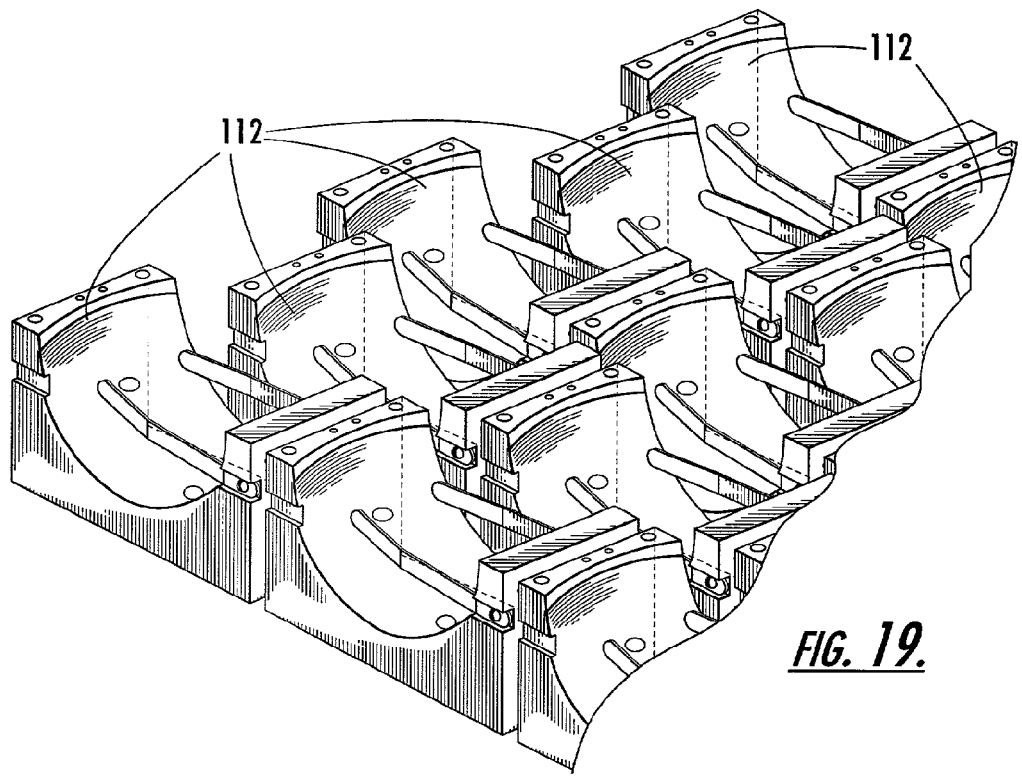
FIG. 19 is a perspective view of a portion of an array of egg cradles configured to receive eggs in a generally vertical orientation and to cause the eggs to move to a generally horizontal orientation, according to embodiments of the present invention.

FIG. 19 illustrates a portion of an exemplary array of cradles 112 that can be included on the illustrated egg cradle table 110. Each cradle 112 is configured to receive an egg in a generally vertical orientation and to cause the egg to move to a generally horizontal and centered orientation.

Figure 20:
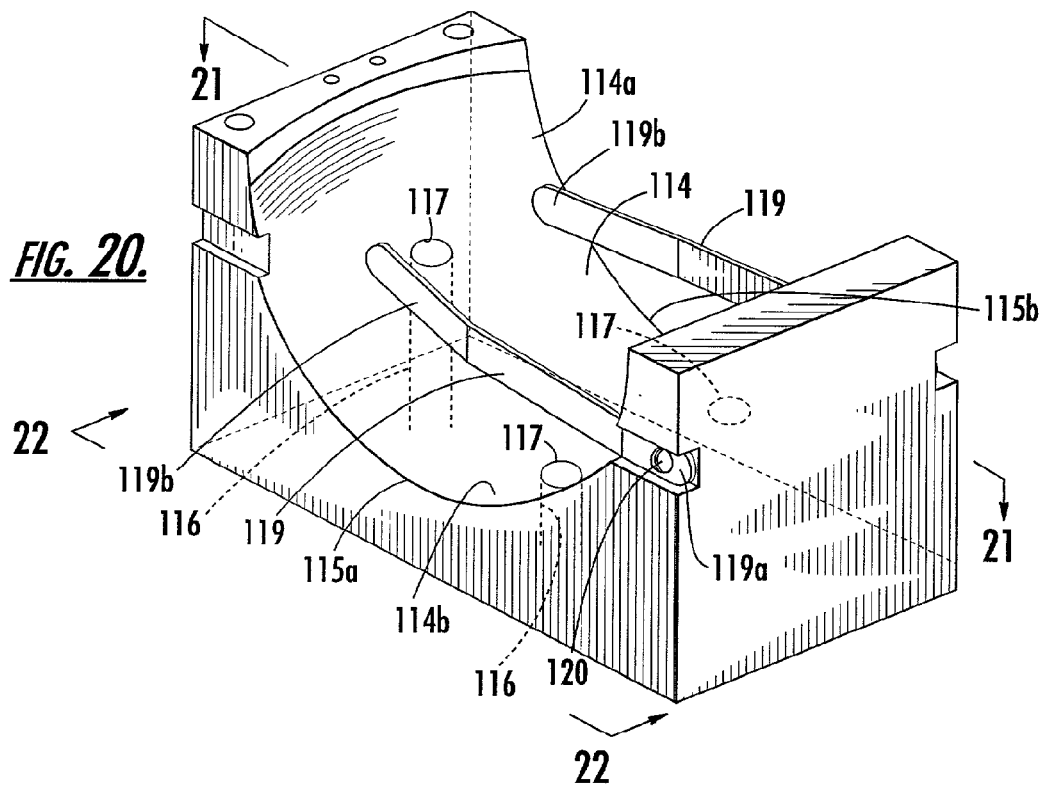
FIG. 20 is an enlarged perspective view of a cradle in the array of FIG. 19.

An enlarged perspective view of a cradle 112 in the illustrated partial array of FIG. 19 is illustrated in FIG. 20 and is representative of each cradle in the partial array. The illustrated cradle 112 includes an inclined, arcuate surface 114 that defines a receptacle for receiving an egg. The illustrated arcuate surface 114 of the cradle 112 has an inclined upper portion 114a, a lower portion (or floor) 114b, and opposite side portions 115a, 115b.

The cradle arcuate surface 114 may have a generally concave configuration between opposite side portions 115a, 115b. The generally concave configuration of the arcuate surface 114 helps maintain an egg in a generally centered position on the arcuate surface 114.

The arcuate surface upper portion 114a is configured to receive an end of a vertically oriented egg and to cause the egg to slide to the arcuate surface lower portion 114b such that the egg becomes positioned on the arcuate surface lower portion 114b in a generally inclined orientation.

Embodiments of the present invention are not limited to the illustrated cradle 112 or to the illustrated configuration of the arcuate surface 114. The arcuate surface 114 of the cradle 112 may be a substantially smooth, continuous arcuate surface. Alternatively, the arcuate surface 114 may include a plurality of flat, adjacent surfaces arranged so as to form a generally arcuate configuration. In addition, the cradle arcuate surface may have a generally flat configuration between opposite side portions 115a, 115b.

Egg cradles that are configured to receive an egg in a generally vertical orientation, to cause the egg to move to a generally horizontal orientation, and to reorient the egg to a generally vertical orientation for removal are described in detail in co-assigned U.S. patent application Ser. No. 09/835, 990 entitled, Apparatus and Method for Reorienting an Egg Between Vertical and Horizontal Orientations, which is incorporated herein by reference in its entirety.

Each illustrated cradle 112 also includes a pair of elongated retaining arms 119 secured to the cradle 112 in spaced-apart relation along the respective arcuate surface side portions 115a, 115b, as illustrated. Each of the illustrated elongated arms 119 has a respective end 119a that is secured to the cradle 112 via fasteners 120 and an opposite free end 119b. Fasteners 120 may be various known fastening devices including, but not limited to, threaded fasteners (e.g., screws, bolts, etc.) and unthreaded fasteners (e.g., rivets, tapered studs, untapered studs, etc.). Alternatively, retaining arms 119 may be adhesively secured to a cradle 112, or secured to a cradle 112 via welding, brazing, soldering, or various other known methods.

Figure 21:
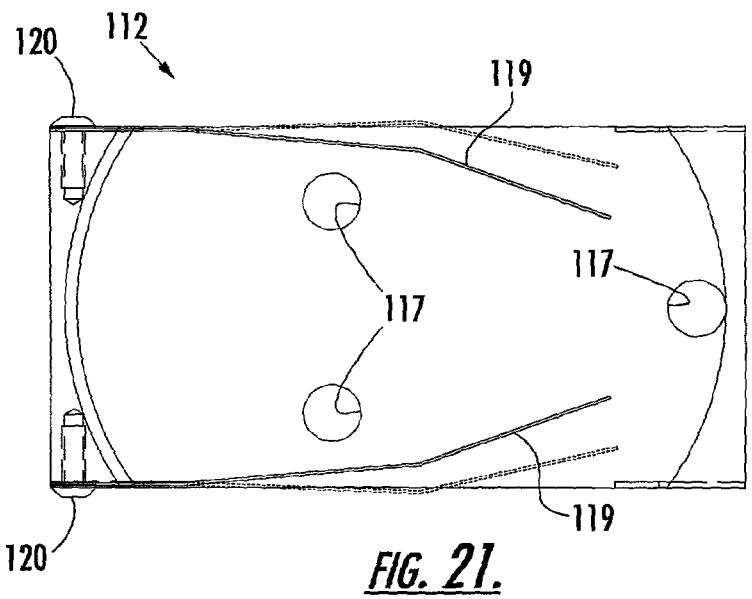
FIG. 21 is a top plan view of the egg cradle of FIG. 20 taken along lines 21-21.

The retaining arms 119 help to prevent an egg from rolling or falling off of a cradle arcuate surface 114. Moreover, the retaining arms 119 help stabilize an egg that is being repositioned from a generally horizontal position to a generally vertical position, as described below. The retaining arms 119 are configured to flex outwardly, as illustrated in FIG. 21, to accommodate large eggs, while at the same time providing support for narrow eggs. In addition, the retaining arms 119 help to center an egg laterally on the cradle arcuate surface 114 so that the long axis of the egg is aligned with the long axis of the cradle while the egg is in a generally horizontal position.

Embodiments of the present invention are not limited to the illustrated retaining arms 119. Retaining arms may have various configurations and may be attached is to a cradle 112 in various locations and configurations. Moreover, embodiments of the present invention may not require retaining arms.

Figure 22:
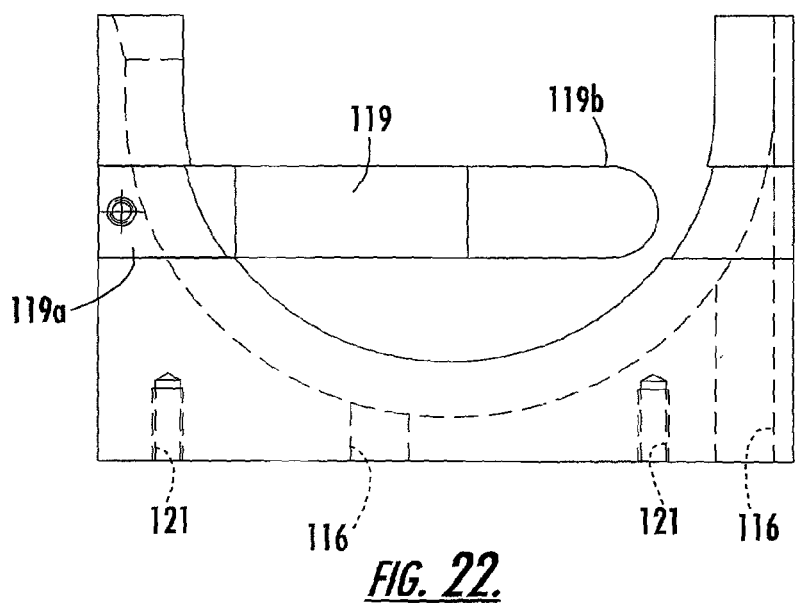
FIG. 22 is a side elevation view of the egg cradle of FIG. 20 taken along lines 22-22.
Figure 25:
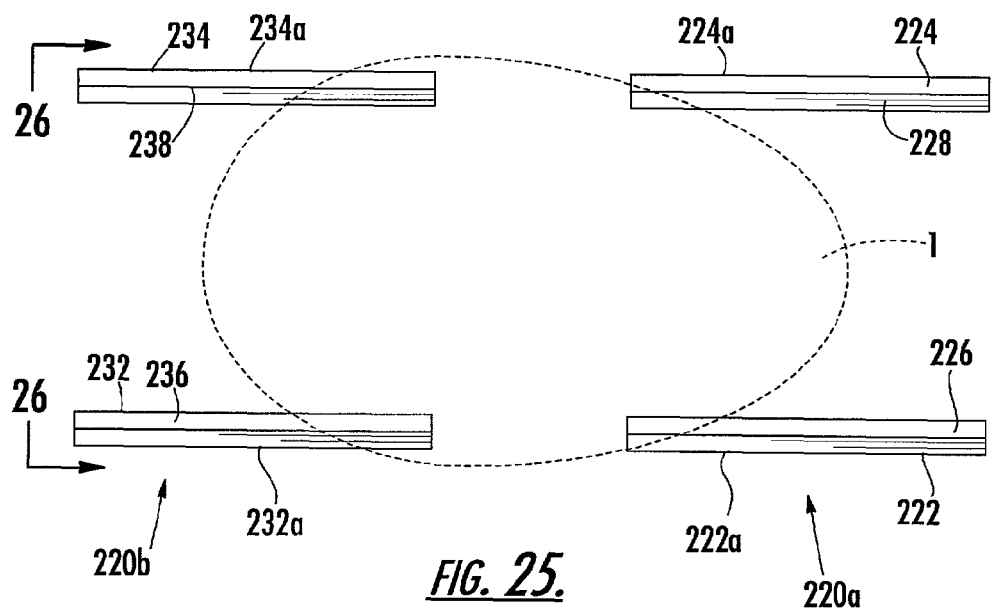
FIG. 25 is a partial top plan view of the egg positioning apparatus of FIG. 23 taken along lines 25-25 and illustrating the inclined upper ends of the first and second portions.
Figure 26:
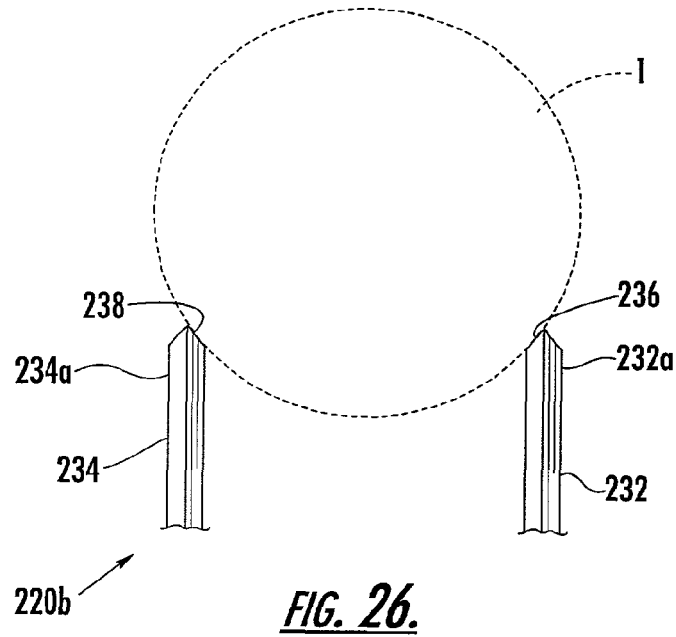
FIG. 26 is a partial end view of the egg positioning apparatus of FIG. 25 taken along lines 26-26.

Each cradle 112 is secured to the cradle table 110 via fastening devices including, but not limited to, threaded fasteners (e.g., screws, bolts, etc.) and unthreaded fasteners (e.g., rivets, tapered studs, untapered studs, etc.). Alternatively, each cradle 112 may be adhesively secured to the cradle table 110, or secured to the cradle table 110 via welding, brazing, soldering, or various other known methods. FIG. 22 illustrates threaded passageways 121 in a cradle 112 that are configured to threadingly engage respective threaded fastening members (not shown) for securing a cradle 112 to the cradle table 110 according to embodiments of the present invention.

A plurality of passageways 116 extend through each cradle 112 and terminate at respective apertures 117 in the arcuate surface 114 as illustrated. An elongated rod 118, which serves as an orientation member, is configured for reciprocal movement between a retracted position and an extended position within each passageway 116. In an extended position, the elongated rods 118 for each cradle 112 urge an egg horizontally positioned (or otherwise inclined relative to vertical) on the arcuate surface lower portion 114b to a vertical orientation so that the egg can be removed from the cradle 112 via the egg transfer apparatus 130.

Embodiments of the present invention are not limited to the illustrated elongated rods 118 or to the orientation of the elongated rods 118 with respect to each cradle 112. Orientation members may have various configurations and may be positioned within a cradle 112 for reciprocal movement between retracted and extended positions in various ways and in various orientations.

As illustrated in FIG. 15, the elongated rods 118 are arranged in an array and are simultaneously controlled by an actuator device 122 which moves the elongated rods 118 between retracted and extended positions within respective cradles 112. When the array of rods 118 are in a retracted position, eggs within the cradles 112 have a generally horizontal orientation as described above. When the rods 118 are moved to an extended position, the rods extend upwardly through the cradles as described above and cause the eggs to move to a generally vertical orientation. The actuator 122 for moving the rods 118 between retracted and extended positions may be operated pneumatically, hydraulically, magnetically, and/or electromechanical actuators may be utilized.

FIGS. 23-26 illustrate an egg cradle 212 that may be utilized in accordance with other embodiments of the present invention and that is configured to reposition an egg from a vertically oriented position to a horizontal position and then back to a vertically oriented position, according to an alternative embodiment of the present invention. The illustrated cradle 212 has first and second portions 220a, 220b that define a receptacle for receiving an egg. The illustrated first portion 220a has a pair of opposite, spaced-apart members 222, 224 with inclined upper ends 222a, 224a. Each inclined upper end 222a, 224a has an inwardly sloping surface 226, 228. The illustrated second portion 220b has a pair of opposite, spaced-apart members 232, 234 with inclined upper ends 232a, 234a. Each inclined upper end 232a, 234a has an inwardly sloping surface 236, 238.

The inclined upper ends 232a, 234a of the second portion 220b are configured to receive an end of a vertically oriented egg and to cause the egg to slide downwardly such that the egg becomes positioned on the first and second portions 220a, 220b in a generally inclined orientation. The configuration of the inclined upper ends 222a, 224a, 232a, 234a of the first and second portions 220a, 220b help maintain an egg in a generally centered position in the cradle 212.

The second portion 220b serves as an orientation member and is configured for reciprocal movement between a retracted position (FIG. 23) and an extended position (FIG. 24). In an extended position, the second portion 220b urges an egg horizontally positioned (or otherwise inclined relative to vertical) within the cradle 212 to a vertical orientation.

As illustrated in FIG. 17, the egg transfer apparatus 130 of the material extraction station 30 of FIG. 14 includes first and second, adjacent lifting heads 132, 134 which operate in tandem. The first lifting head 134 is configured to simultaneously lift a plurality of generally vertically oriented eggs 1 from an incoming egg flat 5 on the incoming egg flat conveyor system 102 and place the plurality of eggs 1 within a first array of cradles 112. Eggs are typically positioned within an incoming egg flat with the large end of the egg facing in a generally upward direction. The first lifting head 134 can be controlled to pick up selected eggs 1 from an incoming egg flat 5. For example, the first lifting head 134 can be directed to only pick up live eggs, as identified by the classifier 12.

The adjacent second lifting head 132 is configured to simultaneously lift and remove a plurality of eggs 1 from a plurality of cradles 112 on the egg cradle table 110 and place the eggs 1 within an outgoing egg flat 7 on the outgoing egg flat conveyor system 104. The eggs 1 are reoriented to a generally vertical orientation to facilitate removal from the cradles 112. Eggs are typically placed within an outgoing egg flat 7 with the large end in a generally upward direction.

The illustrated egg cradle table 110 is slidably mounted to the frame 100, and is and movable relative to the first and second lifting heads 134, 132 such that the first, second, or third arrays 113a, 113b, 113c of egg cradles 112 can be positioned beneath the egg transfer device 130 at any given time so that the lifting heads 132, 134 can place/remove eggs within/from the cradles 112 as described above.

The slidable configuration of the egg cradle table 110 allows one array of cradles to receive eggs from one of the lifting heads 132, 134 while another array of cradles is positioned beneath a respective sampling apparatus 160 such that material can be extracted from the eggs, as will be described below. The use of multiple arrays of egg cradles along with reciprocal motion of the egg cradle table facilitates processing throughput.

Figure 27:
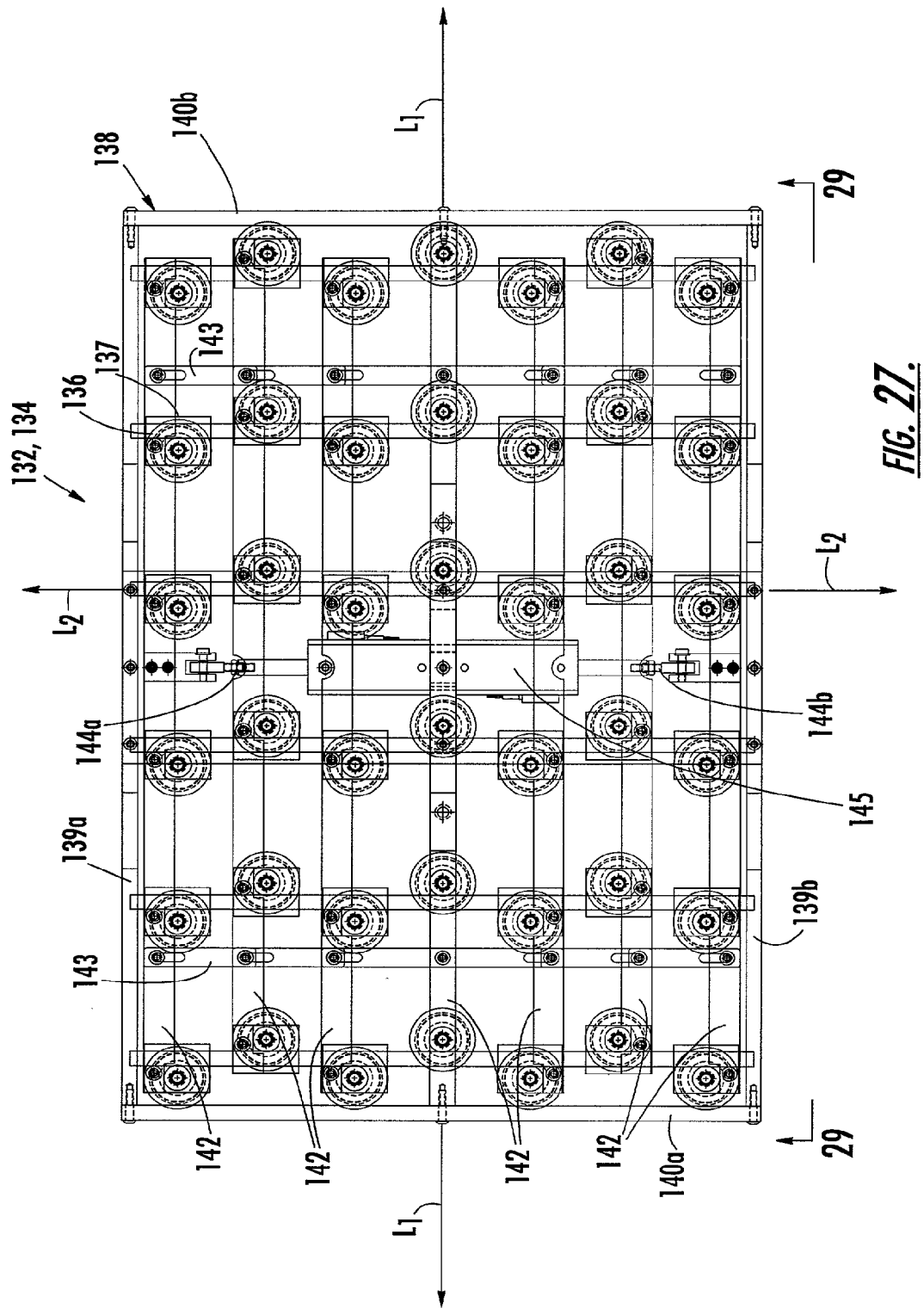
FIG. 27 is a top plan view of a lifting head of the egg transfer apparatus of FIG. 14 illustrating an array of manifold blocks and vacuum cups, wherein the array is in an expanded configuration.
Figure 28:
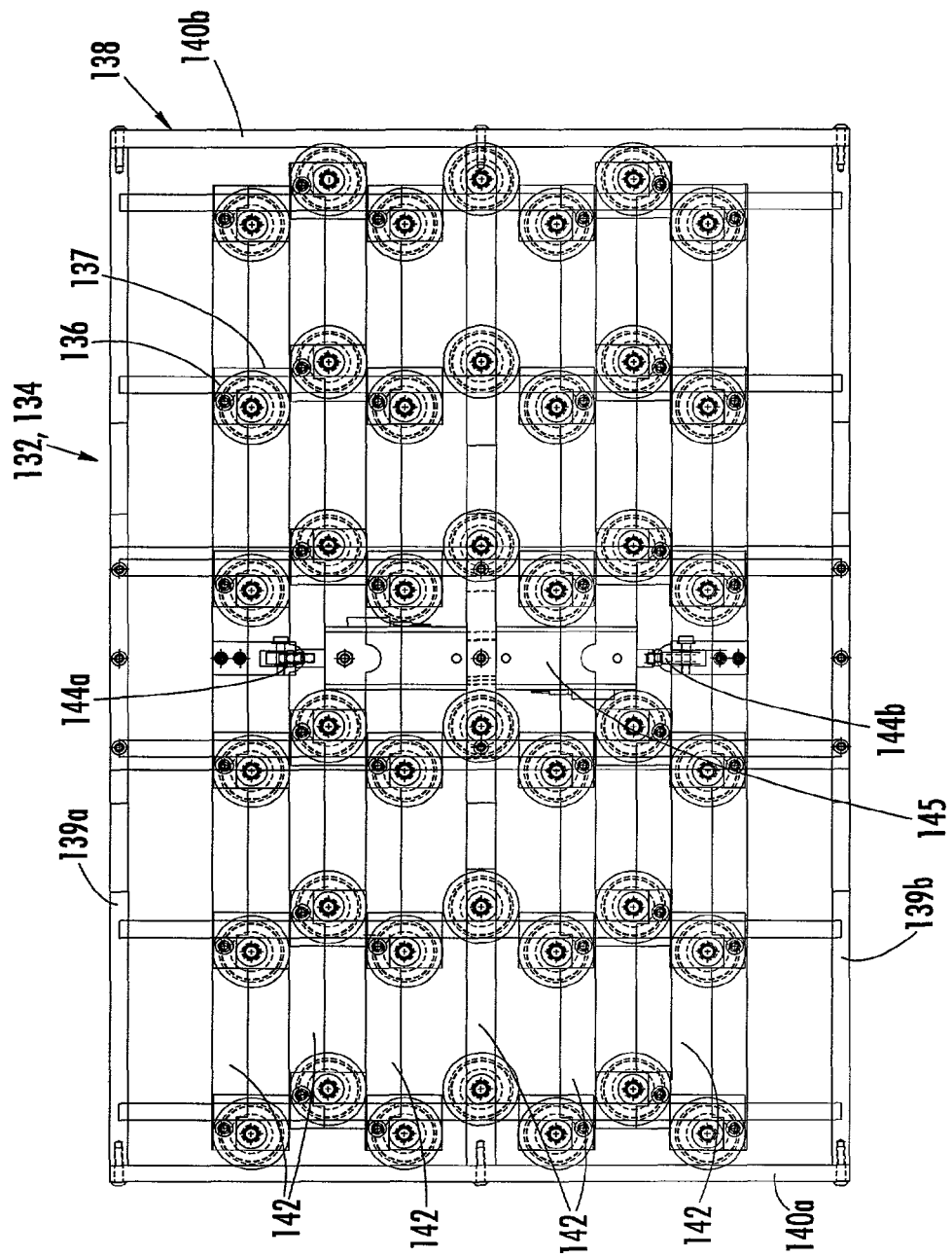
FIG. 28 is a top plan view of the lifting head of FIG. 27, and wherein the array of manifold blocks and vacuum cups is contracted along a first direction.
Figure 29:
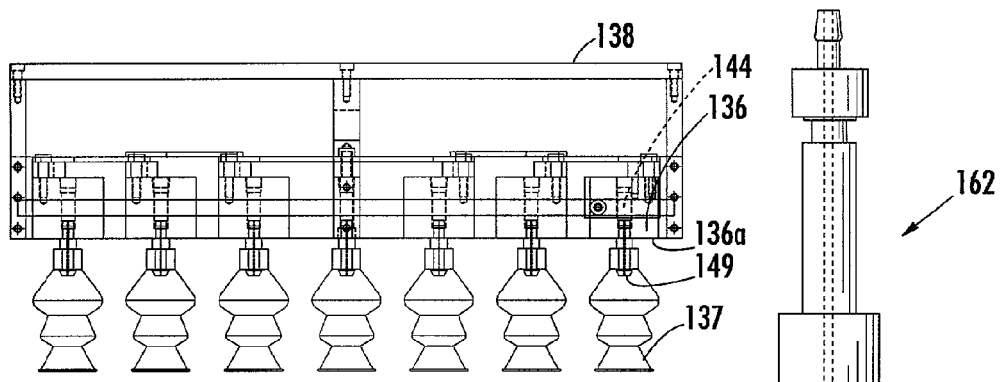
FIG. 29 is a side elevation view of the lifting head of FIG. 27 taken along lines 29-29.

Referring to FIGS. 27-29, each lifting head 132, 134 of the illustrated egg transfer apparatus 130 includes an expandable and collapsible array of manifold blocks 136 and vacuum cups 137 that are supported by a generally rectangular frame 138. The illustrated frame 138 includes opposite side members 139a, 139b that extend along a first direction $L_1$ and opposite end members 140a, 140b that extend along a second direction $L_2$ that is substantially perpendicular to $L_1$.

Each manifold block 136 and vacuum cup 137 is supported from a respective cross rail 142 that extends between the side members 140a, 140b, as illustrated. A middle one of the cross rails is fixed between the side members 140a, 140b. The cross rails 142 on either side of the fixed middle cross rail are slidably supported by the frame 138 and are configured to move along the second direction $L_2$. Adjacent cross rails 142 are connected via a pair of restraining members 143.

Actuator members 144a, 144b are connected to rails 142 as illustrated and are used to collapse and expand the array of manifold blocks 136 and vacuum cups 137 along the second direction $L_2$. Each of the actuator members 144a, 144b are controlled by an actuator device 145 which is in communication with a controller (e.g., PLC 70a of FIG. 12). The actuator 145 may be operated pneumatically, hydraulically, magnetically, and/or electromechanical actuators may be utilized.

FIG. 27 illustrates the array of manifold blocks 136 and vacuum cups 137 in an expanded configuration and FIG. 28 illustrates the array of manifold blocks 136 and vacuum cups 137 in a contracted configuration. In FIG. 28, the restraining members 143 are not shown for clarity. The expandable and contractible nature of the array of manifold blocks 136 and vacuum cups 137 for each lifting head 132, 134 allows a plurality (or "clutch") of eggs to be lifted from, and inserted into, egg flat and egg cradle arrays of different sizes and configurations.

According to embodiments of the present invention, the array of manifold blocks 136 and vacuum cups 137 may be expandable and contractible in two directions. For example, a particular style of incoming egg flat may allow one inch (1") between adjacent eggs on a row, and one inch (1") between adjacent rows. An array of egg cradles 112 in the egg cradle table 110 may have a different configuration. For example, an array of egg cradles may allow only one-half inch (0.5") between adjacent eggs on a row, and one and one-half inches (1.5") between adjacent rows. Similarly, an outgoing egg flat may have a different array configuration from an egg cradle array configuration. An array that is expandable and contractible in two directions can accommodate such differences in egg flat and cradle arrays.

Figure 30:
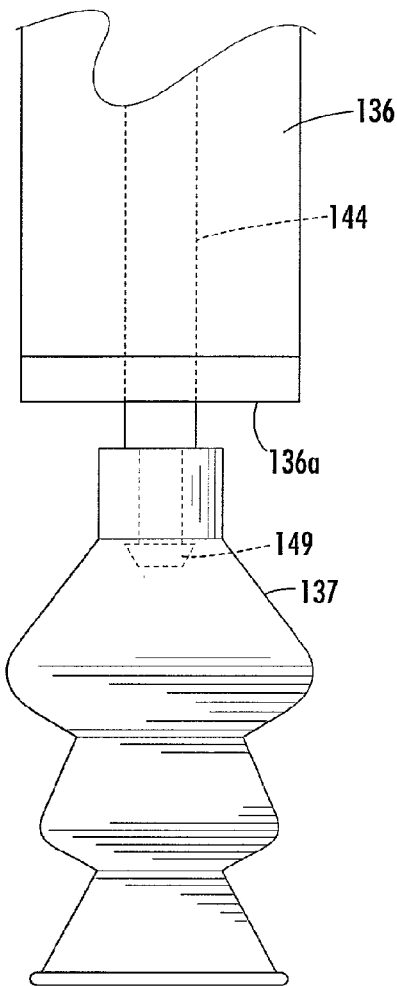
FIG. 30 is an enlarged side view of one of the flexible cups of the lifting head of FIG. 27 that is configured to transfer a respective egg according to embodiments of the present invention.

The array configuration of each lifting head 132, 134 is adjustable via a controller, such as a central controller (PLC) or a dedicated controller (PLC) (e.g., PLC 70a of FIG. 12) so that eggs can be transferred among egg flats and cradles having different sizes and/or array configurations. Each lifting head 132, 134 is also preferably easily removable as a unit to facilitate cleaning Referring now to FIG. 30, each manifold block 136 includes an end portion 136a and an internal passageway 144 that terminates at a nozzle 149 extending from the end portion 136a. The internal passageway 144 of each manifold block 136 is in fluid communication with a vacuum source (not shown) and an air source via respective vacuum and air lines connected to respective fittings on top of each manifold block 136, as would be understood to those skilled in the art. Preferably, each manifold block 136 and vacuum cup 137 is in fluid communication with a separate vacuum supply to allow for selective transfer of eggs.

A flexible vacuum cup 137 is secured to each respective manifold block nozzle 149. Each flexible vacuum cup 137 is configured to engage and retain an egg in seated relation therewith when vacuum is provided within the flexible cup 137 via a respective internal passageway 144 and to release a respective egg when vacuum within the respective internal passageway 144 is destroyed. Air from an air source may be provided within the internal passageway 144 to facilitate removal of eggs from the flexible vacuum cup 137.

Figure 40:
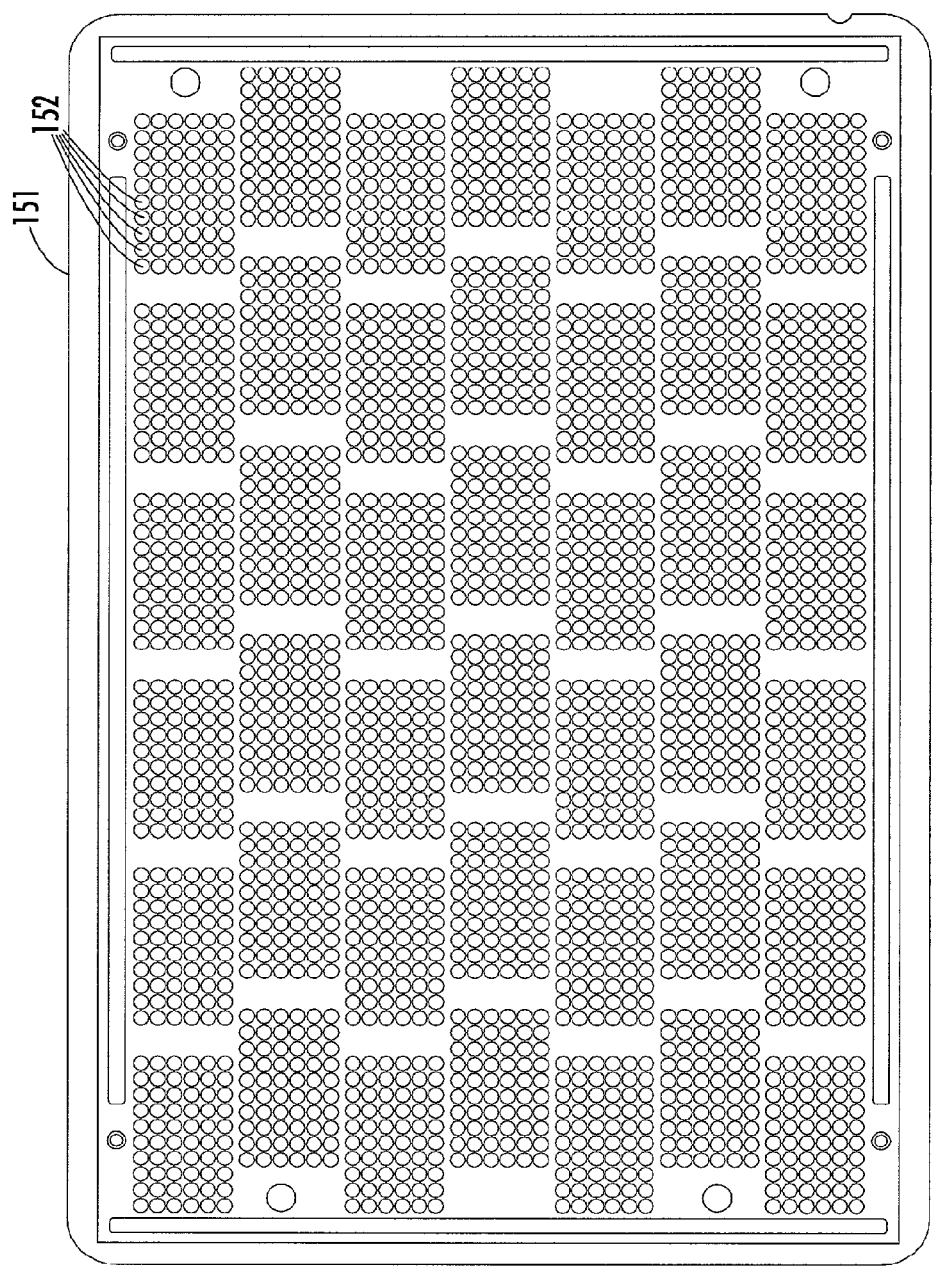
FIG. 40 is a plan view of a sample tray having a plurality of sample receptacles configured to receive material extracted from eggs according to embodiments of the present invention.

Lifting heads 132, 134 of the egg transfer apparatus 130 may utilize various suction-type lifting devices. Moreover, any suitable means for transferring eggs from a flat to an array of egg cradles, and from the array of egg cradles to a flat, may be utilized in accordance with embodiments of the present invention. Each sampling apparatus 160 of the material extraction apparatus 30 of FIG. 14 includes an array or set 161 of sample heads 162. Each sample head 162 is configured to extract material from an egg and deposit the extracted material within a respective sample receptacle 152 in a sample tray 150 (FIG. 40). Each sampling apparatus 160 in the illustrated embodiment of FIG. 14 are fixed and the cradle table 110 moves relative thereto as described above. Accordingly, when a set of cradles 112 containing eggs 1 is positioned beneath a sampling apparatus 160, each sample head 162 is configured to extract material from a respective egg 1 and then deposit the extracted material into a respective sample receptacle 152 of a sample tray 150.

Figure 31:
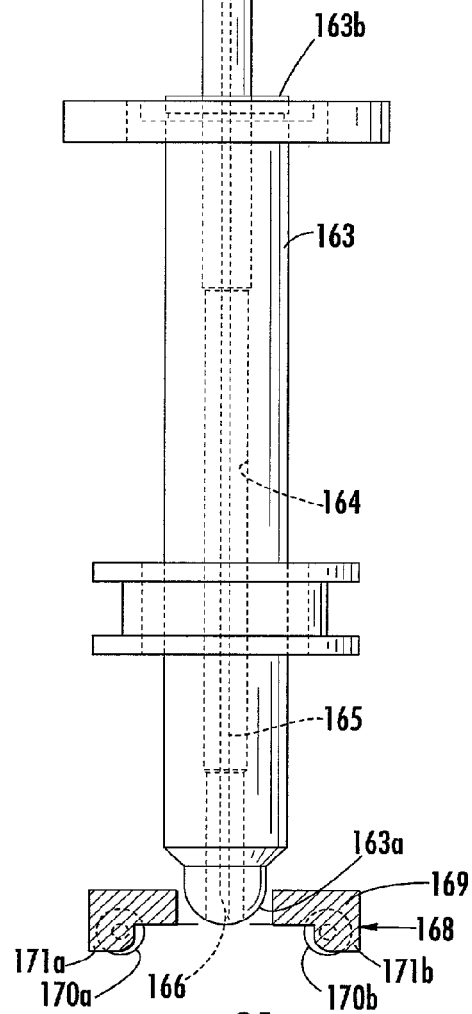
FIG. 31 is a side view of a sample head for extracting material from an egg, according to embodiments of the present invention.

Referring to FIG. 31, each sample head 162 according to the illustrated embodiment, includes an elongated housing 163 having opposite first and second ends 163a, 163b and an elongated passageway (guide) 164 that extends therebetween. An elongated needle 16S is disposed within the elongated passageway 164 and is movable between a retracted position and first and second extended positions. The tip 166 of the needle 165 is contained within the passageway 164 when the needle 165 is in the retracted position, and the tip 166 of the needle 165 extends from the housing first end 163a when the needle 165 is in the first and second extended positions. The needle 165, when in the first extended position, is configured to punch through the shell of an egg and extract material (e.g., allantoic fluid) from the egg. The needle 165, when in the second extended position, is configured to deliver extracted egg material into a respective sample receptacle of a sample tray, as will be described below.

The needle 165 may be a hypodermic needle having an eggshell piercing tip configuration. According to embodiments of the present invention, a needle tip 166 may have a beveled or blunt configuration to facilitate punching through an egg shell. According to embodiments of the present invention, a needle 165 may have an aperture formed in a side portion thereof in lieu of the tip 166 to help prevent blockage of the needle lumen caused by punching through an egg shell. Sampling head needles 165 according to embodiments of the present invention are particularly adapted to withdraw allantoic fluid from eggs.

As is known to those skilled in the art, allantoic fluid is an excretory medium for the nitrogenous metabolites of an avian embryo. Allantoic fluid begins to form around Day 5 of incubation. It attains a maximum volume on about Day 13 of incubation and then wanes in volume as incubation continues dues to moisture loss and fluid resorbtion, but is still present in significant volumes on Day 18 of incubation.

Allantoic fluid is separated from the eggshell by the inner and outer shell membranes and the chorioallantoic membranes. Although the allantoic fluid encompasses the entire periphery of an embryonated egg, the allantoic fluid accumulates at the top of an egg directly underneath the membranes overlying the air cell. The accumulation of the allantoic fluid at the top of the egg is due to gravity and displacement by the dense embryo and yolk sac. Attempting to accurately sample the allantoic fluid through the top of an egg while the egg is upright may be difficult due to the variability of the air space from egg to egg. Gravity can be used to pool the allantoic fluid in a localized site. When an egg is turned on its longitudinal axis, the allantoic fluid will pool at the top side of the egg, directly underneath the shell. Laying the egg on its longitudinal axis renders the allantoic fluid an easier target to access.

The extraction of material, such as allantoic fluid, from eggs may be performed in various ways according to embodiments of the present invention. For example, if only live eggs are initially placed within the cradles 112 of the egg cradle table 110, all eggs will be sampled. However, if non-live eggs are also placed within the cradles 112 of the egg cradle table 110, only the live eggs will be sampled. Alternatively, the shell of all eggs, including non-live eggs, may be punched, but material only sampled from live eggs. According to alternative embodiments, each sample head 162 may comprise a biosensor or other device designed to analyze egg material (e.g., allantoic fluid) in situ. As will be described below, according to other embodiments of the present invention, egg material extraction and assaying of extracted material may be performed by the same sampling apparatus.

Each sample head 162 of the illustrated embodiment of FIG. 31 also includes an alignment member 168. The illustrated alignment member 168 includes a body portion 169 that is movably secured to the sample head housing first end 163*a*. Two pair of opposed wheels 170*a*, 170*b* are mounted to opposite end portions 171*a*, 171*b* of the body portion 169.

Figure 32:
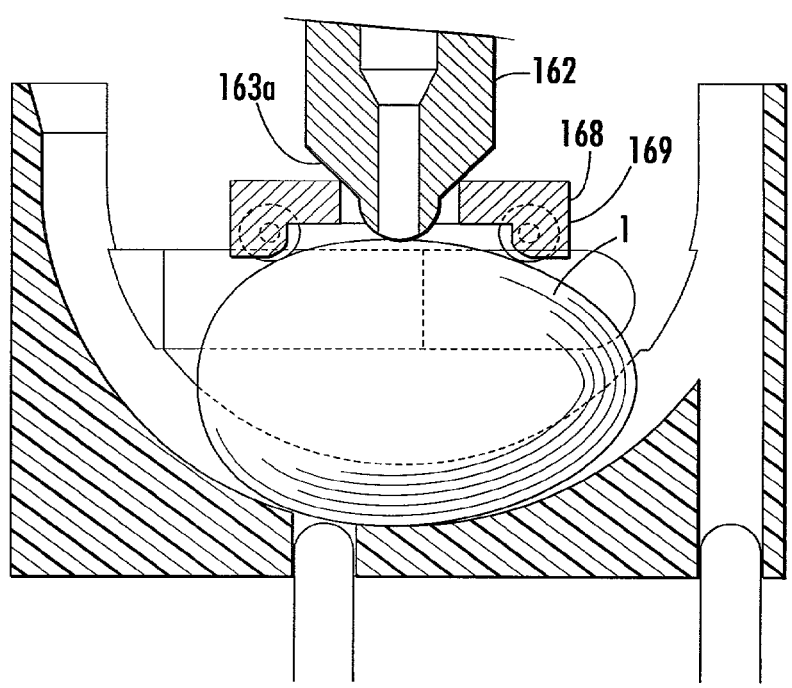
FIG. 32 is a side section view of an egg cradle within the illustrated array of FIG. 19 with an egg positioned therewithin in a generally horizontal position, and illustrating a sample head in contacting relationship with the egg.

As illustrated in FIG. 32, an egg 1 is held in position within a cradle 112 by the alignment member 168 when a sample head 162 is brought into contact with an egg within a cradle 112. The alignment member 168 adjusts the egg position and centers it within the cradle 112. In the illustrated embodiment, opposing wheels 170*a*, 170*b* are in contact with the egg shell along with the sample head housing first end 163*a*.

Figure 33:
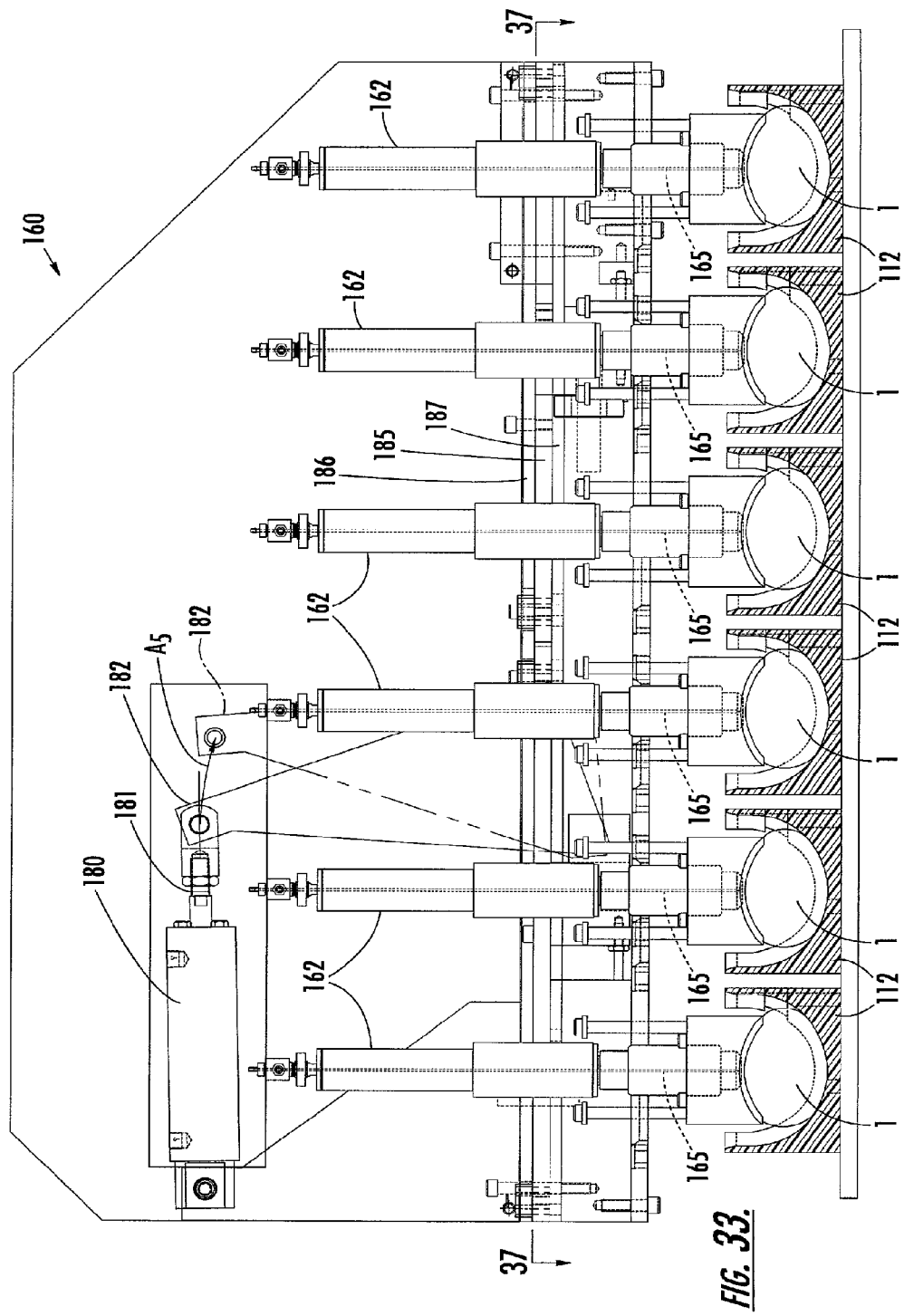
FIG. 33 is a side view of a plurality of sample heads for one of the four sampling apparatus in FIG. 14 wherein each sample head is in contact with the shell of an egg within a respective egg cradle prior to extracting material from the egg, and wherein a sample needle within each sample head is in a retracted position.
Figure 34:
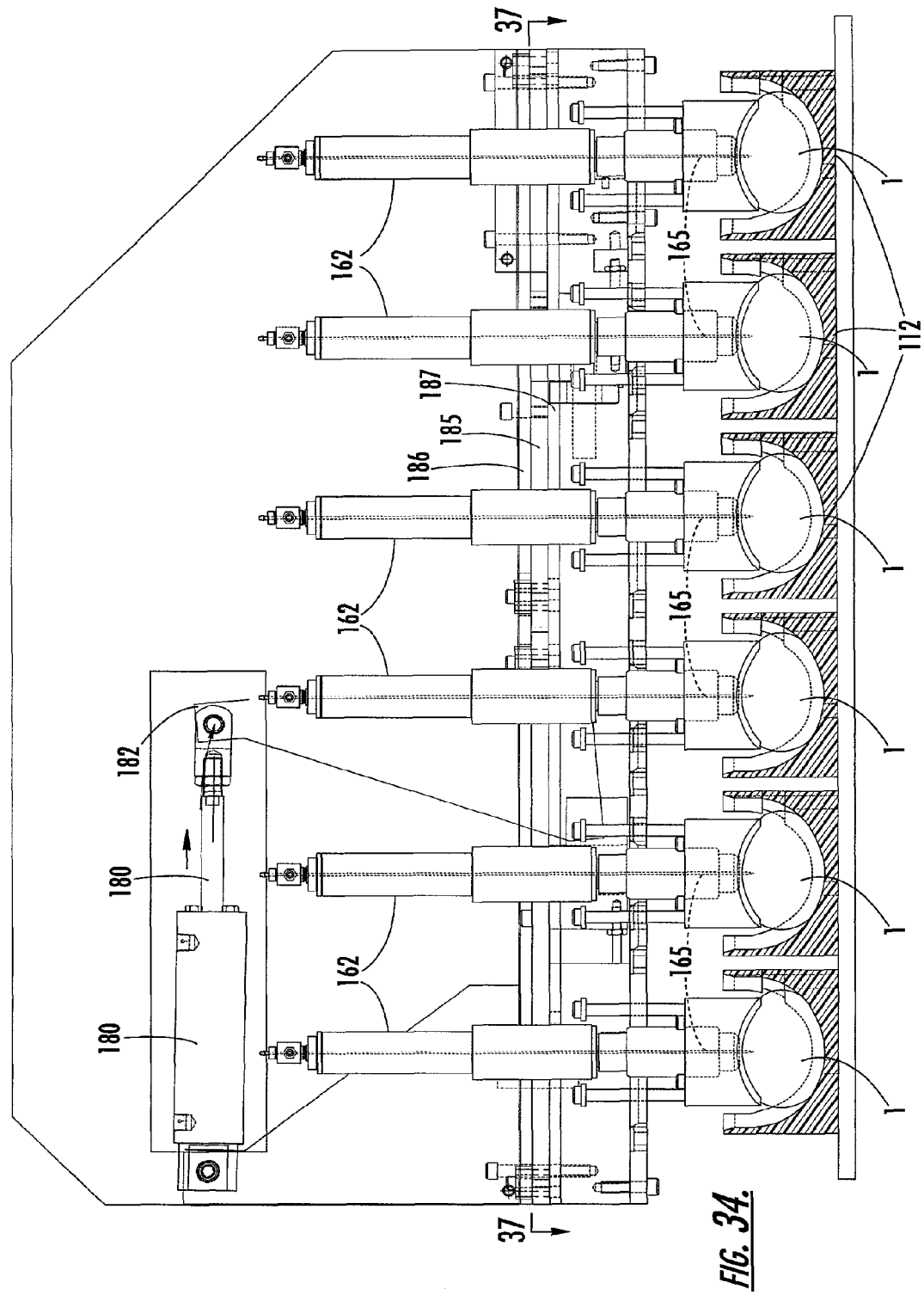
FIG. 34 illustrates the sample heads of FIG. 33 wherein the sample needles are in a first extended position and have pierced the shell of each respective egg and are in position to extract material from each respective egg.

Embodiments of the present invention are not limited to the illustrated configuration of the sample head of FIG. 31. For example, a sample head may have an alignment member without the pair of opposed wheels 170*a*, 170*b*. Moreover, embodiments of the present invention may utilize alignment members having various shapes, sizes and configurations. Sample head operations are illustrated in FIGS. 33-35. FIG. 33 is a side view of a plurality of sample heads 162 for one of the four illustrated sampling apparatus 160 in FIG. 14. Each sample head is in contact with the shell of an egg 1 within a respective egg cradle 112 prior to extracting material from the egg 1, and a sample needle 165 within each sample head is in a retracted position. In addition, an actuator 180 is illustrated moving arm 182 via actuator piston 181 from a first position to a second position, as indicated by arrow $A_5$. Arm 182 is linked to sampling head locking plates 185 that are movably sandwiched between stationary plates 186 and 187. As will be described below, locking plates 185 are configured to maintain each sample head 162 in a vertically-locked position relative to a respective egg 1 within a cradle 112 as material is extracted from the egg 1.

In FIG. 34, arm 182 has moved to the second position such that the locking plates 185 are spread apart to the locked position so as to restrain vertical movement of the sample heads 162. The sample needles 165 have been extended to a first extended position and have pierced the shell of each respective egg. In the first position the sample needles 165 are in position to extract material (e.g., allantoic fluid) from each respective egg.

In FIG. 35, the arm 182 has moved back to the first position such that the locking plates 185 do not restrain vertical movement of the sample heads 162. The sample needles 165 have been extended to a second extended position and are in position to dispense material extracted from respective eggs into respective sample receptacles 152 in a sample template 150. The second extended position provides adequate clearance beyond the sample head 162 and/or alignment member 168 so that the needles 165 can reach the sample receptacles 152 in a sample tray 150 and so that the needles 165 can reach sanitation nozzles or other apparatus that deliver sanitizing fluid to the needles 165.

Embodiments of the present invention are not limited to sample heads wherein needles have first and second extended positions. According to alternative embodiments, a needle may move from a retracted position to only one extended position for extracting material from eggs.

For dispensing extracted material into a sample receptacle, a sample tray may be moved upwardly to the needle. Similarly, a sanitizing nozzle or other apparatus may move upwardly to the needle.

Figure 36D:
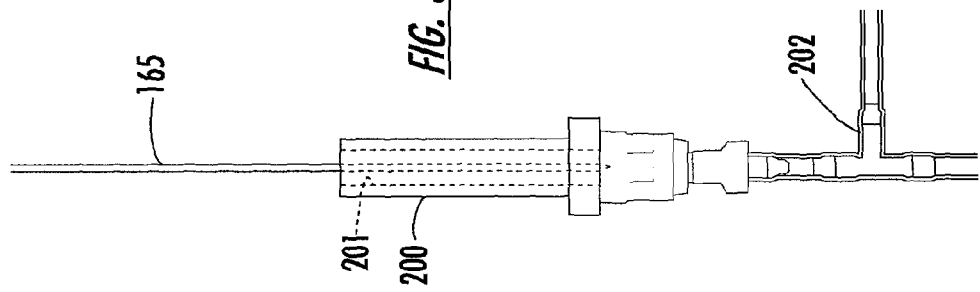
FIG. 36D illustrates an exemplary sanitizing fountain that may be utilized to sterilize a respective sample needle, in accordance with embodiments of the present invention.
Figure 36C:
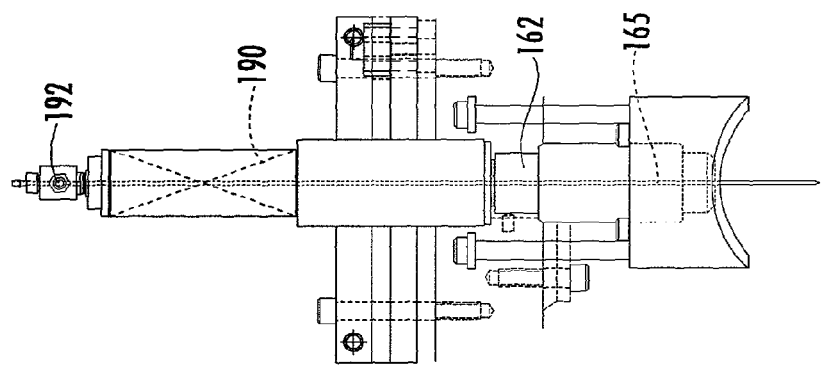
FIG. 36C illustrates the sample head of FIG. 36B wherein the biasing force of the biasing member has been overcome such that the sample needle is in the second extended position and is configured to dispense material extracted from the egg into a sample receptacle and then be sanitized.
Figure 36B:
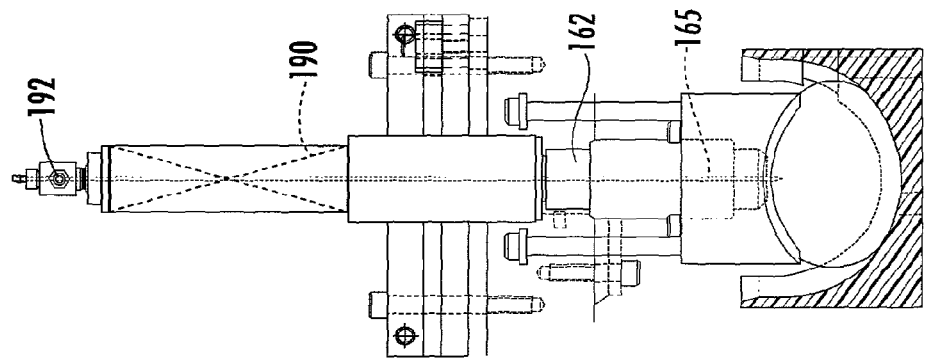
FIG. 36B illustrates the sample head of FIG. 536A wherein the biasing force of air in the lower half of the sample head cylinder has been overcome such that the sample needle is in a first extended position and has pierced the shell of the egg and is in position to extract material from the egg.
Figure 36A:
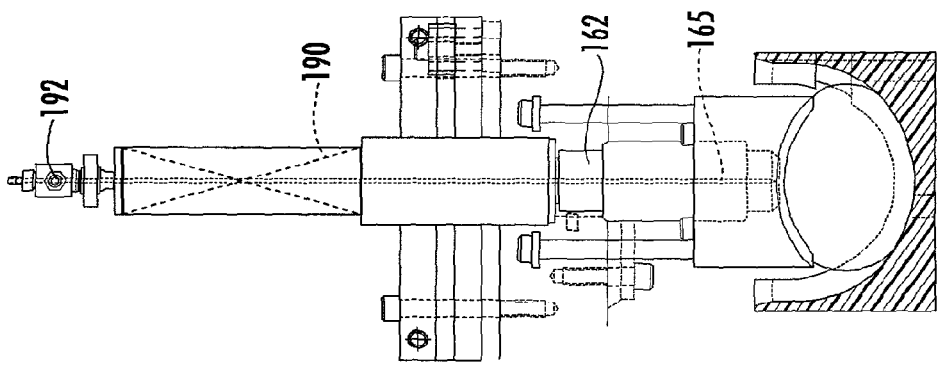
FIG. 36A illustrates one of the sample heads of FIG. 33 with a biasing member illustrated in phantom line.

Movement of a sample needle 165 within a sample head 162 is illustrated in greater detail in FIGS. 36A-36C. Each sample head 162 includes a biasing member (e.g., a spring) 190, as illustrated in FIG. 36A. Movement of each sample needle 165 from a retracted position to both the first and second extended positions is facilitated by air pressure (or other fluid pressure) that is provided from a compressed air source (or other fluid source). To move the sample needle 165 from the retracted position to the first extended position (FIG. 363), air (or other fluid) pressure is supplied at a level sufficient (e.g., 28 psi) to overcome the biasing force of air in the lower half of the sample head 162, but not sufficient to overcome the combined biasing forces of air in the lower half of the sample head and the biasing member 190. To move the sample needle 165 from the retracted position to the second extended position (FIG. 36C), air (or other fluid) pressure is supplied via one or more fittings (not shown) on the sample head 162 at a level sufficient (e.g., 75 psi) to overcome the combined biasing forces of the air in the lower half of the sample head and the biasing member 190.

In the illustrated embodiment, the biasing member 190 is configured to urge the sample needle 165 from the second extended position to the first extended position when air pressure within the lower half of the sample head 162 is reduced. Air pressure is increased in the lower half of the sample head 162 to move the sample needle 165 to the retracted position. The biasing member 190 may have various shapes, configurations and/or sizes and is not limited to a particular embodiment.

In the illustrated embodiment, air is supplied via nozzle 192 to each sample head 162 to dry outside portions of each respective sample needle 165 after sanitizing each respective sample needle 165.

Referring to FIG. 36D, an exemplary sanitizing fountain 200 that may be utilized to sterilize a respective sample needle 165, in accordance with embodiments of the present invention, is illustrated. The illustrated fountain 200 has a bore 201 formed therein that is configured to receive a respective sample needle 165 therein. Sanitizing fluid is supplied to the fountain from a source via a supply line 202. The fountain 200 contains one or more nozzles (not shown) that are configured to spray the sample needle 165 with sanitizing fluid. According to embodiments of the present invention, an array of fountains 200 are provided such that sample needles 165 from a respective array of sample heads 162 can be lowered into respective fountains 200 at the same time after dispensing extracted egg material into sample receptacles of a sample tray. Embodiments of the present invention, however, are not limited to the illustrated sanitizing fountain 200. Sanitizing systems utilizing various types of devices for applying sanitizing fluid to a sample needle may be utilized.

Figure 37:
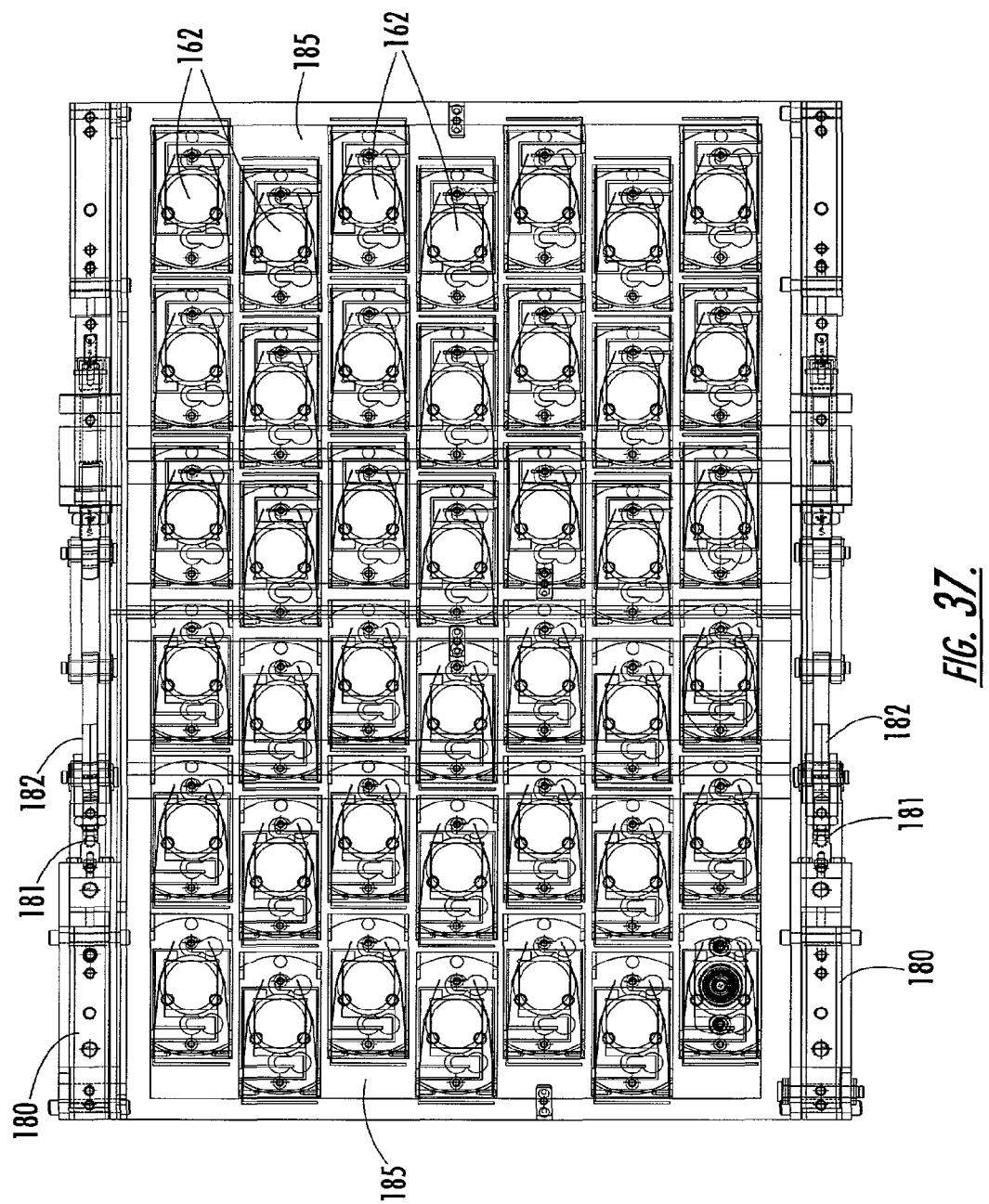
FIG. 37 is a plan view of the array of sample heads of FIG. 33 taken along lines 37-37 and illustrating locking plates according to embodiments of the present invention that are configured to maintain each sample head in a vertically-locked position relative to a respective egg as material is extracted from the egg.

Referring now to FIGS. 37, 38A-38B and 39A-39C, the locking plates 185 will now be described. FIG. 37 is a plan view of an array of sample heads 162 taken along lines 37-37 of FIG. 33 that illustrates the locking plates 185. The illustrated locking plates 185 include a plurality of apertures 300 formed therein in the array pattern of the array of sample heads 162. Each sample head 162 is configured to be slidably disposed within a respective aperture 300 and is configured to move freely in a vertical direction when the locking plates 185 are not in the locked position.

Within each illustrated aperture are a pair of resilient arms 302 that are configured to apply a biasing force to a respective sampling head 162 when the locking plates 185 are moved to the locked position. The resilient arms 302 are configured to prevent one sampling head that is slightly larger than other sampling heads from binding the whole apparatus and preventing other sampling heads from being locked in place. In the illustrated embodiment of FIG. 38A, the locking plates 185 move away from each other when moved to the locked position. However, embodiments of the present invention are not limited to the illustrated locking plates 185 or to their direction of movement.

FIG. 383 illustrates locking plates 185' according to other embodiments of the present invention. The illustrated locking plates 185' include a plurality of apertures 300 formed therein the array pattern of the array of sample heads 162. Each sample head 162 is configured to be slidably disposed within a respective aperture 300 and is configured to move freely in a vertical direction when the locking plates 185' are not in the locked position. In the illustrated embodiment of FIG. 383, the locking plates 185' also move away from each other when moved to the locked position. Within each illustrated aperture are a pair of resilient arms 302', a support block 303, and springs 304 connected to the resilient arms 302' that are configured to apply a biasing force to the support block 303. When the locking plates 185' are moved relative to the fixed upper and lower plates, the resilient arms 302' engage a respective sampling head and the springs 304 apply a biasing force to the block 303 which restrains the sampling head from vertical movement. As with the embodiment of FIG. 38A, the resilient arms 302' are configured to prevent one sampling head that is slightly larger than other sampling heads from binding the whole apparatus and preventing other sampling heads from being locked in place.

Figure 38A:
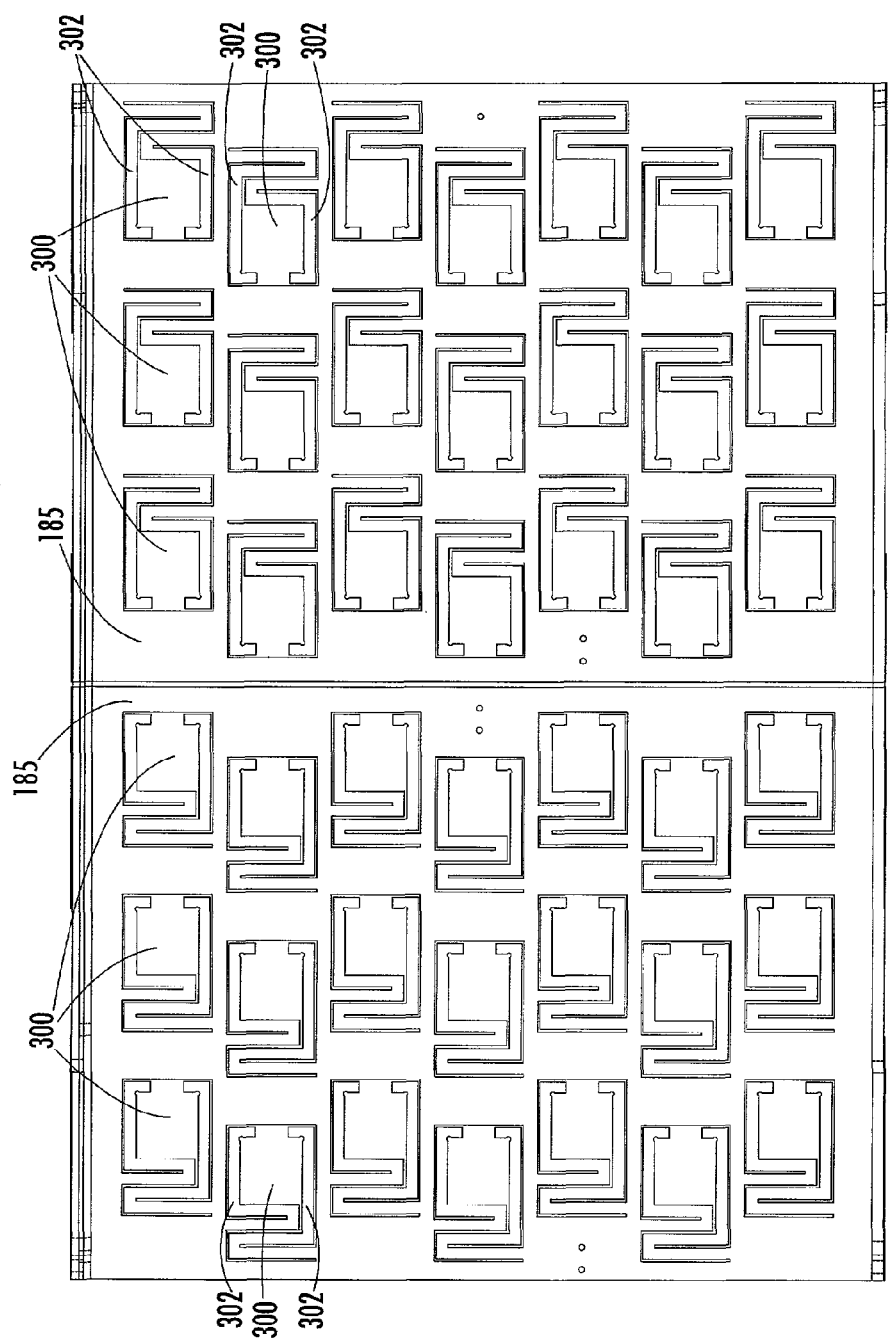
FIG. 38A is a plan view of the locking plates of FIG. 37 according to one embodiment of the present invention.
Figure 38B:
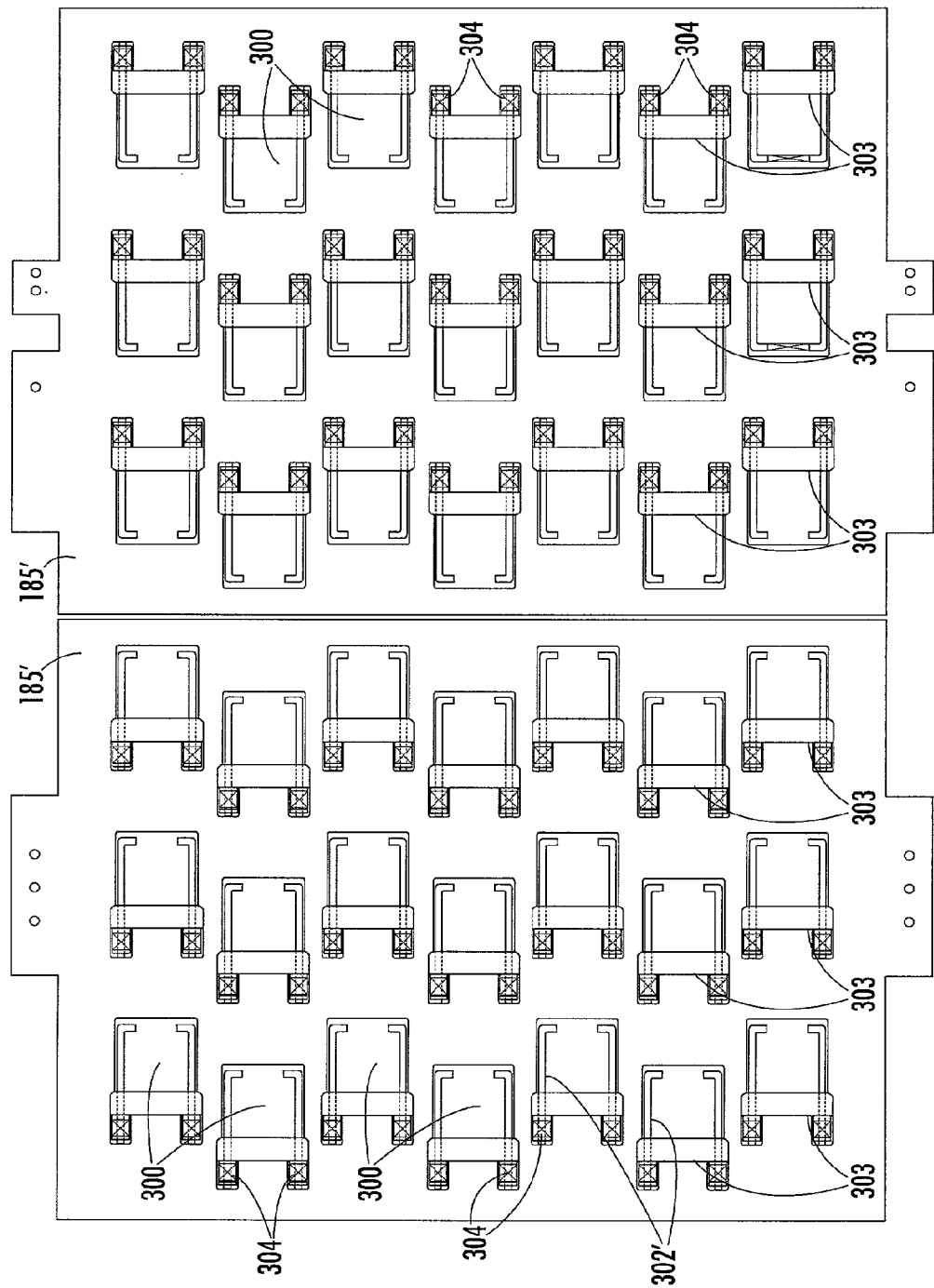
FIG. 38B is a plan view of locking plates according to an alternative embodiment of the present invention.

Embodiments of the present invention are not limited to the illustrated locking plates 185 of FIGS. 38A-38B. Locking plates having different configurations may be utilized as well. In addition, other ways of restraining sampling head movement may be utilized (e.g., see U.S. Pat. No. 5,136,979 to Paul et al., which is incorporated herein by reference in its entirety).

Figure 39A:
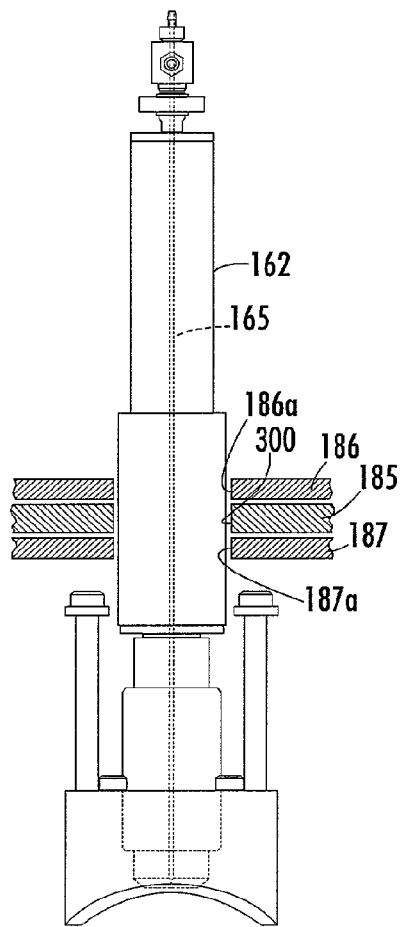
FIG. 39A is a side view of a sample head from the array of FIG. 33 illustrating the locking plate in a non-engaged position relative to the sample head.
Figure 39B:
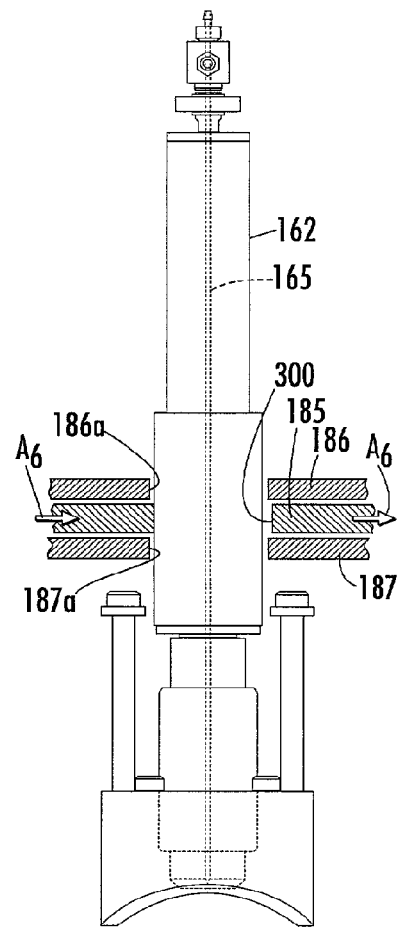
FIG. 39B illustrates the sample head of FIG. 39A wherein the locking plate is being moved to the right and has engaged the sample head to force the sample head against two stationary plates.
Figure 39C:
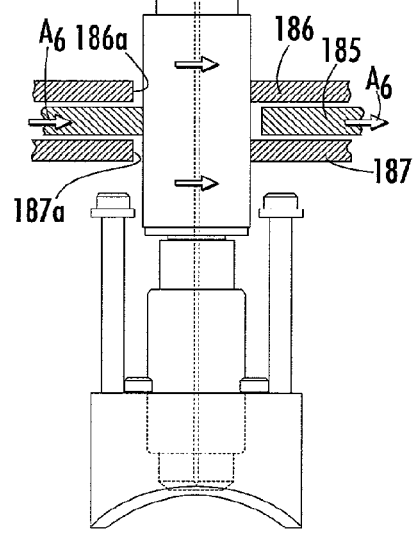
FIG. 39C illustrates the sample head of FIG. 39A wherein the locking plate has secured the sample head against the two stationary plates such that vertical movement of the sample head is restrained.

Movement of the locking plates 185 are illustrated in FIGS. 39A-39C. In FIG. 39A, a locking plate 185 is in an unlocked position and the sampling head 162 is free to move vertically within the aperture 300 of the locking plate 185 and the respective apertures 186a, 187a in the upper and lower stationary plates 186, 187, as illustrated. In FIG. 39B, the locking plate is being moved to the locked position (indicated by arrows $A_6$ such that the locking plate 185 pushes the sampling head 162 towards the upper and lower stationary plates 186, 187. In FIG. 39C, the sampling head 162 is wedged against the stationary upper and lower plates 186, 187 by the locking plate 185 such that vertical movement of the sampling head 162 is restrained. Referring now to FIG. 40, an exemplary sample tray 151 containing a plurality of sample receptacles 152 formed therein in various arrays is illustrated. Each sample receptacle 152 is configured to receive a sample of material extracted from a respective egg, such as allantoic fluid. Sample trays having various configurations and arrays of sample receptacles may be utilized in accordance with embodiments of the present invention. Sample trays may be formed from various materials and via various techniques. The present invention is not limited to the illustrated sample tray 150.

Figure 41:
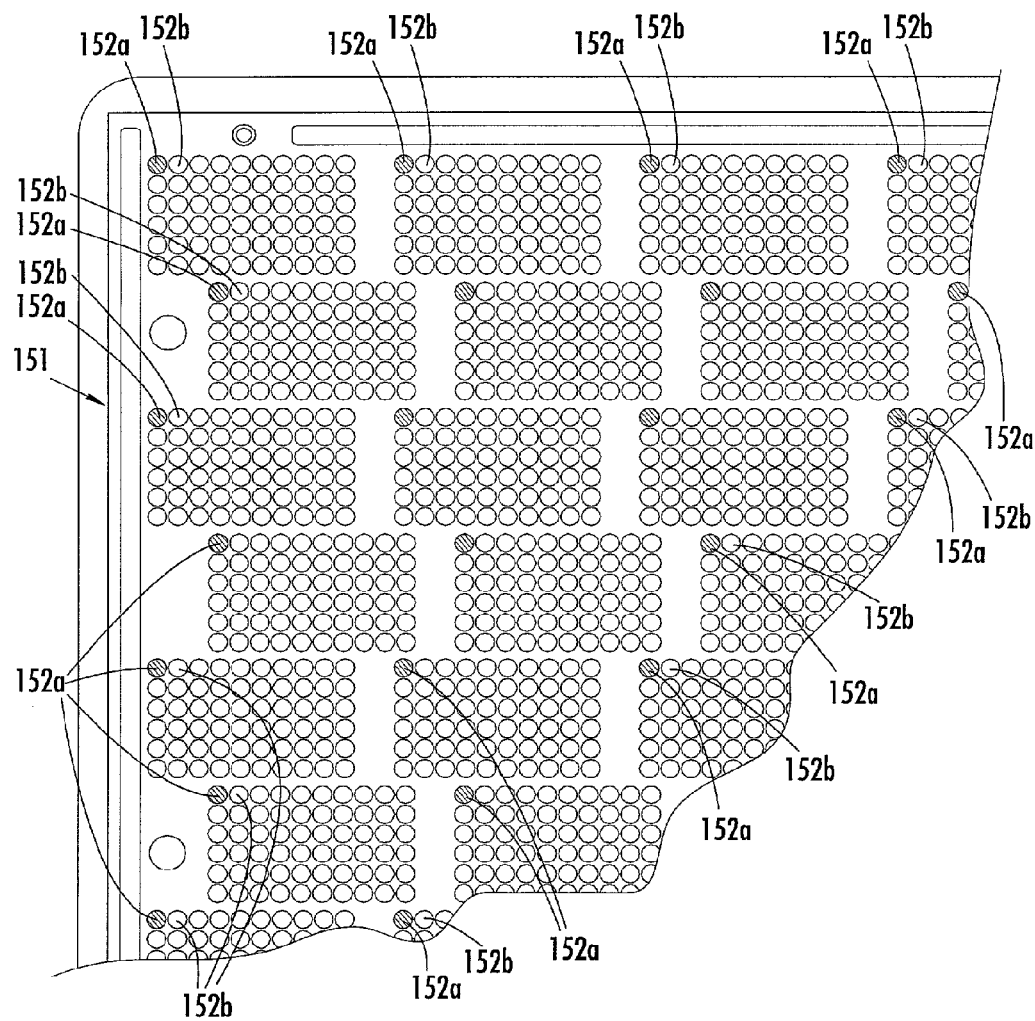
FIG. 41 is an enlarged partial plan view of the sample tray of FIG. 40 illustrating material extracted from eggs dispensed within respective sample receptacles of the sample tray.

FIG. 41 is an enlarged partial plan view of the sample tray of FIG. 40 illustrating material extracted from eggs dispensed within respective sample receptacles of the sample tray. Material extracted from eggs may be disposed within respective sample receptacles 152 of a sample tray 150 according to various dispensing patterns. For example, as illustrated in FIG. 41, material from eggs from a particular flat can be disposed within the first receptacle 152a in the first row of a grouping of receptacles. Material from eggs in a subsequent flat can be disposed in the second receptacle 152b in the first row, etc. Dispensing patterns are preferably controlled via a controller (e.g., PLC 70a of FIG. 12).

FIGS. 42A-42B are top plan views of the sample tray handling system 150 according to embodiments of the present invention and illustrating sample trays 151 being moved (indicated by arrows $A_7$) relative to (i.e., beneath) a sampling apparatus 160 of FIG. 14. Because each sampling apparatus 160 of the illustrated material extraction apparatus of FIG. 14 is fixed, the sample tray handling system 150 is configured to move sample receptacles 152 beneath respective sampling heads 162 such that material extracted from eggs can be dispensed within appropriate sample receptacles. Once the sample receptacles 152 of a sample tray 151 have received extracted egg material, the sample trays 151 are offloaded (either manually or automatically) and the extracted egg material is allowed to dry. Once a sample tray 151 is offloaded, the sample tray handling system 150 moves back to receive a new sample tray 151 loaded by an operator.

Although not illustrated, a sanitizer system is preferably provided with the illustrated material extraction apparatus 30 of FIG. 14. For example, a sanitizer system may be operably associated with the sampling heads 162 of each sampling apparatus 160 and configured to pump sanitizing fluid through and around the outside of the sample heads 162, including the elongated needles 165 and needle passageways 164. For example, see the illustrated fountain 200 of FIG. 36D which is configured to apply sanitizing fluid to a sample needle 165. Sanitizing fluid is preferably applied to each portion of a sample head 162 that comes into contact with an egg after depositing material extracted from an egg into a respective sample receptacle 152 in the sample tray 150. Preferably, means for drying each sample head 162, needle 165, and passageway 164 are provided after sanitizing fluid has been applied thereto. For example, a system for directing air at each sample head 162, needle 165, and passageway 164 may be provided. In the illustrated embodiment of FIGS. 36A-36C, drying air is provided via nozzle 192.

Exemplary sanitizing fluid systems for providing sanitizing fluid and which may be utilized in accordance with embodiments of the present invention are described in U.S. Pat. Nos. 5,176,101, and RE 35,973, which are incorporated herein by reference in their entireties.

Embodiments of the present invention are not limited to the illustrated material extraction apparatus of FIG. 14, or to the exact process described above. Each of the components (egg transfer apparatus 130, egg cradle table 110, sampling apparatus 160, egg flat conveyor systems 102, 104) may operate in various ways as long as material extracted from an egg can be identified as coming from that particular egg.

Assaying Station

Referring now to FIGS. 43-46, an assaying station 60 and methods of using the assaying station 60 to determine characteristics of eggs, according to embodiments of the present invention, will now be described. The illustrated assaying station 60 is configured to process a plurality of sample trays containing material extracted from eggs as described above in order to determine one or more characteristics of the eggs.

Referring initially to FIGS. 43-44, a holding area 410 is configured to receive and hold a plurality of sample trays containing material extracted from a plurality of eggs for a predetermined period of time. Each sample tray is then transferred from the holding area 410 into the biosensor (e.g., yeast) application 11 area 420 where a biosensor is added to the sample receptacles in each sample tray. Each sample tray then passes into the color application area 430 where a color substrate (e.g., OPNG substrate) is added to the sample receptacles in each sample tray. Broadly speaking, a biosensor and a color substrate are added to the dried material (e.g., allantoic fluid) extracted from an egg to cause a chemical reaction that can change the color of the dried material based upon a characteristic (e.g., gender) of an egg. After a predetermined period of time, each sample tray is transferred 440 to the "read" area 450 and the color of the material in each sample receptacle is analyzed to determine the characteristic. For example, if the characteristic to be determined is gender, the material extracted from a female egg may have a color that is easily distinguishable from that of a male egg. Before a sample tray is disposed of, it is preferable to destroy the biosensor via the decontamination area 460.

According to embodiments of the present invention, the assaying station 60 is particularly adaptable to determine gender of eggs. An operator loads a plurality of sample templates containing material (e.g., allantoic fluid) extracted from eggs into the assaying station 60. Within the assaying module 60, each sample template is moved via a conveyor system beneath a dispensing head which dispenses a predetermined amount (e.g., about 75 .mu.1) of reagent (e.g., a LiveSensors.™. brand cell-based biosensor, LifeSensors, Inc., Malvern, Pa.) into each respective sample receptacle. Each sample template then progresses through an environmentally-controlled chamber for a predetermined period of time (e.g., about 3.5 hours). Each sample template is moved via a conveyor system beneath another dispensing head which dispenses a predetermined amount of a color substrate (e.g., ONPG-based substrate) into each sample receptacle. Each sample template then progresses through an environmentally-controlled chamber for a predetermined period of time (e.g., about 45 minutes) to allow color development within each well.

The LiveSensors™ brand cell-based biosensor is utilized to detect estrogenic compounds in allantoic fluid. An exemplary LiveSensors™ brand cell-based biosensor is a genetically modified yeast transformed with yeast expression vector for the human estrogen receptor, the reporter gene that contains promoter with estrogen response elements coupled with *E. coli* β-galactosidase. In the presence of estrogens, the estrogen receptor binds to the estrogen response elements and initiates transcription of the reporter gene. The concentration of estrogens in the allantoic fluid is correlative with the level of induction of the reporter gene. The activity of the reporter gene product, B-galactosidase, is measured using an ONPG-based substrate, which yields a yellow calorimetric signal. LiveSensors™ brand cell-based biosensor can detect femtomolar levels of estrogens. The strain of yeast of the LiveSensors™ brand cell-based biosensor is comprised of the same strain commonly used in the baking industry, *Saccharomyces cerevisiae*. The LiveSensors™ brand cell-based biosensor can distinguish between male and female embryos using only about four microliters (4 μl) of allantoic fluid.

Specifically, the extracted allantoic fluid contains estradiol conjugates which are cleaved by an enzyme (glucuronidase) secreted by the yeast during an initial allantoic fluid/yeast sensor incubation. The presence of "free" estradiol readily induces the reporter gene system within the yeast to produce Beta-galactosidase. The Beta-galactosidase then reacts with an ONPG-based substrate, added after the allantoic fluid/yeast sensor incubation, to generate a color signal.

According to alternative embodiments of the present invention, the yeast may be induced to secrete GFP instead of Beta-Gal, which is fluorescent by itself and doesn't require the addition of a calorimetric substrate.

The color of the material in each sample receptacle can be determined in various ways. One technique may include illuminating the extracted material with a white light and using a CCD (charge coupled device) camera that scans each sample receptacle and electronically filters out all color signals but the specific color signal (e.g., yellow, pink, etc.) that identifies a gender (e.g., females). Preferably, each sample tray is transparent and the extracted material within each sample tray is illuminated from below. A CCD camera may be configured to count the number of pixels of a color in a respective sample receptacle to determine if the pixel number exceeds a certain threshold. If so, the CCD camera can output a digital signal signifying a female at that location. This information is stored via a data processor on the network.

Figure 45:
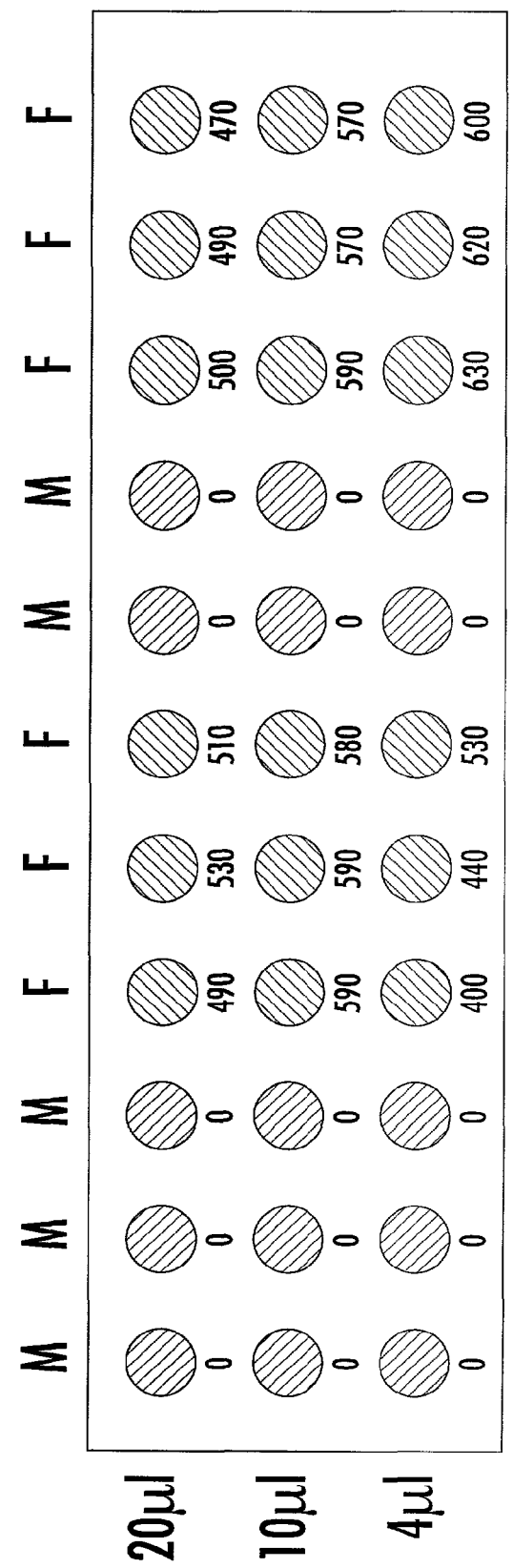
FIG. 45 is a plan view of a portion of a sample tray wherein egg material in each receptacle has been assayed to reveal a visible indication of a characteristic of a respective egg.

FIG. 45 depicts an assay conducted with a LiveSensors™ brand cell-based biosensor for various amounts of allantoic fluid (i.e., 4, 10, 20 .mu.1). The intensity of the color (e.g., yellow) as measured in pixels by a CCD camera is indicated under each sample receptacle. As illustrated, females have a greater yellow color intensity than males.

According to embodiments of the present invention, the reagent (e.g., a LiveSensors™ brand cell-based biosensor) within each well is then destroyed (e.g., via heat and/or via chemical treatment) in the decontamination area 460 prior to disposal of each sample template. According to embodiments of the present invention utilizing a LiveSensors™ brand cell-based biosensor, a sample of material such as allantoic fluid withdrawn from an egg may contain upwards of about twenty percent (20%) blood contamination. Moreover, the incubation temperature may fluctuate by about five degrees Centigrade (±5° C.), and sample incubation times can fluctuate by thirty minutes or more. In addition, samples withdrawn from eggs can be held for certain periods of time (e.g., over night) prior to initiating assaying procedures according to embodiments of the present invention.

Another technique may involve illuminating the extracted material with a white light and utilizing an array of photodiodes with color filters. Each photodiode will output a signal based on the intensity of the color it sees.

Embodiments of the present invention are not limited to the yeast-based assaying techniques. Moreover, embodiments of the present invention are not limited to identifying gender of eggs. Various assaying techniques may be utilized for analyzing material extracted from eggs to identify various characteristics (e.g., gender, pathogen content, genetic markers related to bird health or performance) of eggs. For example, antibody-based systems and methods (e.g., commercial pregnancy testing systems and methods) may be utilized to detect estrogen in egg material. Moreover, antibody-based systems may be utilized to detect pathogens (e.g., *salmonella* and Marek's disease). As another example, PCR (polymer chain reaction) analysis may be utilized to detect the presence/absence of W chromosomes in egg material. Moreover, PCR analysis may be utilized to detect various genetic traits/flaws in egg material.

Accordingly, assaying modules may be provided that facilitate pathogen detection and genetic analysis of avian eggs.

Figure 46:
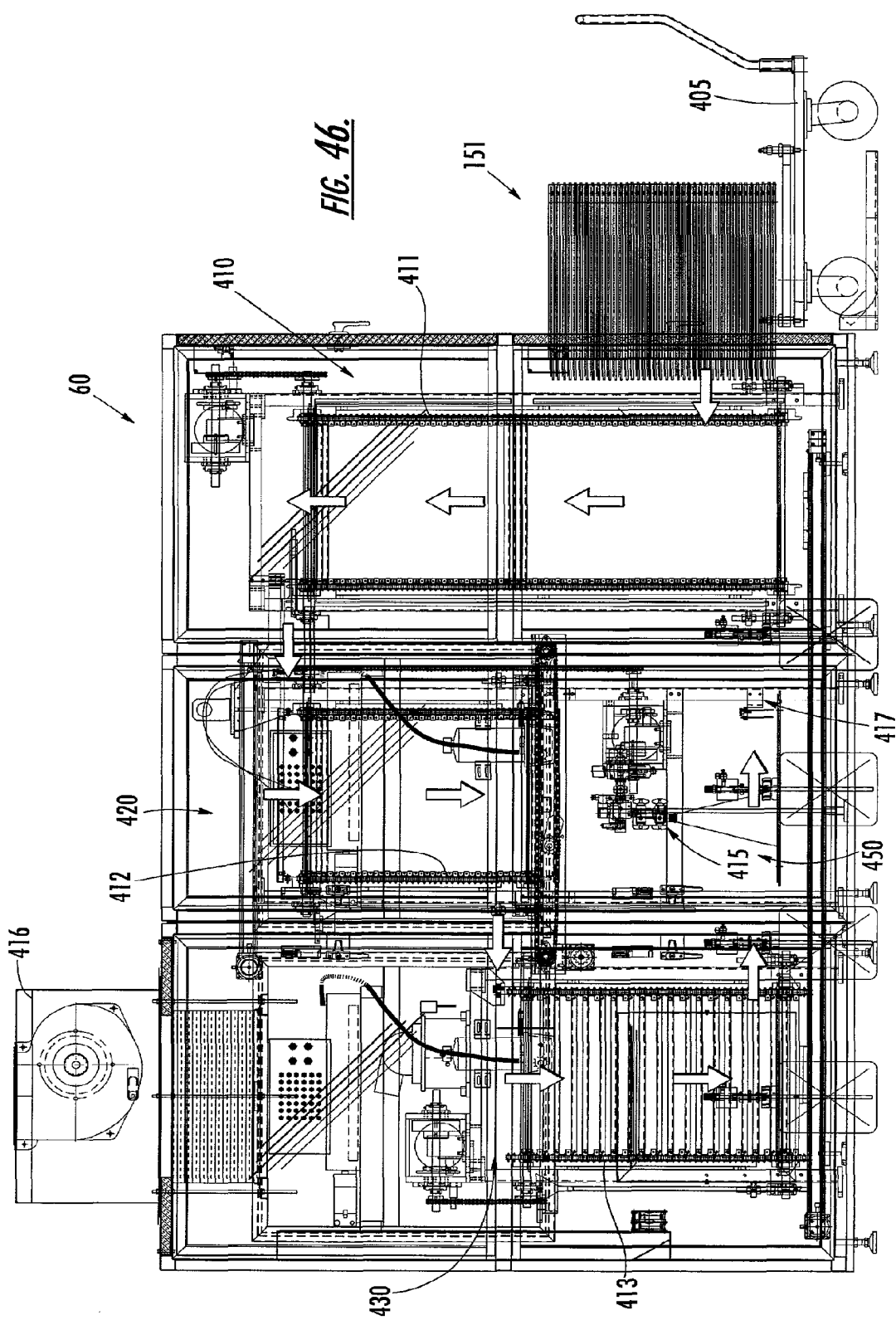
FIG. 46 is side elevation view of an assaying apparatus for assaying material extracted from eggs contained within a plurality of sample trays, according to embodiments of the present invention.

Referring now to FIG. 46, an assaying station apparatus 60, according to embodiments of the present invention, that is configured to assay material extracted from eggs contained within sample receptacles in a plurality of sample trays 151 is illustrated. The illustrated apparatus 60 includes a plurality of chambers or areas that are connected via conveyor systems that are configured to transport sample trays sequentially through the areas. Preferably, the areas are maintained at predetermined temperature and humidity levels. Additional environmental controls may be utilized as well. For example, air can be exhausted from the apparatus 60 via fan 416 at a designated flow rate, and may be filtered via a HEPA ("high efficiency particulate arresting") filtration system.

As illustrated in FIG. 46, a plurality of sample trays 151 are loaded from a cart 405 into the holding area 410. The holding area 410 includes a first endless conveyor system 411 that is configured to transport a plurality of sample trays in spaced-apart relationship upwardly to the biosensor application area 420 within a predetermined period of time. At the top of the holding area, each uppermost sample tray on the first endless conveyor system is pulled into the biosensor application area 420 and beneath dispensers (not shown) configured to dispense a biosensor (e.g., yeast) into the respective sample receptacles of the sample tray.

After a biosensor has been dispensed into the sample receptacles of a sample tray, the sample tray is conveyed by a second endless conveyor system 412 downwardly towards a color substrate application area 430. At the bottom of the second endless conveyor system 412, each lowermost sample tray is pulled into the color substrate application area 430 and beneath dispensers (not shown) that are configured to dispense a color substrate (e.g., ONPG-based substrate) into the respective sample receptacles of the sample tray.

After a color substrate has been dispensed into the sample receptacles of a sample tray, the sample tray is conveyed by a third endless conveyor system 413 downwardly towards a reading area 450. At the bottom of the third endless conveyor system 413, each lowermost sample tray is pulled into the reading area 450 and beneath one or more CCD cameras 415 that are configured to "read" the color of extracted material in each sample receptacle as described above. The biosensor in each sample receptacle is then destroyed by dispensing a chemical thereinto via dispensing head 417.

Treatment Station

The treatment station 40 of the illustrated embodiment of FIG. 11 may be configured to selectively treat eggs in any desired, suitable manner. It is particularly contemplated that the treatment station 40 inject live eggs with a treatment substance.

As used herein, the term "treatment substance" refers to a substance that is injected into an egg to achieve a desired result. Treatment substances include but are not limited to vaccines, antibiotics, vitamins, virus, and immunomodulatory substances. Vaccines designed for in ovo use to combat outbreaks of avian diseases in hatched birds are commercially available. Typically, the treatment substance is dispersed in a fluid medium, (e.g., is a fluid or emulsion) or is a solid dissolved in a fluid, or a particulate dispersed or suspended in a fluid.

A preferred treatment station 40 for use in accordance with embodiments of the present invention is the INOVOJECT® automated injection system (Embrex, Inc., Research Triangle Park, N.C.). However, any in ovo injection device capable of being operably connected, as described herein, to a controller is suitable for use according to embodiments of the present invention. Suitable injection devices preferably are designed to operate in conjunction with commercial egg carrier devices or flats, examples of which are described above.

Sorting Followed By Treatment

Figure 47:
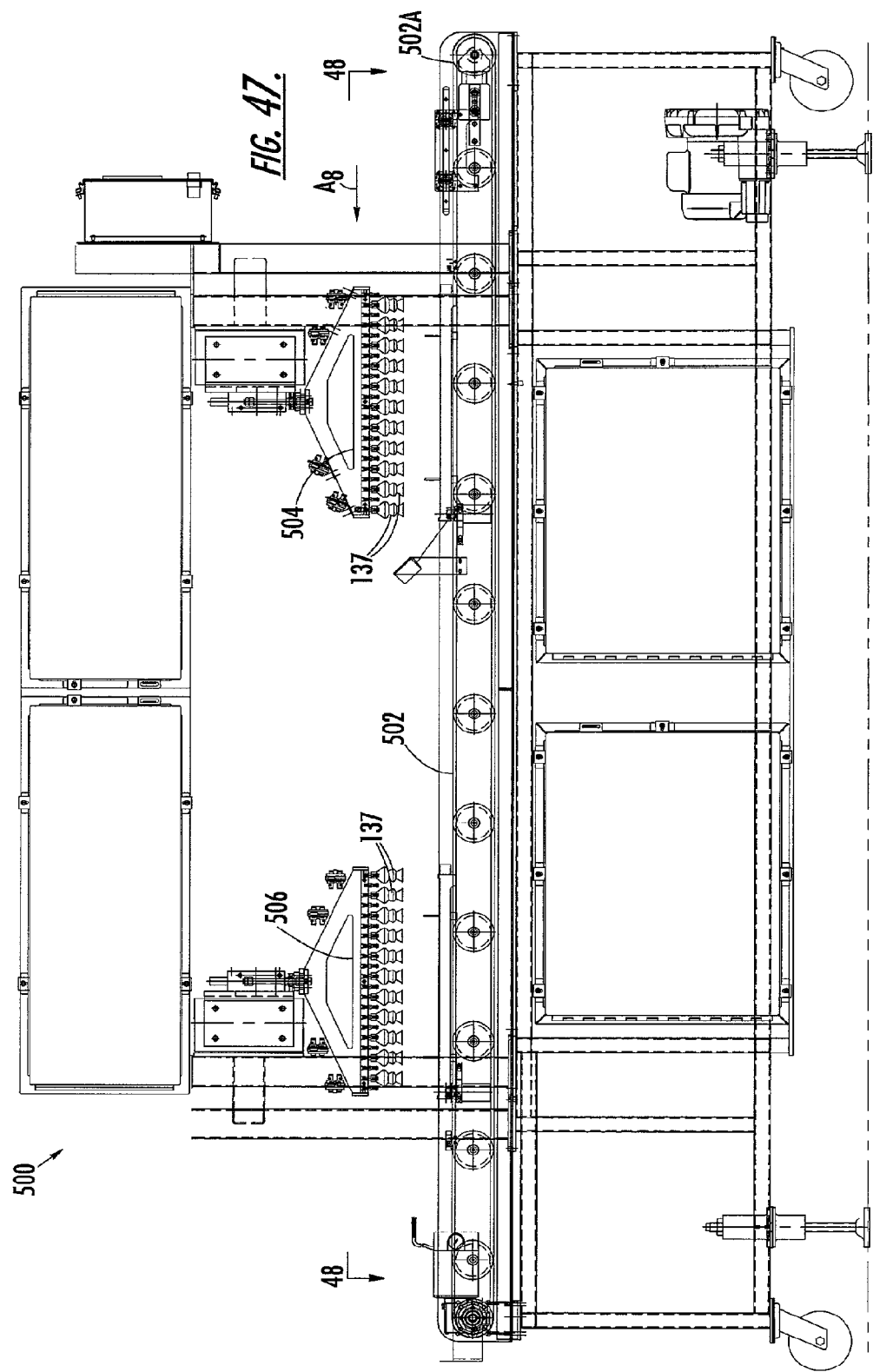
FIG. 47 is side elevation view of a sorting apparatus according to embodiments of the present invention.
Figure 48:
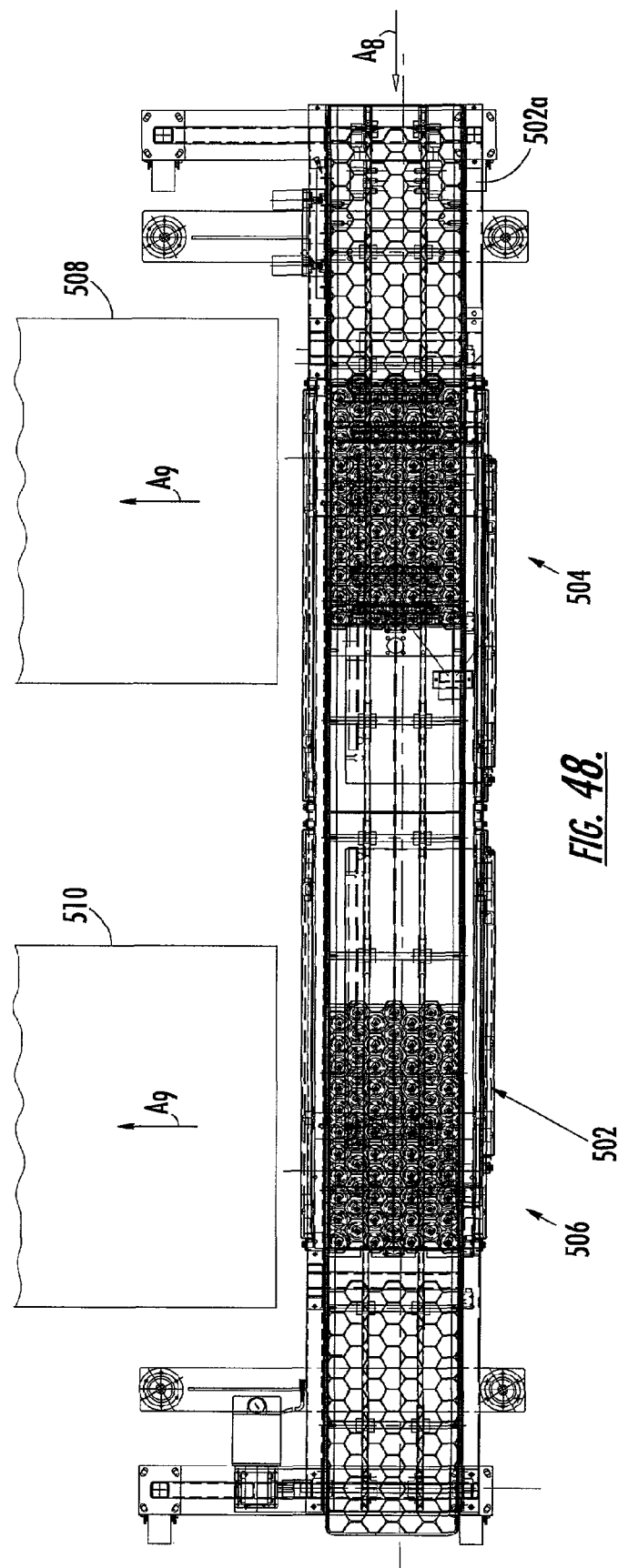
FIG. 48 is a top plan view of the sorting apparatus of FIG. 47 taken along lines 48-48.

Referring to FIGS. 47-51, sorting and transferring of eggs 1' prior to treatment, according to embodiments of the present invention, are illustrated. Referring initially to FIG. 47, a sorting station 500 includes an endless conveyor system 502 and a pair of transfer heads 504, 506 operably associated therewith. Eggs with identified characteristics (e.g., gender) are placed on the conveyor system 502 at one end 502a thereof in flats or other holding containers and are moved along the conveyor system in the direction indicated by arrow $A_8$. Transfer head 504 includes an array of vacuum cups 137 as described above with respect to FIGS. 27-29 that are configured to simultaneously lift a plurality of eggs from the conveyor system 502 and place the eggs on a first conveyor belt 508 (FIG. 48). Transfer head 506 includes an array of vacuum cups 137 that are configured to simultaneously lift a plurality of eggs from the conveyor system 502 and place the eggs on a second conveyor belt 510 (FIG. 48).

Each transfer head 504, 506 may be configured to selectively lift eggs from the conveyor system 502 based upon characteristics of the eggs (e.g., gender). For example, transfer head 504 may be configured to only lift male eggs, while transfer head 506 is configured to only lift female eggs. Transfer heads 504, 506 and conveyor system 502 are preferably under computer control (e.g., PLC 70c of FIG. 12).

As illustrated in FIG. 48, the transfer heads 504, 506 are configured to move in the direction indicated by arrows A such that eggs can be placed on respective conveyor belts 508, 510. The direction of travel of conveyor belts 508, 510 is also indicated by arrows $A_9$.

Figure 49:
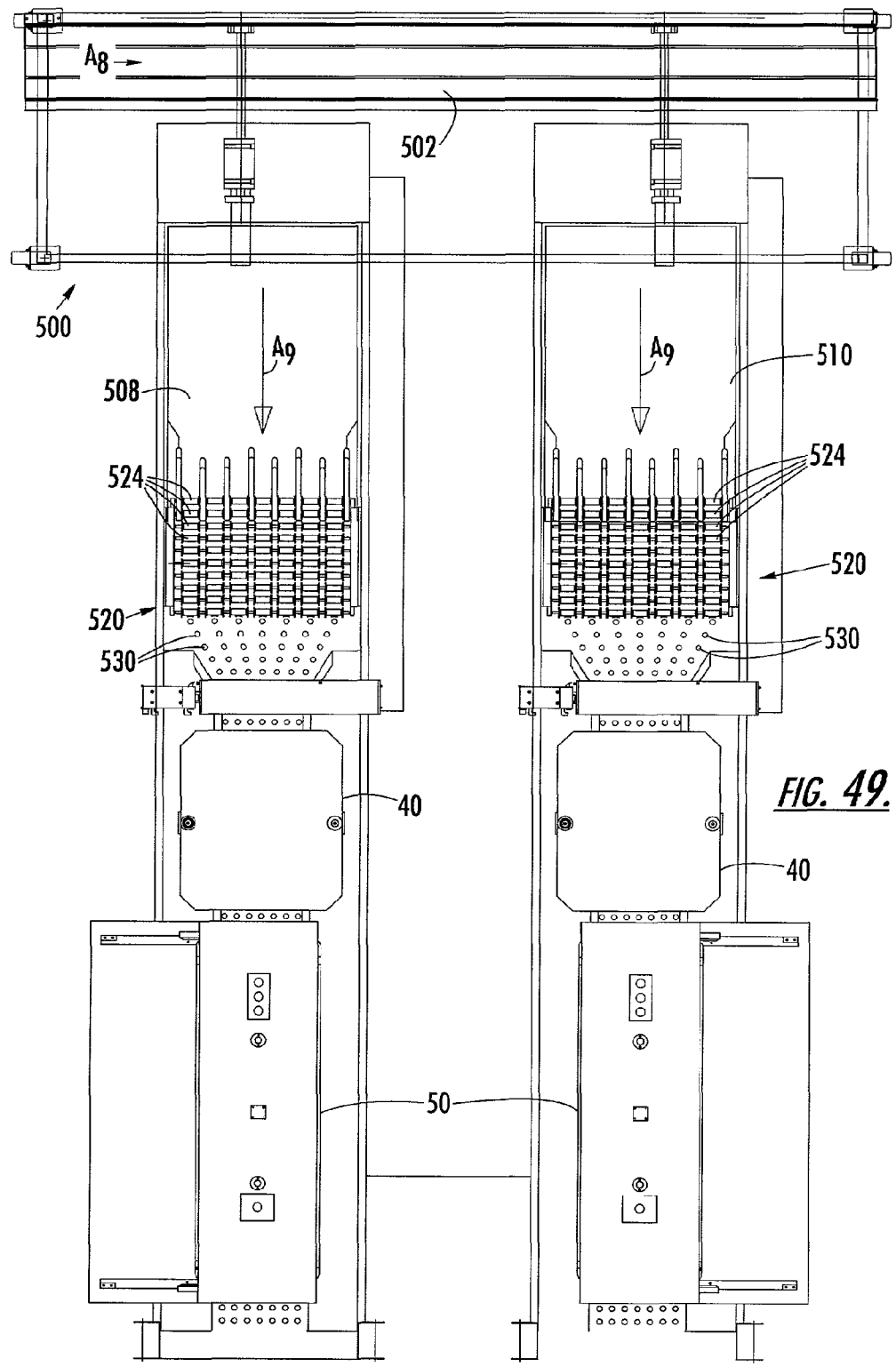
FIG. 49 is a top plan view of a backfill and injection apparatus to be used in conjunction with the sorting apparatus of FIG. 47 according to embodiments of the present invention.
Figure 50:
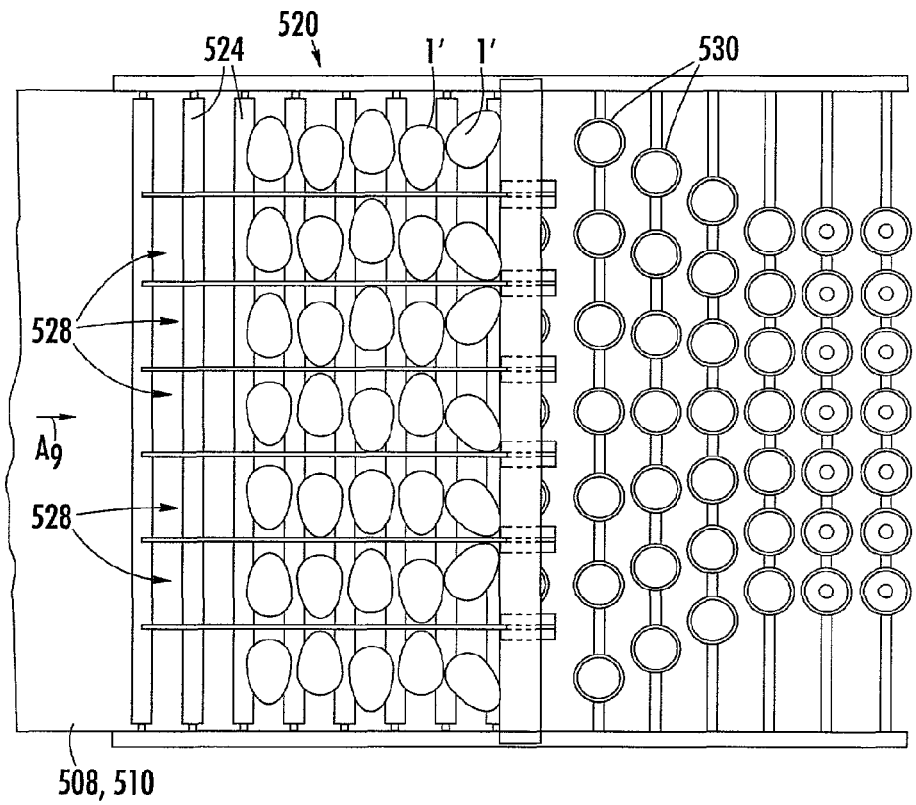
FIG. 50 is a top plan view of a backfill apparatus to be used in conjunction with the sorting apparatus of FIG. 47 and with a processing apparatus according to embodiments of the present invention.
Figure 51:
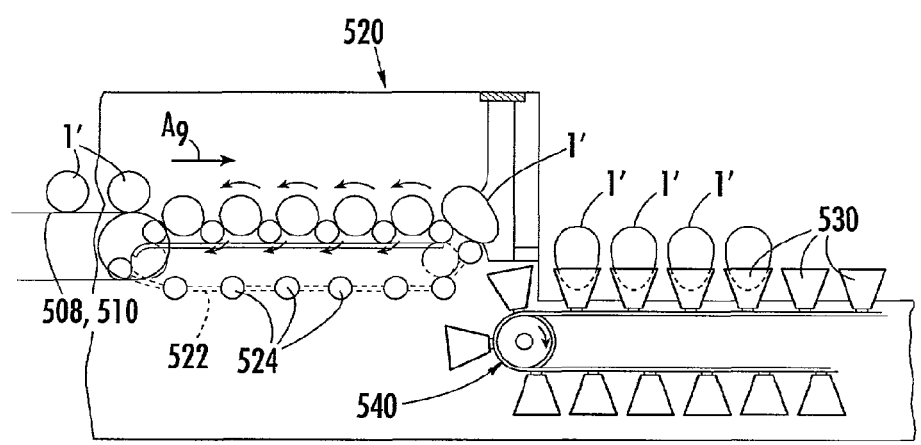
FIG. 51 is a side elevation view of the backfill apparatus of FIG. 50.

Referring now to FIG. 49, each conveyor belt 508, 510 is operably associated with a respective backfill apparatus 520. Each backfill apparatus 520 is configured to orient and hold eggs in a predetermined position for processing (e.g., injection, etc.). Each illustrated backfill apparatus 520 includes an endless conveyor 522 which has a plurality of parallel rollers 524 which are rotatably connected at their ends with a drive mechanism (e.g., chains, etc.). The rollers 524 move in the direction indicated by arrows $A_9$ while also rotating in the clockwise direction as viewed from FIG. 51. Under the effect of the movement and rotation of the rollers 524, eggs 1' travel along the direction indicated by arrow $A_9$ (with their narrow ends generally perpendicular to the direction of travel indicated by arrow $A_9$) and are fed into respective channels 528 and then into respective receiving cups 530 with their narrow ends pointing downwards, as illustrated in FIG. 51. The receiving cups 530 are mounted on an endless conveyor system 540 that moves the cups in the direction indicated by arrows $A_9$. An exemplary backfill apparatus 520 is described in U.S. Pat. No. 3,592,327, which is incorporated herein by reference in its entirety.

Each receiving cup 530 transports a respective egg 1' to a treatment station 40, such as the INOVOJECT® automated injection system. For example, in the illustrated embodiment of FIG. 49, eggs 1' within respective receiving cups 530 are transported through respective treatment and transfer stations 40, 50. Each treatment station 40 contains a set of injection delivery devices that are configured to inject a substance into eggs V. A transfer station 50 is provided downstream of each treatment station 40 and is configured to transfer eggs 1' into respective baskets (not shown).

Backfill apparatus according to embodiments of the present invention may have various configurations, and are not limited to the illustrated embodiments. Backfill apparatus may include different numbers of channels and may include receiving cups of varying sizes and/or configurations. Moreover, various types of rollers and conveyor systems may be utilized without limitation.

Treatment Followed By Sorting

Figure 52:
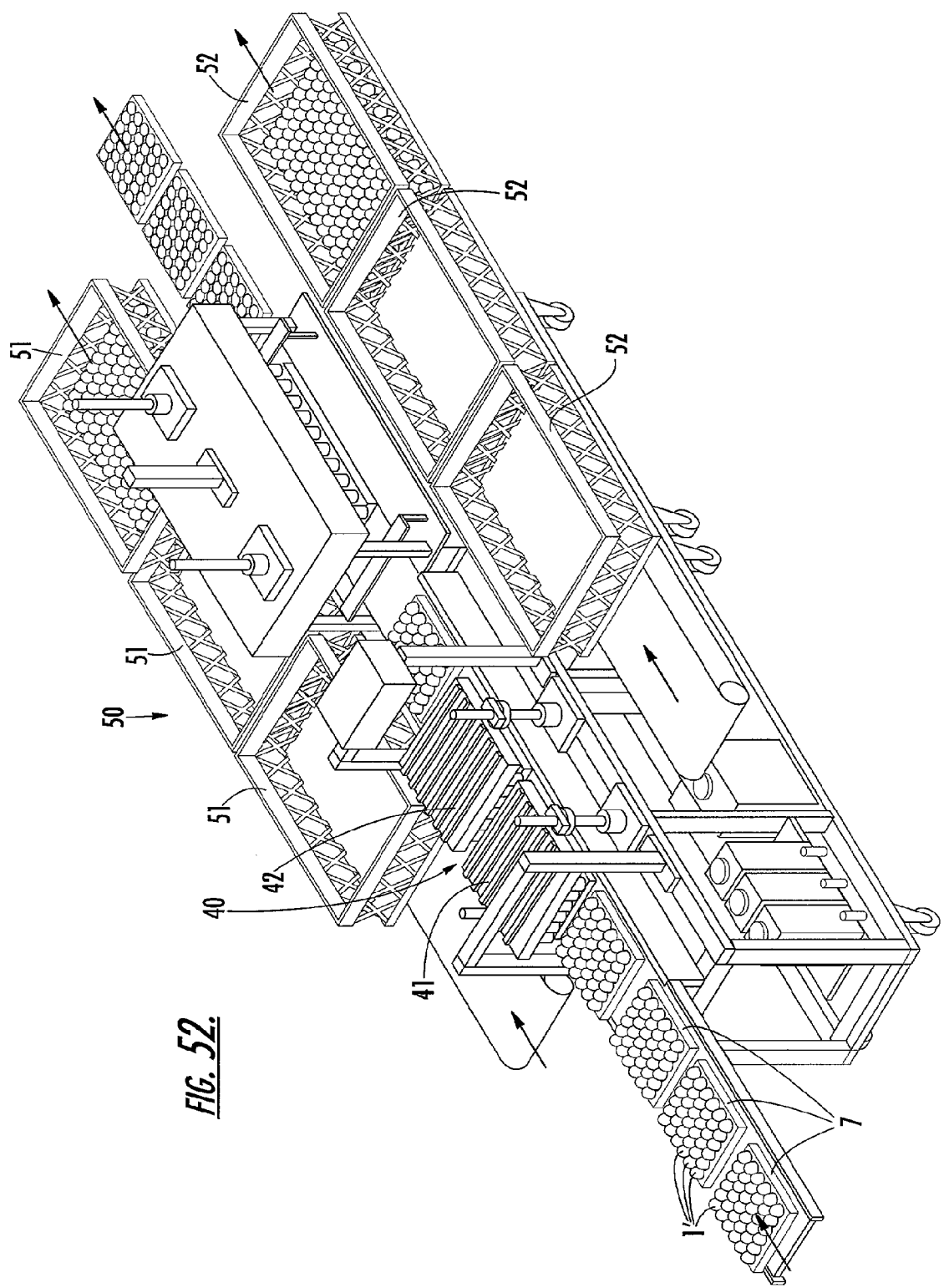
FIG. 52 is a perspective view of a treatment and sorting station according to other embodiments of the present invention.

Referring to FIG. 52, treatment and sorting/transfer stations 40, 50 according to other embodiments of the present invention are illustrated. As a flat 7 of post-sampled eggs 1' is conveyed through the treatment station 40, the controller 20 (FIG. 11) selectively generates an injection signal to the treatment station 40 to inject those eggs 1' which have been identified as having a particular characteristic.

As will be apparent to those skilled in the art, generation of a selective injection signal may be achieved by various approaches, including generating a signal that causes the injection of selected eggs, or generating a signal that prevents the injection of non-selected eggs.

In the illustrated embodiment, a pair of injection stations 41, 42, such as the INOVOJECT® automated injection system, are employed. The first injection station 41 contains a first set of injection delivery devices that are configured to inject a substance into eggs 1' identified as having a first characteristic. The second injection station 42 contains a first set of injection delivery devices that are configured to inject a substance into eggs 1' identified as having a second characteristic. For example, if gender is the identified characteristic, the first injection station 41 can inject a vaccine or other substance into male eggs, and the second injection station 42 can inject a vaccine or other substance into female eggs.

A sorting/transfer station 50 may be provided downstream of the treatment station 40. The controller 20 generates a selective removal signal to cause the sorting/transfer station 50 to remove eggs having various identified characteristics (e.g., gender). The sorting/transfer station 50 may employ suction-type lifting devices as described above with respect to the lifting heads 132, 134 of the material extraction apparatus 30. Any other suitable means for removing the eggs may be used as well, such apparatus being known to those of ordinary skill in the art.

In the illustrated embodiment, eggs identified according to gender are sorted. Male eggs are transferred from egg flats 7 to respective baskets 51 and female eggs are transferred from egg flats 7 to respective baskets 52. Any non-live eggs may be left in the egg flats 7 for subsequent processing or disposal.

The sorting/transfer station 50 preferably operates automatically and robotically. Alternatively, selected eggs may be identified on the operator interface 22, optionally marked, and removed by hand.

According to embodiments of the present invention, eggs may be sorted based on viability, pathogen content, and/or genetic analysis. For example, eggs that contain pathogens can be pulled out of the normal population and not transferred to the hatcher, thereby preventing horizontal transmission of disease agents.

Information Collection

Systems according to embodiments of the present invention can provide valuable information to those in the poultry industry. For example, identification and compilation of classes of embryonic mortality can provide feedback on breeder flock management, egg handling and incubation conditions. Knowledge of number of viable eggs and sex can provide an accurate prediction of product and streamline and optimize logistics. Identification of pathogen detection and compilation of data can help manage disease. Identification of genetic markers can be utilized by breeders. Identification of nutritional elements within the egg can be used to optimize feeding diets and regimes. Identification of proteins or small molecules can be used to track or predict or optimize performance or immunity. In addition, one could use information from embodiments of the present invention to track egg constituents and then relate them to bird performance and use this information for product development.

Material Extraction/Assaying Combination

Figure 53:
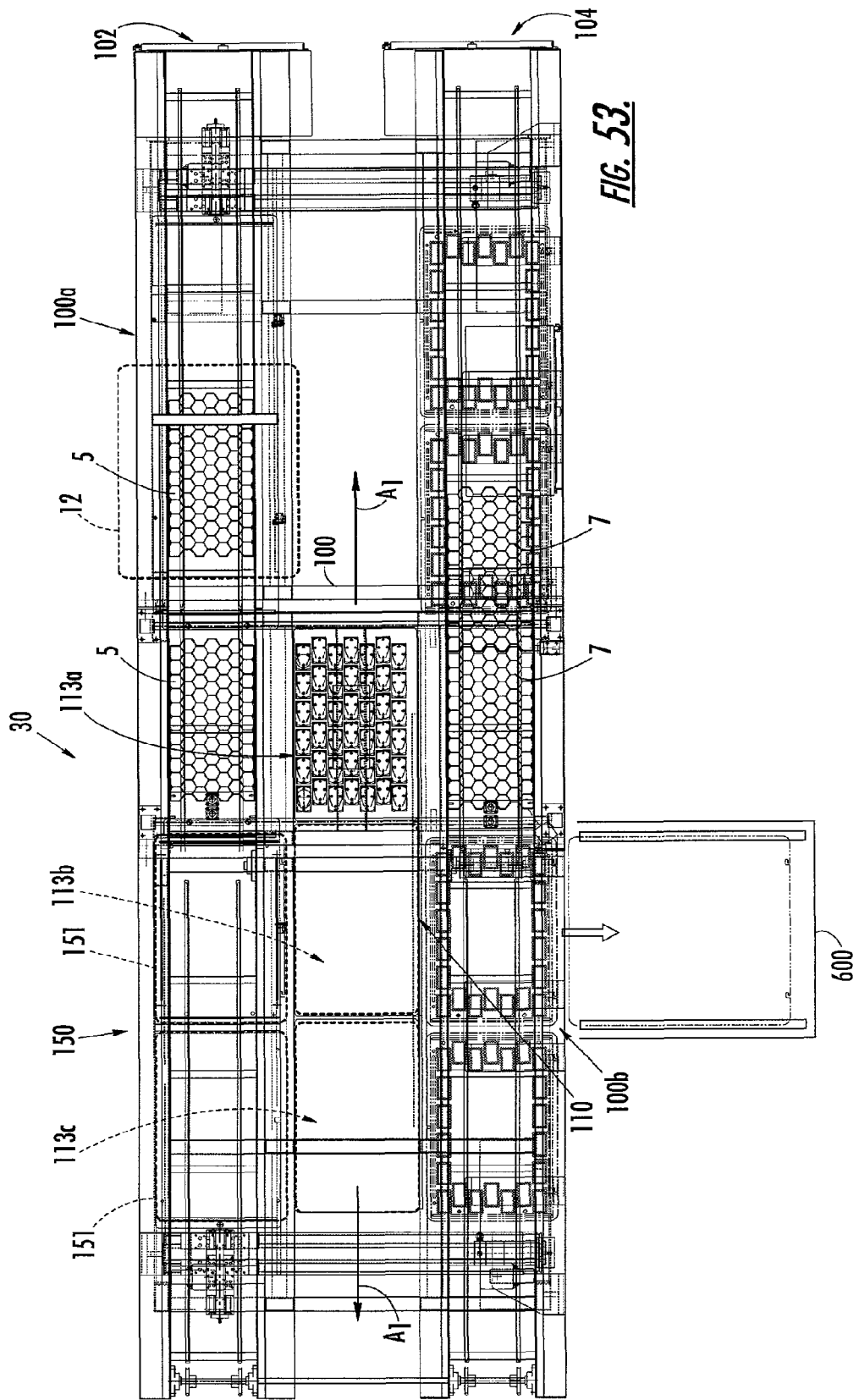
FIG. 53 is a plan view of the egg flat conveyor systems and egg cradles of the material extraction apparatus of FIG. 14 taken along lines 16-16 that includes an assaying apparatus for assaying material extracted from a plurality of eggs according to embodiments of the present invention.
Figure 54:
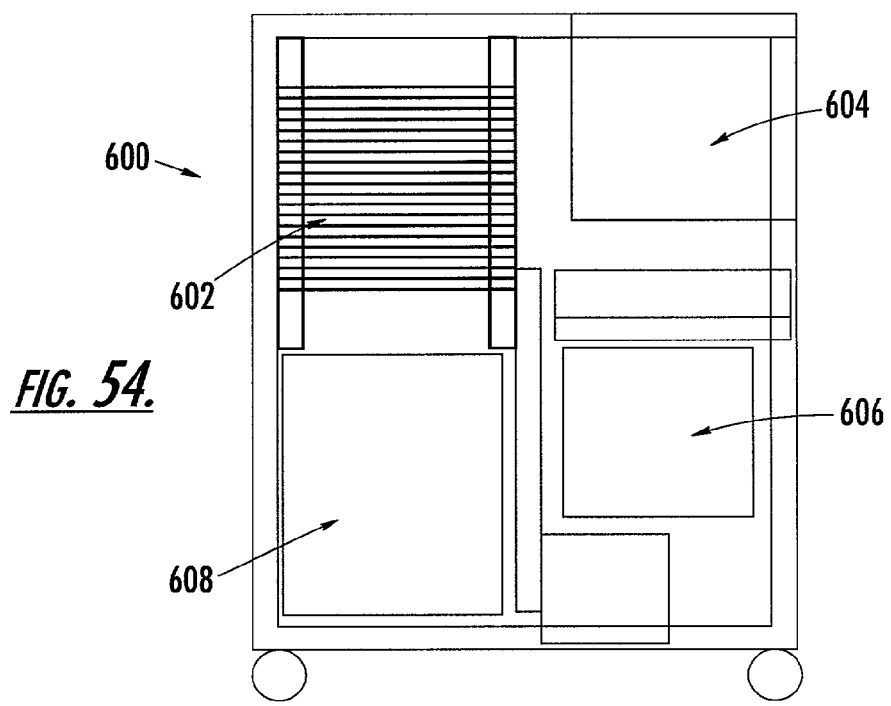
FIG. 54 is block diagram of the assaying apparatus of FIG. 53.

According to embodiments of the present invention, a material extraction station may be configured to perform various assaying techniques for determining characteristics of eggs. FIGS. 53-54 illustrate a module 600 that is configured to attach to the material extraction apparatus 30 of FIG. 14. An exemplary module 600 for assaying material in accordance with embodiments of the present invention, and specifically using the competitive antibody assay procedure described below, is manufactured by Luminex Corporation, Austin, Tex.

The illustrated module 600 is configured to pull small samples of material extracted from eggs out of respective sample receptacles and feed them into a reader system for analysis. Preferably, a sample tray 151 having a plurality of sample receptacles 152 that contain material extracted from eggs is fed into the illustrated module 600 from the sample tray handling system 150.

A competitive antibody assay procedure is utilized by the module 600 and is based on antibody coupled to internally dyed "beads". The illustrated module 600 may be configured to handle any number if sample trays 151 at a time. For each sample tray 151, the module 600 includes a liquid handler that is configured to pull small samples from respective sample receptacles in a sample tray 151 and feed them into a reader system.

Specifically, if allantoic fluid is the material that has been extracted from eggs, the module 600 takes allantoic fluid and mixes it with polystyrene microspheres, or beads (available from Luminex, Inc., Austin, Tex.) which are coupled to estradiol molecules. Fluorescently-labeled anti-estradiol antibody is added to the bead/allantoic fluid mixture and mixed. This mixture is then incubated at room temperature in the dark for 15-30 minutes. An amount of the mixture (e.g., 50 µl-60 µl) is withdrawn and the assay results are provided by an analyzer (Luminex, Inc., Austin, Tex.) which utilizes lasers to detect a fluorescent signal. This assay procedure is based on competitive inhibition. A competition for the fluorescently labeled anti-estradiol antibody is established between the estradiol coupled to the beads and the estradiol in the allantoic sample. If the allantoic sample is from a female embryo and contains estradiol, the estradiol in the sample will compete for the fluorescently tagged antibody and less antibody will bind to the beads. The assay signal, dependent upon the amount of antibody bound to the beads, will be lower from a female-derived sample (inhibition of fluorescent signal). If the allantoic sample is from a male embryo and does not contain estradiol, there will be much less competition from estradiol in the sample and more beads will have the antibody bound. The more antibody bound to the beads, the higher the signal.

According to embodiments of the present invention, coupled beads and antibody may be already present within sample receptacles of a sample tray. By eliminating the additional steps of adding beads and antibody with extracted allantoic fluid, assaying time may be decreased, which may be commercially advantageous.

Referring to FIG. 54, the illustrated module 600 includes a template handling system 602, a high throughput reader system 604 for analyzing samples, controls 606, and a fluid supply and drain system 608.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as to other embodiments, are intended to be included within the scope of the appended claims. The invention is defined by the following claims, with equivalents of the claims to be included therein.

That which is claimed:

1. An egg processing system, comprising:
   a classifier configured to identify live avian eggs among a plurality of eggs conveyed in an egg flat;
   a sampling apparatus configured to extract material from the eggs identified as live avian eggs by the classifier, and further configured to deposit the extracted material into respective sample receptacles of a sample tray;
   a sample tray handling system configured to position the sample tray proximate to the sampling apparatus for receiving the extracted material therefrom; and
   an assaying station configured to assay material in the sample tray extracted from each live avian egg so as to identify eggs having a characteristic.

2. The egg processing system of claim 1, further comprising an incoming egg flat conveyor system configured to transport the egg flat through the classifier and proximate to the sampling apparatus.

3. The egg processing system of claim 1, further comprising a treatment station configured to treat selected live avian eggs based upon the identified characteristic.

4. The egg processing system of claim 1, further comprising a sorting station configured to sort the live avian eggs based upon the identified characteristic.

5. The egg processing system of claim 1, further comprising a transfer apparatus configured to lift and rearrange the live avian eggs, the transfer apparatus having an expandable and collapsible array of manifold blocks and associated vacuum cups.

6. The egg processing system of claim 1, wherein the assaying station comprises a holding area configured to receive and hold the sample tray containing material extracted from the live avian eggs for a predetermined period of time.

7. The egg processing system of claim 1, wherein the assaying station comprises a biosensor application area configured to add a biosensor to the extracted material in the sample receptacles of the sample tray.

8. The egg processing system of claim 1, wherein the assaying station comprises a color application area configured to add a color substrate to the extracted material in the sample receptacles of the sample tray.

9. The egg processing system of claim 7, wherein the assaying station comprises a read area configured to analyze the extracted material to determine the characteristic.

10. The egg processing system according to claim 9, wherein the assaying station comprises a plurality of conveyor systems configured to transport the sample tray sequentially through the respective areas.

11. The egg processing system of claim 7, wherein the assaying station comprises one or more environmentally-controlled chambers for holding the sample tray over a predetermined period of time subsequent to receiving the biosensor.

12. The egg processing system according to claim 1, wherein the sample tray handling system is further configured to receive a plurality of discrete sample trays for processing.

13. An egg processing system, comprising:
   a classifier configured to identify live avian eggs among a plurality of eggs conveyed in an egg flat;
   a sampling apparatus configured to extract material from the eggs identified as live avian eggs by the classifier, and further configured to deposit the extracted material into respective sample receptacles of a sample tray;
   an incoming egg flat conveyor system configured to transport the egg flat through the classifier and proximate to the sampling apparatus;
   a sample tray handling system configured to position the sample tray proximate to the sampling apparatus for receiving the extracted material therefrom; and
   an assaying station configured to assay material in the sample tray extracted from each live avian egg so as to identify eggs having a characteristic, the assaying station comprising:
      an application area configured to add a substance to the extracted material in the sample receptacles of the sample tray;
      a read area configured to analyze the extracted material to determine the characteristic;
      one or more environmentally-controlled chambers for holding the sample tray over a predetermined period of time subsequent to receiving the substance; and
      at least one conveyor system configured to transport the sample tray sequentially through the respective areas and chambers.

14. The egg processing system of claim 13, wherein the application area comprises a color application area configured to add a color substrate to the extracted material in the sample receptacles of the sample tray.

15. The egg processing system of claim 13, wherein the application area comprises a biosensor application area configured to add a biosensor to the extracted material in the sample receptacles of the sample tray.

16. The egg processing system according to claim 13, wherein the sample tray handling system is further configured to receive a plurality of discrete sample trays for processing.

* * * * *